(12) United States Patent
Krippner et al.

(10) Patent No.: US 8,420,067 B2
(45) Date of Patent: *Apr. 16, 2013

(54) TARGETED POLYLYSINE DENDRIMER THERAPEUTIC AGENT

(75) Inventors: Guy Yeoman Krippner, Newtown (AU); Charlotte Claire Williams, Carlton (AU); Brian Devlin Kelly, Ringwood East (AU); Scott Andrew Henderson, Rowville (AU); Zemin Wu, Doncaster East (AU); Pasquale Razzino, Fairfield (AU)

(73) Assignee: Starpharma Pty Ltd, Prahan, Victoria (AU)

( * ) Notice: Subject to any disclaimer, the term of this patent is extended or adjusted under 35 U.S.C. 154(b) by 740 days.

This patent is subject to a terminal disclaimer.

(21) Appl. No.: 12/377,253

(22) PCT Filed: Aug. 10, 2007

(86) PCT No.: PCT/AU2007/001126
§ 371 (c)(1),
(2), (4) Date: Apr. 16, 2009

(87) PCT Pub. No.: WO2008/017125
PCT Pub. Date: Feb. 14, 2008

(65) Prior Publication Data
US 2010/0292148 A1  Nov. 18, 2010

(30) Foreign Application Priority Data

Aug. 11, 2006 (AU) ................................ 2006904385

(51) Int. Cl.
*A61K 38/00* (2006.01)
*A61K 31/74* (2006.01)
*A61K 31/785* (2006.01)

(52) U.S. Cl.
USPC .................... 424/78.08; 424/78.35; 530/323; 514/1.1

(58) Field of Classification Search ............... 424/78.08, 424/78.35; 530/323; 514/1.1
See application file for complete search history.

(56) References Cited

U.S. PATENT DOCUMENTS

| 5,229,490 | A | 7/1993 | Tam | |
|---|---|---|---|---|
| 7,371,755 | B1 * | 5/2008 | Krippner et al. | 514/252.01 |
| 7,985,424 | B2 * | 7/2011 | Tomalia et al. | 424/486 |
| 8,258,259 | B2 * | 9/2012 | Krippner et al. | 530/323 |

FOREIGN PATENT DOCUMENTS

| AU | 2002 245 932 B2 | 10/2002 |
|---|---|---|
| EP | 0 884 327 * | 3/2001 |
| EP | 0 884 327 B1 | 3/2001 |
| JP | 9512264 A | 12/1997 |
| JP | 2004515457 A | 5/2004 |
| JP | 2005532276 A | 10/2005 |
| WO | 95/28966 A1 | 11/1995 |
| WO | WO 99/01160 A1 | 1/1998 |
| WO | WO 98/43677 A1 | 10/1998 |
| WO | 01/87348 A2 | 11/2001 |
| WO | WO 02/079299 * | 10/2002 |
| WO | 03/076455 A2 | 9/2003 |
| WO | WO 03/089010 A1 | 10/2003 |

OTHER PUBLICATIONS

Vlasov et al., 2004, Lysine Dendrimers and Their Starburst Polymer Derivatives: Possible Application for DNA Compaction and in vitro Delivery of Genetic Constructs, Russian Journal of Bioorganic Chemistry, 30(1): 15-24.*
Kim et al., 2004, PAMAM-PEG-PAMAM: Novel Triblock Copolymer as a Biocompatible and Efficient Gene Delivery Carrier, Biomacromolecules, 5: 2487-2492.*
Choi et al., 2000, Synthesis of a Barbell-like Triblock Copolymer, Poly(L-lysine)Dendrimer-block-Poly(ethylene glycol)-block-Poly(L-lysine)Dendrimer, and Its Self-Assembly with Plasmid DNA, 122: 474-480.*
Boas et al., 2004, Dendrimers in drug research, Chem. Soc. Rev., 33: 43-63.*
Crespo et al., 2005, Peptide and Amide Bond-Containing Dendrimers, Chem. Rev., 105: 1663-1681.*
Choi, J.S. et al. 2000 "Synthesis of a Barbell-like triblock copolymer, poly(L-lysine) dendrimer-block-poly(ethylene glycol)-block-poly(L-lysine) dendrimer, and its self-assembly with plasmid DNA" *J. Am. Chem. Soc.* 122: 474-480.
Kurita, T. et al. 1999 "Syntheses and biological activities of dendrimeric mastoparans" *Chemistry Letters* 3:193-194.
Qualmann, B. et al. 1996 "Synthesis of Boron-Rich Lysine Dendrimers as Protein Labels in Electron Microscopy" *Angewandte Chemie International Edition in English* 8:909-911.
Ramaswamy, C. et al. 2003 Dendriplexes and their characterisation *Int. J. of Pharmaceutics* 254:17-21.
Roy, R. and Baek, M.-G. 2002 "Glycodendrimers: novel glycotope isosteres unmasking sugar coding. Case study with T-antigen markers from breast cancer MUC1 glycoprotein" *Reviews in Molecular Biotechnology* 90: 291-309.
Vlasov, G. et al. 2004 "Lysine dendrimers and their starburst polymer derivatives: possible application for DNA compaction and in vitro delivery of genetic constructs" *Russian J. of Bioorg. Chem.* 30 (1): 12-20.
Klajnert, et al., "Dendrimers: properties and applications", Acta Biochimica Polonica, vol. 48, No. 1/2001, pp. 199-208.
Liu, et al., Water Soluble Dendrimer-Poly(ethylene glycol) Starlike Conjugates as Potential Drug Carriers, Journal of Polymer Science Part A: Polymer Chemistry, vol. 37, Mar. 25, 1999, pp. 3492-3503.
Nicolle, et al., 2002 "The Impact of Rigidity and Water Exchange on the Relaxivity of a Dendritic MRI Contract Agent", Chem. Eur. J. 2000, 8(5), 1040-1048.
Supplemental European Search Report issue on Jul. 12, 2012 for European Application No. EP 07 78 4766.

* cited by examiner

*Primary Examiner* — Amber D. Steele
(74) *Attorney, Agent, or Firm* — Knobbe, Martens, Olson & Bear, LLP

(57) ABSTRACT

The present invention relates generally to branched macromolecules bearing functional moieties. In particular, the invention relates to dendrimers, derived from lysine or lysine analogues, bearing a plurality of functional moieties. The invention further relates to the use of such macromolecules, particularly in therapeutic applications, and compositions comprising them.

30 Claims, No Drawings

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial sequence
<220> FEATURE:
<223> OTHER INFORMATION: Synthetic peptide

<400> SEQUENCE: 1

Gly Gly Gly Phe
1
```

US 8,420,067 B2

TARGETED POLYLYSINE DENDRIMER THERAPEUTIC AGENT

This application is U.S. National Phase of International Application PCT/AU2007/001126, filed Aug. 10, 2007 designating the U.S., and published in English as WO 2008/017125 on Feb. 14, 2008, which claims priority to Australian Patent Application No. 2006904385 filed Aug. 11, 2006.

REFERENCE TO SEQUENCE LISTING

This application incorporates by reference the sequence listing submitted as ASCII text filed via EFS-Web on Jul. 3, 2012. The Sequence Listing is provided as a file entitled "13529584_1.TXT", created on Jul. 3, 2012 and which is approximately 385 bytes in size.

FIELD OF THE INVENTION

The present invention relates generally to branched macromolecules. In particular, the invention relates to dendrimers, derived from lysine or lysine analogues, bearing a plurality of functional moieties. The invention further relates to the use of such macromolecules, particularly in therapeutic applications, and compositions comprising them.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Identification of new compounds for use in pharmaceutical preparations is an important part of the search for more reliable and effective therapies. However just as important is the development and modification of known compounds, reducing the risks associated with a new drug candidate and significantly reducing the development and cost to bring the drug to clinical development.

Many drugs fail in clinical trials either because their physical properties (particularly solubility) make them difficult to formulate, or because of a poor therapeutic index that leads to toxic effects during the high drug concentrations that occur just after dosing. Other short comings include poor absorption, poor bioavailability, instability, systemic side effects due to an inability to target the drugs, and the inability to control their biodistribution, metabolism and renal or hepatic clearance once administered. Similarly some current products on the market can be improved with regard to such issues.

A number of approaches have been tried to improve a pharmaceutical compound's profile including the formulation of the pharmaceutical agent in a liposome, micellar or polymeric micelle formulation, as well as covalent attachment of the pharmaceutical agent to a hydrophilic polymer backbone.

The characteristics of an ideal profile modifying agent include being a well defined structure, allowing precise control of the absorption, distribution, metabolism and excretion (ADME) characteristics (also referred to as pharmacokinetics) of the compound in question and advantageously being able to carry multiple compounds per agent or construct. The toxicity of a compound in question can be ameliorated through its controlled release from the said agent or construct, the body only being exposed to therapeutic plasma concentrations of the compound.

In recent years, dendritic macromolecules, or dendrimers, have been found to have increasing applications in biotechnology and pharmaceutical applications. Dendritic macromolecules are a special class of polymers with densely branched structures that are characterized by higher concentrations of functional moieties per unit of molecular volume than ordinary polymers. There are three subclasses of dendritic macromolecules: random hyperbranched polymers; dendrigraft polymers and dendrimers (which includes dendrons), classified on the basis of the relative degree of structural control present in each of the dendritic architectures (Fréchet and Tomalia "Dendrimers and other Dendritic Polymers", Wiley and Sons, New York, 2002). The unique properties of dendrimers in particular, such as their high degree of branching, multivalency, globular architecture and well-defined molecular weight, make them promising new scaffolds for pharmaceutical applications. In the past decade, research has increased on the design and synthesis of biocompatible dendrimers and their application to many areas of bioscience including macromolecular drugs, drug delivery, biomedical imaging and medical devices.

The potential utility of dendritic polymers both as drug delivery vectors and pharmaceutical actives has received increasing interest in recent years. However, whilst the literature is replete with reports of, for example, synthetic schemes for dendrimer assembly, descriptions of dendrimer-drug interactions and drug loading efficiencies and increasingly, in vitro evaluations of dendrimer interactions with cell lines, there is very little information describing the fundamental pharmacokinetic and metabolic fate of dendrimers.

Further, it is still a challenge to prepare dendrimers that circulate in the blood long enough to accumulate at target sites, but that can also be eliminated from the body at a reasonable rate to avoid long-term build up. In addition, the tissue localisation of dendrimers is still difficult to predict in advance and more studies are required to determine the effect of peripheral dendritic groups on these properties. An additional area that needs to be investigated is the release of drugs from dendrimers. Steric hindrance associated with the dense globular dendritic architecture makes the engineering of the enzymatically cleavable linkages difficult.

It has surprisingly been found that, by introducing one or more functional moieties, as described herein, the efficacy of the macromolecule may be significantly improved, but without significant adverse impact on, or interference with, other functional moieties which may be present.

SUMMARY OF THE INVENTION

The present invention relates to dendrimers having a first functional moiety attached to the core moiety thereof and at least one second functional moiety attached to the surface of the outermost layer of building units (surface building units) of the dendrimer. In particular, the invention relates to a dendrimer comprising a core and one or more layers of lysine or lysine analogue building units wherein the dendrimer has a first functional moiety attached to a nitrogen atom of the core moiety and one or more second functional moieties attached to surface amino nitrogen atoms of the outermost layer of building units.

Accordingly, in a first aspect, the present invention provides a macromolecule comprising:

(i) a core moiety having a first amino nitrogen atom for attachment to a first functional moiety and at least two further amino nitrogen atoms for attachment to lysine or lysine analogue building units;
(ii) a first functional moiety attached to the core moiety through the first amino nitrogen atom;
(iii) at least one layer of lysine or lysine analogue building units, the outermost layer having surface amino nitrogen atoms for attachment to one or more second functional moieties, said layers attached to the core moiety through the at least two further amino nitrogen atoms of the core moiety; and
(iv) one or more second functional moieties attached to the surface amino nitrogen atoms of the outermost layer of lysine or lysine analogue building units;
wherein
the first and second functional moieties each comprise an agent selected from the group consisting of pharmaceutically active agents, interacting agents and pharmacokinetic modifying agents.

The incorporation of a pharmaceutically active agent into a macromolecule of the invention may provide an extended release profile for the agent, or extend its plasma residence time, in use. The incorporation of a pharmacokinetic modifying agent, into such a macromolecule may further enhance the release profile of the pharmaceutically active agent, or further extend its plasma residence time, in use. The incorporation of an interacting agent, such as a targeting agent, or capture agent into a macromolecule of the invention may provide an increase in concentration of the macromolecule at target cell or tissue types, and advantageously an increased uptake of the macromolecule into target cell or tissue types, or targeting of the macromolecule to a protein, DNA or RNA target in use or a more efficient, reproducible means of attaching the macromolecule to the surface of a component of a diagnostic or medical device, in use.

In turn, two or more of the different types of functional moieties described above, may be incorporated into the macromolecule to provide a macromolecule having multiple complementary functionalities.

The second functional moiety may be the same or different to the first. A second functional moiety may be attached to only one, some, or all of the surface amino nitrogen atoms. The macromolecule may contain only first and second functional moieties or may include, one or more third (and optionally fourth and fifth), functional moieties as defined herein which may be optionally attached to surface amino groups to provide a macromolecule with a first functional moiety at the core and at least one of each of second and third (and optionally fourth and fifth), functional moieties on the surface of the macromolecule. The third (and optionally fourth and fifth) functional moieties may be selected from pharmaceutically active agents, pharmacokinetic modifying agents and interacting agents.

The functional moieties may be independently directly attached to the appropriate nitrogen atom, or attached via a cleavable or non-cleavable linker.

The macromolecules according to this aspect of the present invention are particularly suitable for the presentation of a pharmaceutically active agent. Thus, in one embodiment of the invention, at least the first and/or second functional moiety comprises a pharmaceutically active agent. The macromolecule may include a single pharmaceutically active agent attached to the core and/or surface building units or a plurality of pharmaceutically active agents (which may be the same or different), on the core and/or at selected points on the surface of the macromolecule.

In a particular example of this embodiment, a pharmaceutically active agent is attached to the core moiety of the macromolecule. In further examples thereof, the pharmaceutically active agent is a protein or polypeptide.

In some embodiments of the invention, at least the first and/or second functional moiety comprises a pharmacokinetic modifying agent. The macromolecule may include a single pharmacokinetic modifying agent at the core and/or the surface building units or a plurality of pharmacokinetic modifying agents (which may be the same or different) at the core and/or selected points on the surface of the macromolecule.

The presentation of the macromolecule including a first functional moiety, comprising a pharmaceutically active agent, and at least a second functional moiety, comprising a pharmacokinetic modifying agent, may advantageously result in improved performance of the macromolecule.

In further embodiments of the invention, there is provided a macromolecule wherein the first functional moiety comprises a targeting agent, such as an antibody, and the at least one second functional moiety comprises a pharmaceutically active agent.

In another aspect of the invention there is provided a process for preparing a macromolecule as described above, including the steps of:
(i) providing
  (a) a dendrimer comprising:
    (i) a core moiety having a first amino nitrogen atom for attachment to a first functional moiety and at least two further amino nitrogen atoms for attachment to lysine or lysine analogue building units;
    (ii) a first protecting group at the first amino nitrogen atom;
    (iii) at least one layer of lysine or lysine analogue building units, the outermost layer having surface amino nitrogen atoms for attachment to the one or more second functional moieties, said layers attached to the core moiety through the at least two further amino nitrogen atoms of the core moiety; and
    (iv) a second protecting group at one or more of the surface amino nitrogen atoms of the outermost layer of lysine or lysine analogue building units;
  (b) a first functional moiety; and
  (c) at least one second functional moiety;
(ii) selectively removing the second protecting group(s) using reaction conditions to which the first protecting group is inert;
(iii) attaching the at least one second functional moiety to the deprotected surface amino nitrogen atom(s);
(iv) removing the first protecting group;
(v) attaching the first functional moiety to the deprotected first amino nitrogen atom or the linker group.

In a further aspect of the present invention, there is provided a pharmaceutical composition including a macromolecule according to the invention and a pharmaceutically acceptable excipient, carrier or adjuvant therefor.

In yet a further aspect, the invention provides a macromolecule as described herein for use in therapy.

The macromolecule and pharmaceutical compositions containing the macromolecule according to this aspect of the present invention may be utilised in various applications, as discussed herein, where the ability to direct or bind the pharmaceutically active agent to a particular site of action, or to a particular cell or tissue type, or to a protein, DNA or RNA target, or substrate or to modify the pharmacokinetics thereof.

DETAILED DESCRIPTION OF THE EMBODIMENTS

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The term "antibody" as used herein in the specification and claims includes the full antibody, or a derivative or a fragment, such as that derived from enzymatic or chemical cleavage or obtained recombinantly, or a mimic of the binding region of an antibody produced either by way of protein expression techniques or through chemical synthesis, which retains the specific binding activity. The term includes monoclonal antibodies and all the various forms derived from monoclonal antibodies, including but not limited to full-length antibodies (e.g. having an intact Fc region), antigen-binding fragments, including for example, Fv, Fab, Fab' and $F(ab')_2$ fragments; and antibody-derived polypeptides produced using recombinant methods such as single chain antibodies. The terms "antibody" and "antibodies" as used herein also refer to human antibodies produced for example in transgenic animals or through phage display, as well as chimeric antibodies and humanized antibodies.

The term "attached" as used herein in the specification and claims refers to a connection between chemical components of the macromolecule by way of covalent bonding, hydrogen bonding, adsorption, metallic bonding, Van der Waals forces, ionic bonding, chelate-metal-chelate linkages, a ligand-receptor linkages, duplexes or triplexes formed from complimentary strands of DNA, RNA of peptide analogues thereof, or any combination thereof. A particular form contemplated herein is covalent bonding. The attachment may be direct, or indirect through an intervening moiety or moieties, such as a bridge, spacer, or linker moiety or moieties, which terms may be used interchangeably herein. Furthermore, a linker group or functional moiety or amine may be further modified by a modifier to facilitate the attachment.

The term "selected point of attachment" as used herein in the specification and claims refers to an amine group or amine groups of the dendrimer polymer that are differentiated from other amine groups of the dendrimer polymer in being uniquely reactable at a defined stage in the synthesis of the dendrimer polymer, thereby allowing the attachment of a functional moiety or dendritic motif. This advantageously allows the surface position and distribution of a functional moiety to be known. The selected point of attachment may therefore be at the first nitrogen atom of the core moiety or on the surface of the dendrimer.

The term "binding" as used herein in the specification and claims refers to the ability of a given molecule to be captured (bound) and held by another, for example a ligand to interact with a target such that the interaction between the ligand and its target is relatively specific. Examples include the specific interaction between an antibody, or derivatives and fragments thereof and the antibody target (receptor); or the interaction between a small molecule, such as biotin, folate or digoxin, and their respective targets (receptors or antibodies).

The term "derivatives" and "fragments" as used herein in the specification and claims, and when used in relation to polypeptides, particularly antibodies refers to functional equivalents having similar amino acid sequence, say at least 80, 85, 90, or 95% homology, and retaining, at least to some extent, the activities of the polypeptide.

The term "lysine analogue" as used herein in the specification and claims refers to a molecule which has a single apex carboxyl group and two or three primary amine groups. In one instance they may be asymmetric, as for the parent Lysine 1 and this is defined as meaning that the bonds and atoms that join the primary amines to the carboxylate apex are different. In a second instance lysine analogues may be symmetrical which is defined to mean that the bonds and atoms that join each primary amine to the carboxylate are identical, and which disregards the asymmetry that is potentially introduced when each primary amine is further reacted.

The term "dendritic motif" as used herein in the specification and claims refers to a discrete unit of the macromolecule. When one of the macromolecule branches is cut at the bond which connects one of the reactable amines of the building unit or core to the apex carboxylate group of the attached building unit, the dendritic motif will "fall out". The apex carboxylate group of the dendritic motif represents the point at which the dendritic motif would be attached to a growing macromolecule core during the process of synthesising a macromolecule of the invention.

The term "building unit" as used herein in the specification and claims refers to lysine or lysine analogues used in the assembly of dendritic motifs. The building unit may be a subsurface building unit, being part of the layer, or generation, of building units bearing amines that may be further reacted with the apex carboxylate group of a further building unit. The layers may in turn be described as the surface-but-one layer, meaning the first subsurface immediately adjacent the surface layer; the surface-but-two layer is the second layer below the surface layer; the surface-but-three layer is the third layer below the surface layer; and so on.

As used herein, the term "layer" or "generation" refers to a plurality of building units having the same degree of connectivity to the core moiety, i.e. having the same number of building units linking the building unit in question to the amino nitrogen atoms of the core. For example, building units which are attached, either directly or via a linker group, to the nitrogen atoms of the core moiety are referred to the first layer or generation. Building units which have one building unit between them and the nitrogen atoms of the core moiety are referred to as the second layer or generation. A layer or generation of building units must contain at least two building units. Each layer of building units is homogenous with regard to the building unit used, however, different building units may be used to prepare different layers. Thus in certain embodiments of the invention, the macromolecule is composed of one or more layers of a single type of building unit, e.g. lysine. In other embodiments, the macromolecule comprises at least two layers of building units wherein at least two layers are composed of different building units.

The term "small molecule" refers to any non-peptide molecule which has a molecular weight of up to about 1500 Daltons, such as from about 200 to about 600, or from about 600 to about 1000 or from about 1000 to about 1500 Daltons.

The term "surface" as used herein, is used in reference to the outermost layer of building units of the dendrimer.

The term "surface building unit" as used herein in the specification and claims refers to the outermost layer of building units of the macromolecule. i.e. there are no further building units attached to the surface amines of a surface building unit.

The term "surface amine" or "surface amino" or "surface amino nitrogen atom" as used herein in the specification and claims refers to any of the outer-most nitrogens of the dendritic motif which derive from surface building units. These surface amines represent the points of attachment for additional building units, linkers or functional moieties.

The term "functional moiety" as used herein in the specification and claims refers to any group, as defined herein, that may be attached, either directly or indirectly, at a first amino nitrogen of the core or a surface amine with the purpose of serving the stated function. The nature and number of functional moieties may be determined by standard analytical techniques including proton/carbon NMR, ESI or MALDI mass spectrometry.

The term "amine-protecting groups", as used herein in the specification and claims refers to groups for which an order of removal exists such that those groups that are not meant for cleavage are inert to the cleavage conditions. When protecting groups are defined as "resolvable", this means that the conditions for removal of one group may affect the integrity of the second group and this requires that the second group be removed first if the integrity of the first group is to be maintained. When protecting groups are further defined as "orthogonal", this means that each group is inert to the cleavage conditions required to remove each of the other groups of the orthogonal set. It is important to note that protecting groups are resolvable or, orthogonal only when the appropriate reaction conditions are used. There are general methods described in the art for the selective mono-protection of polyamine molecules. Such methods are described in Krapcho and Kuell *Synthetic Commun.* (1990) 20:2559.

The macromolecules of the present invention are constructed from at least one layer of lysine or lysine analogue building units. Examples of building units contemplated by the invention include the following (where # depicts the carbonyl residue of the apex carboxyl group):

Lysine* 1 having the structure:

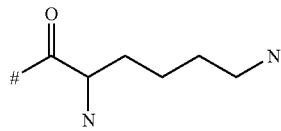

1

Glycyl-Lysine* 2 having the structure:

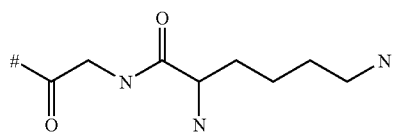

2

Analogue 3, having the structure below, where a is an integer 1 or 2; and b and c are independently integers 1, 2, 3 or 4

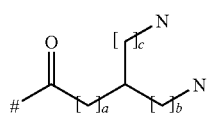

3

Analogue 4, having the structure below, where a is an integer 0, 1 or 2; and b and c are independently integers 2, 3, 4, 5 or 6

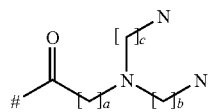

4

Analogue* 5, having the structure below, where a is an integer 0, 1, 2, 3, 4 or 5; and b and c are independently integers 1, 2, 3, 4 or 5

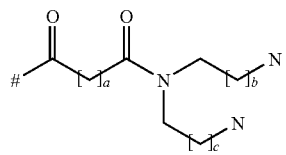

5

Analogue 6, having the structure below, where a is an integer 0, 1, 2, 3, 4 or 5; and b and c are independently integers 0, 1, 2, 3, 4 or 5

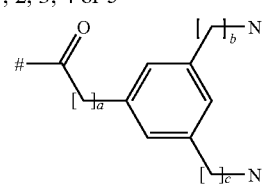

6

Analogue 7, having the structure below, where a is an integer 0, 1, 2, 3, 4 or 5; and b and c are independently integers 1, 2, 3, 4 or 5

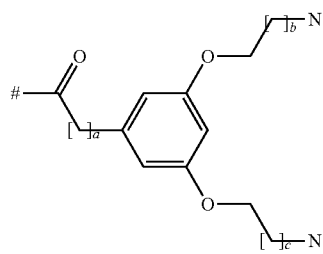

7

Analogue 8, having the structure below, where a is an integer 0, 1, 2, 3, 4 or 5; and b, c and d are independently integers 1, 2, 3, 4 or 5

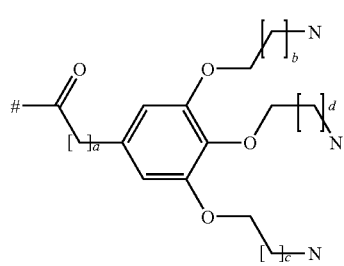

8

Analogue 9, having the structure below, where a is an integer 0, 1, 2, 3, 4 or 5; and b and c are independently integers 1, 2, 3, 4 or 5

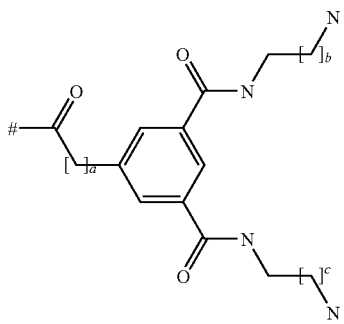

9

Furthermore, any methylene group of the building units may be replaced by a methyleneoxy ($CH_2$—O) or ethyleneoxy ($CH_2$—$CH_2$—O) group, provided that this does not result in the formation of a carbonate (—O—C(O)—O—) or carbamate (—O—C(O)—N—) moiety within the building unit.

In certain embodiments of the invention, the building units are selected from Lysine 1, Glycyl-Lysine 2 or Lysine analogue 5:

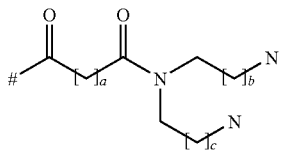

5 where a is an integer 0, 1 or 2 and further, any methylene group of 1, 2 or 5 may be replaced by a methyleneoxy or ethyleneoxy group provided that this does not result in the formation of a carbonate or carbamate moiety within the building unit.

Both the carboxylate group and the amine groups of the building units may be derivatised to enhance or diminish the reactivity of these groups. Reactable amine groups may be protected (deactivated) using amine-protecting groups such as Boc, CBz, 4-nitrobenzyloxycarbamate (4 $NO_2$—CBz) Fmoc, Dde, $CF_3CO_2$, 2-halo-CBz, Alloc, $Me_3SiEtSO_2$, Troc, o-$NO_2PhSO_2$ and 2,4-dinitrobenzene-sulfonyl groups.

In general, a free carboxyl group is not sufficiently reactive to react with an amine to form the amide bond, so some means is preferably provided that facilitates the dehydration and so drives the reaction to completion. This may be achieved, for example, by "activating" the carboxyl group as an acyl halide derivative or an activated ester derivative (The Peptides, Analysis, Synthesis and Biology Vol 1 Major Methods of Peptide Bond Formation; Academic Press New York 1979 eds Gross, E. and Meienhofer, J., Peptides: Chemistry and Biology. Wiley-VCH Weinheim 2002, Sewald, N. and Jakubke, H-D., The Chemical Synthesis of Peptides Clarendon Press, Oxford 1994, Jones, J.).

In the first activation method, the reagent which contains the carboxylic acid is reacted with a second reagent containing a hydroxyl moiety in the presence of a dehydrating reagent and, where required, other activating agents, to provide a product in which the acid containing moiety and the hydroxyl containing moiety are joined by an ester bond. This product is known as an "active ester". The reagent containing the hydroxyl moiety is chosen such that the product ester will readily react with primary amines to form amides with liberation of the aforementioned reagent containing the hydroxyl moiety. In some cases, the active ester is sufficiently stable to enable it to be isolated, purified and stored prior to use.

In a second activation method, the reagent which contains the carboxyl group may be reacted "in situ" with an activating agent to form an acyl species which further reacts with primary amines also present "in situ" or added after an appropriate prior activation time to lead to the formation of the required amide bond.

Both activation methods are described in more detail in PCT/AU2006/001591.

The lysine or lysine analogue building units of the dendritic motifs are reacted with a core compound. A core may be any compound containing three or more reactive (amino) nitrogens, one of which ultimately becomes the point of attachment for the first functional moiety (first amino nitrogen atom). It will be understood that this nitrogen atom can be protected by an appropriate protection group during construction of the dendrimer.

In certain embodiments of the invention, the core can be prepared by reacting one nitrogen atom of a diamino compound with lysine or a lysine analogue to form a triamino core compound. The unreacted amino group of the diamino compound can then become the amino group for attachment of the first functional moiety while the at least two amino groups of the lysine or lysine analogue become the points of attachment for the building units.

Diamino compounds suitable for reaction with lysine or lysine analogues, such as those exemplified herein, to prepare the core moieties include:

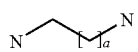

10 where a is an integer of 1 to 9, for example 1, 2, 3, 4 or 5;

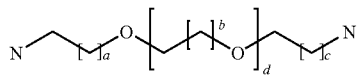

11 where a, b and c, are independently integers 1, 2, 3, 4 or 5, such as 2 or 3; and d is an integer from 0-100, such as 1-30; particularly 1-5, 6-10, 11-15, 16-20, 21-25 or 26-30;

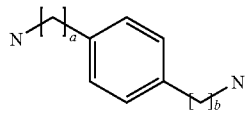

12 where a and b, are independently integers 0, 1, 2, 3, 4 or 5;

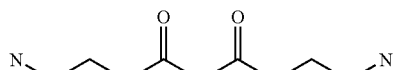

13 where a and c, are independently integers 1, 2, 3, 4, 5 or 6 and where b is an integer from 0, 1, 2, 3, 4, 5 or 6; and

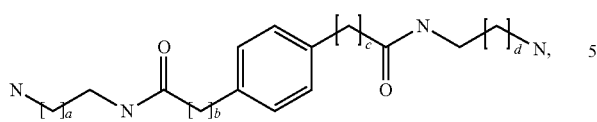

14 where a and d, are independently integers 1, 2, 3, 4, 5 or 6 and where b and c, are independently integers 0, 1, 2, 3, 4, 5 or 6.

Triamino compounds may be employed without further modification (i.e. reaction with lysine or a lysine analogue), or may be reacted with a lysine or lysine analogue to form a tetraamino core.

Examples of triamino compounds include:

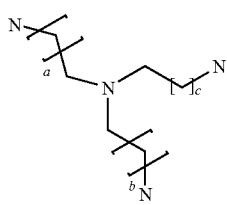

15 where a, b and c, are independently integers 1, 2, 3, 4, 5 or 6;

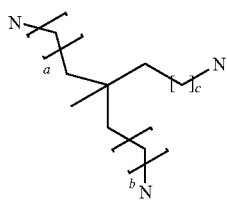

16 where a, b and c, are independently integers 0, 1, 2, 3, 4, 5 or 6;

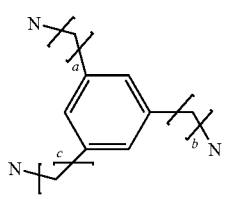

17

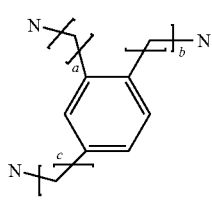

18

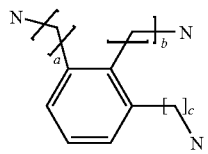

19 where a, b and c, are independently integers 0, 1, 2, 3, 4, 5 or 6;

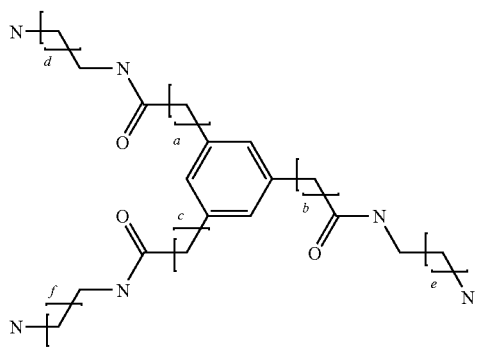

20 where a, b and c, are independently integers 0, 1, 2, 3, 4, 5 or 6; and d, e and f, are independently integers 1, 2, 3, 4, 5 or 6.

Tetramino compounds may be employed without further modification (i.e. reaction with lysine or a lysine analogue) or may be reacted with lysine or a lysine analogue to form a pentamino core. Examples of tetramino compounds include:

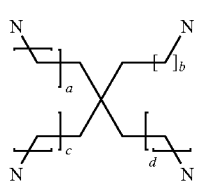

21

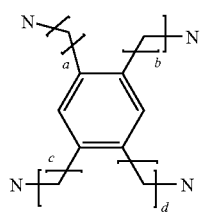

22 where a, b, c and d, are independently integers 0, 1, 2, 3, 4, 5 or 6

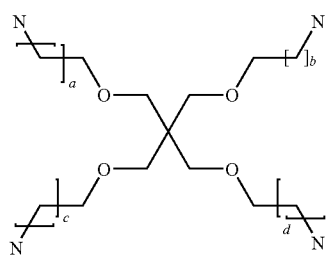

23 where a, b, c and d, are independently integers 1, 2, 3, 4, 5 or 6

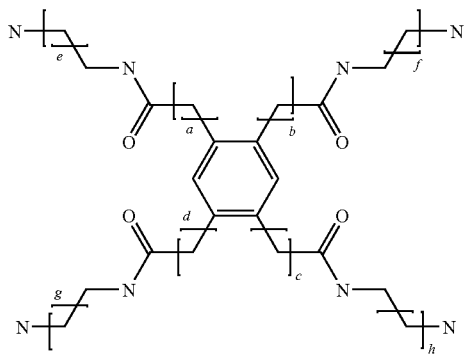

24 where a, b, c and d, are independently integers 0, 1, 2, 3, 4, 5 or 6; and e, f, g and h, are independently integers 1, 2, 3, 4, 5 or 6.

Furthermore, any methylene group of the core may be replaced by a methyleneoxy or ethyleneoxy group provided that this does not result in the formation of a carbonate or carbamate moiety within the core.

In certain embodiments, the core is a triamino compound resulting from reaction of lysine, or a lysine analogue, and a diamino compound selected from the following:

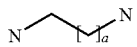

10 where a is an integer 1, 2, 3, 4 or 5;

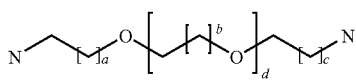

11 where a, b and c, are independently integers of 2 or 3 and d is an integer from 1-30;

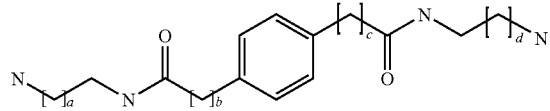

14 where a and d, are independently integers of 1 or 2 and where b and c, are independently integers from 0, 1 or 2.

In particular examples, the core is made up of a diamino compound, such as compound 11 where each of a, b, c and d are 1 (NEOEOEN) and lysine or a lysine analogue, for example, analogue 5, where each of a, b and c are 2 (Su(NPN)₂).

In other embodiments, the core is a triamino or tetramino compound selected from the following, either alone or as a reaction product with lysine or a lysine analogue:

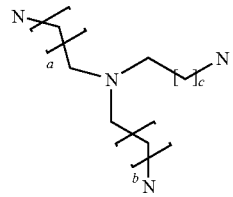

15 where a, b and c, which may be the same or different, are integers of 1 to 2;

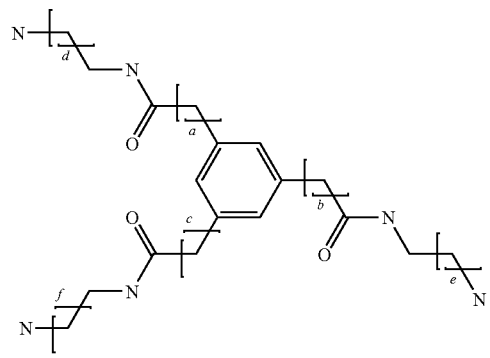

20 where a, b and c, are independently integers 0, 1 or 2; and d, e and f, are independently integers 1 or 2.

or a tetramine compound

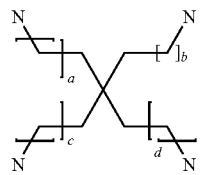

21 where a, b, c and d, are independently integers 0 or 1

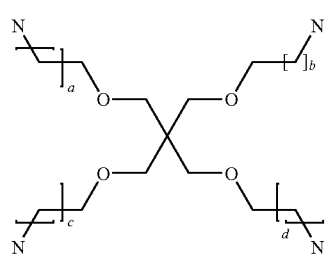

23 where a, b, c and d, are independently integers 1 or 2;

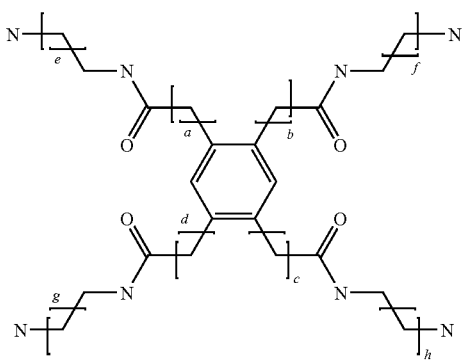

24 where a, b, c and d, are independently integers 0, 1 or 2; and e, f, g and h, are independently integers 1 or 2.

The preparation of lysine and lysine analogue dendrimer polymers is well known and is described by way of example in U.S. Pat. Nos. 4,289,872 and 4,410,688.

In general, the dendrimer has a core which retains a single reactive site that is preserved (by an appropriate protecting group) whilst the remaining amino sites of the core are utilised for the addition of building units. The protected reactive site of the core is ultimately used to attach a single entity (first functional moiety) to the core of the macromolecule.

In constructing the dendrimer, it is possible, through the use of amine-protecting groups, to only further react some of the surface amine groups of the building units in a layer or generation, for example by reacting only one of two available amino groups on a building unit, or only one or two of three available amino groups on a building unit, or alternatively, reacting all amino groups on only some of the surface building units, for example every second or third building unit, or two out of three building units. However, in certain embodiments of the invention, each amino group of a building unit in a particular layer or generation is further reacted with a lysine or lysine analogue building unit until the desired number of layers or generations has been constructed. In this manner, for example, when using building units which have two amino groups, the number of building units in a layer is double that of the immediate sub-layer and when using building units which have three amino groups, the number of building units in a layer is three times that of the immediate sub-layer.

The functional moieties comprise residues of a pharmaceutically active agent, a pharmacokinetic modifying agent, or an interacting agent, such as a targeting agent or a capture agent. The first and second functional moieties may be the same or different, and optionally the surface of the dendrimer may also carry one or more different additional functional moieties, e.g. third, fourth or fifth functional moieties. A functional moiety may be the residue of a single type of agent, e.g. pharmaceutically active agent, or may comprise two agents as a single entity, e.g. two pharmaceutically active agents attached or linked together or a pharmaceutically active agent attached or linked to a pharmacokinetic modifying agent or a pharmaceutically active agent attached or linked to a targeting agent. A functional moiety, when referred to as, for example, a second functional moiety, is taken to refer to a single type of functional moiety, e.g. each of the more than one second functional moieties are the same.

In some embodiments of the invention, a single type, or two three or four types of functional moiety are attached to all of the surface amino groups. In other embodiments only a portion of surface amino groups, for example those of alternating building units or one out of two surface groups per building unit or 1 or two out of three surface groups per building unit, have a functional moiety attached.

As used herein, a pharmaceutically active agent includes any molecule or precursor thereof, or residue thereof, which is capable of imparting a physiological effect or reaction after administration to a subject, either alone or in conjunction with another pharmaceutically active agent. The term also encompasses agents or residues thereof which in themselves may not impart a physiological effect or the desired level thereof, but in conjunction with one or more other pharmaceutical agents, or when attached to the dendrimer, provides the desired physiological activity. Pharmaceutically active agents contemplated herein may be naturally occurring, including modifications and derivatives of naturally occurring molecules, or may be synthetic and examples contemplated herein include small molecules, polymers, (non-dendritic and dendritic, where the dendritic moiety can have the same number of generations or a different number of generations to the macromolecule), saccharides, oligosaccharides, polysaccharides, amino acids, peptides, oligopeptides, polypeptides, proteins, glycoproteins, nucleic acids and nucleotides. Particular pharmaceutically active agents contemplated are intended for therapeutic or prophylactic applications. Examples of physiological effects or reactivity imparted by pharmaceutically active agents include depressing or stimulating biological reactions, for example through binding to a substrate, replacement or addition of substances, removal of deleterious substances and cellular death.

Protein-based drugs have been developed that provide significant clinical benefit to the patient, but in many cases these drugs require frequent dosing and large dose sizes. This is because the physio-chemical properties of the protein drugs lead to their rapid renal excretion or metabolic clearance. Advantageously, when attached to a dendrimer as described herein, the pharmacokinetic properties of the protein may be beneficially altered.

Thus, in certain examples of the invention, the pharmaceutically active agent(s) of the macromolecule may be amino acid based such as a protein, a glycoprotein, a peptide, oligopeptide, polypeptide or an enzyme or derivatives thereof.

The enzymes may be selected from carbohydrate specific enzymes, proteolytic enzymes, oxidoreductases, transferases, hydrolases, lyases, isomerases and ligases. Examples of enzymes include asparaginase, arginase, arginine deaminase, adenosine deaminase, superoxide dismutase, endotoxinases, catalases, chymotrypsin, lipases, uricases, adenosine diphosphatase, tyrosinases, and bilirubin oxidase. Carbohydrate-specific enzymes of interest include glucose oxidases, glycosidases, glucocerebrosidases, glucuronidases, etc.

Peptides and proteins that do not contain glycan moieties may be glycosylated either enzymatically using glycosyltransferases, or chemically synthesised, for example by using standard peptide chemistry and glycosylated amino acid components such as N-galactosylated asparagine. Alternatively glycosylation sites may be engineered into proteins or peptides which in vivo normally are produced in their non-glycosylated form.

Examples of proteins and peptides include haemoglobin, serum proteins such as blood factors including Factors VII, FX, FII, FV, protein C, protein S, tPA, PAI-1, tissue factor, FXI, FXII, and FXIII, as well as sequence FVIII, FIX variants thereof; immunoglobulins, cytokines such as interleukins, alpha-, beta-, and gamma-interferons, colony stimulating factors including granulocyte colony stimulating factors, platelet derived growth factors and phospholipase-activating protein (PUP). Other proteins and peptides include insulin, plant proteins such as lectins and ricins, tumor necrosis factors and related alleles, soluble forms of tumor necrosis factor receptors, interleukin receptors and soluble forms of interleukin receptors, growth factors such as tissue growth factors, such as TGFa's or TGFps and epidermal growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE, IgM, IgA, IgD and fragments thereof.

The pharmaceutically active agent of the macromolecule may alternatively, or in addition, include a water-insoluble pharmaceutical, a water-soluble pharmaceutical, a lipophilic pharmaceutical, or mixtures thereof.

The pharmaceutically active agent may be exemplified by, but not limited to one or more types selected from the groups in Table 1.

TABLE 1

Pharmaceutically active agents

| | |
|---|---|
| Acetonemia preparations | Anabolic agents |
| Anaesthetics | Analgesics |
| Anti-acid agents | Anti-arthritic agents |
| Antibodies | Anti-convulsants |
| Anti-fungals | Anti-histamines |
| Anti-infectives | Anti-inflammatories |
| Anti-metabolites | Anti-microbials |
| Anti-mitotics | Anti-parasitic agents |
| Anti-protozoals | Anti-ulcer agents |
| Antiviral pharmaceuticals | Behaviour modification drugs |
| Biologicals | Blood and blood substitutes |
| Bronchodilators and expectorants | Cancer therapy and related pharmaceuticals |
| Cardiovascular pharmaceuticals | Central nervous system pharmaceuticals |
| Diuretics | Contraceptives |
| Growth hormones | Diabetes therapies |
| Hematinics | Fertility pharmaceuticals |
| Hormone replacement therapies | Growth promoters |
| Immune suppressives | Hemostatics |
| Hormones and analogs | Immunostimulants |
| Minerals | Muscle relaxants |
| Nutraceuticals and nutritionals | Natural products |
| Ophthalmic pharmaceuticals | Obesity therapeutics |
| Pain therapeutics | Osteoporosis drugs |
| Proteins | Peptides and polypeptides |
| Retinoids | Respiratory pharmaceuticals |
| Sedatives and tranquilizers | Transplantation products |
| Urinary acidifiers | Steroids |
| Vitamins | Vaccines and adjuvants |

The present invention is particularly appropriate for pharmaceuticals that are very active even in extremely small quantities and whose sustained long-term administration is sought, particularly to overcome toxicity problems with standard doses. Non-limiting examples include paclitaxel and doxorubicin.

The macromolecules according to the present invention may be particularly useful in facilitating the passive targeting of drugs to sites of inflammation. This targeting is possible because of the increased permeability of vasculature associated with inflammation, to macromolecules and because of limited lymphatic drainage. Accordingly, in certain embodiments, the pharmaceutically active agent is an anti-inflammatory agent.

In one embodiment, the macromolecule according to the present invention includes two or more different pharmaceutically active agents, derivatives thereof, precursors thereof, or residues thereof, as functional moieties, either as separate moieties, or together in a single entity. The macromolecules according to this aspect of the present invention may therefore have application in combination therapy.

The pharmaceutically active agent may be an anti-tumor agent selected from one or more of the following: rituximab, oxaliplatin, docetaxel, gemcitabine, trastuzumab, irinotecan, paclitaxel, bevacizumab, carboplatin, cetuximab, doxorubicin, pemetrexed, epirubicin, bortezomib, topotecan, azacitidine, vinorelbine, mitoxantrone, fludarabine, doxorubicin, alemtuzumab, carmustine, ifosfamide, idarubicin, mitomycin, fluorouracil, cisplatin, methotrexate, melphalan, arsenic, denileukin diftitox, cytarabine, calcium levofolinate, cyclophosphamide, etoposide, viscum album, mesna, gemtuzumab, ozogamicin, busulfan, pentostatin, cladribine, bleomycin, daunorubicin, bendamustine, dacarbazine, raltitrexed, vincristine, fotemustine, etoposide phosphate, porfimer sodium and vinblastine.

The pharmaceutically active agents may be a combination of any two or more of the categories exemplified in Table 1 and/or anti-tumour agents listed above, either as a single entity where appropriate, or as separate functional moieties.

Exemplary combinations include, but are not limited to, combinations of: chemotherapeutic pharmaceuticals; anti-inflammatory pharmaceuticals and anti-arthritic pharmaceuticals; obesity therapeutics and diabetes therapeutics; growth hormones and growth promoters; muscle relaxants and anti-inflammatories; respiratory pharmaceuticals and bronchodilators or anti-microbials; chemotherapeutics and vitamins and the like.

Another group of pharmaceutically active agents contemplated herein are molecules or residues thereof which in themselves may not necessarily provide any desired or meaningful physiological activity but when attached to the surface or core of the dendrimer or when administered in combination (either separately, sequentially, or as an intimate composition) with one or more other pharmaceutically active agents, impart a physiological effect.

International Patent Application No. PCT/AU95/00350 (WO 95/34595) (the contents of which are incorporated herein by reference) describes a class of antiviral compounds comprising a dendrimer polymer having a plurality of surface groups, wherein at least one of the surface groups has an anionic- or cationic-containing moiety (or terminal group) bonded or linked thereto, particularly a sulfonic acid-containing, a carboxylic acid-containing, or a trimethylammonium-containing moiety. International Patent Application No. PCT/AU97/00447 (WO 98/03573) (the contents of which are incorporated herein by reference) describes the use of anionic- or cationic-containing dendrimer polymers in the prophylactic or therapeutic inhibition of angiogenesis in a human or non-human animal patient. The anionic- or cationic-containing moiety (or terminal group), which is linked or bonded to the surface groups of the dendrimer polymer include sulfonic acid-containing moieties, carboxylic acid-containing moieties, phosphoric or phosphonic acid-containing moieties, boronic acid-containing moieties, neuraminic or sialic acid-containing moieties or moieties containing neuraminic or sialic acid modified in the 4- or other position thereof.

Such anionic or cationic moieties (and their pharmaceutically acceptable salts) are contemplated herein as examples of pharmaceutically active agents. Two particular examples of such agents include —CO-3,5,-Ph($SO_3Na$)$_2$, COCH$_2$O-3,6-Naph($SO_3Na$)$_2$.

In some examples of the invention, the first functional moiety comprises a pharmaceutically active agent. In other examples, the second functional moiety comprises a pharmaceutically active agent. In yet further examples, the first functional moiety comprises a pharmaceutically active agent and the second functional moiety comprises a different pharmaceutically active agent. In yet other examples, the second and third functional moieties comprise pharmaceutically active agents.

A pharmacokinetic modifying agent includes any molecule or residue thereof which can modify or modulate the pharmacokinetic profile of a pharmaceutically active agent or the dendrimer bearing the pharmaceutically active agent, including that of absorption, distribution, metabolism and/or excretion. In a particular embodiment, the pharmacokinetic modifying agent is selected to prolong the plasma half-life of the pharmaceutically active agent or macromolecule.

In certain embodiments of the invention, at least one functional moiety is a pharmaceutically active agent and another functional moiety is a pharmacokinetic moiety.

The pharmacokinetic modifying agent may include polyfluorohydrocarbons, fatty acids, lipids, oligo- and poly-saccharides, deoxycholic acids (bile acids) or a polyethylene glycol (PEG), or polypropyleneglycol, and alkyl capped forms thereof, or polyethyloxazoline (e.g. PEOX) motif.

It is envisaged that the macromolecules of the invention will be particularly useful when the pharmaceutically active agent (such as a polypeptide or small molecule drug) is presented in combination with at least one pharmacokinetic modifying agent such as a PEG group. In one embodiment, a PEG molecule may be attached to the core, and the second functional moiety is a small molecule drug or polypeptide presented on the remaining surface of the macromolecule. Optionally, the second functional moiety may be a combination of small molecule drug and a further pharmacokinetic modifier moiety, either as a single functional moiety or discrete functional moieties.

The PEG groups may include relatively short ethylene glycol chains, for example PEG groups including one or more of the following

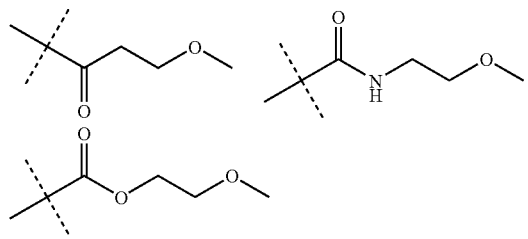

Alternatively the second functional moiety may include a poly-glutamic acid type structure. Poly-glutamic acid groups are preferred as they are generally well tolerated in vivo and are water soluble.

The percentage of PEG, polyethyloxazoline groups or polyglutamic acid groups and/or the size of the PEG, polyglutamic acid or polyethyloxazoline group may be modified and tailored to suit different pharmaceutically active agents.

Previous studies have suggested that after intravenous administration, uncapped $^3$H labelled poly-L-lysine macromolecules are rapidly metabolised to free lysine. However, it has surprisingly been established that PEGylation of the macromolecule reduces the recognition of the dendrimer by proteolytic enzymes as well as serum proteins and suppresses the phagocytic clearance, thereby prolonging plasma circulation times. Furthermore, PEGylation may increase the hydrodynamic volume of the macromolecule, thereby reducing the renal clearance rate.

For example, the present inventors have found that the plasma half-life and extent of urinary elimination of $^3$H labelled PEGylated lysine macromolecules is dependent on molecular weight. Larger PEGylated macromolecules (i.e. >30 kD) were relatively slowly cleared from the plasma into the urine compared with smaller dendrimers (i.e. <20 kD). This is despite the fact that the smaller macromolecule complexes showed signs of interaction with plasma components, leading to the creation of a higher molecular weight species. Elimination of these complexes was rapid and only intact macromolecule was recovered in the urine. It is therefore apparent that adding size by any means does not necessarily result in prolonged plasma life of the macromolecules. The larger macromolecules were found to accumulate in the liver and spleen. However this occurred over extended time periods and the amount that accumulated was less than 10% of the dose.

In a further preferred embodiment, wherein a first functional moiety is attached to the macromolecule, the PEG or PEOX, as second functional moieties, may constitute differing amounts relative to the first. Preferably the ratios of PEG or PEOX moieties to other functional moieties is in the range of 128:1 to 2:1, such as 64:1 to 4:1, and particularly 32:1 to 8:1.

In an embodiment wherein the PEG or PEOX functional moieties are attached at a selected point of attachment, the ratios of PEG or PEOX moieties to other functional moieties is preferably in the range of 1:2 to 1:128, more preferably 1:4 to 1:64, and most preferably 1:8 to 1:32.

The relative size of the individual PEG or PEOX groups may be reduced to reduce or eliminate interference with the pharmaceutically active agent.

In a preferred embodiment, the PEG groups are relatively monodisperse and chosen from a molecular weight range between 200 and 10,000 Daltons, more preferably the PEG groups are chosen from a molecular weight range between 300 and 5000 Daltons, and most preferably a molecular weight range between 500 and 3500 Dalton.

PEGylation may also improve the solubility of compounds and therefore may assist the solubility of an otherwise insoluble drug attached to the surface of the macromolecule.

Furthermore a pharmacokinetic modifying moiety may be incorporated in the macromolecule, to reduce non-specific binding. This may either be through an interacting moiety which increases the specificity of binding of a candidate to the moiety, or a moiety that is commonly referred to as having "anti-fouling" properties in that it minimises unwanted or non-specific binding. PEG is one such moiety, as has been herein described, which can, for example, decrease the recognition of the macromolecule by non-specific serum proteins.

The present invention thus provides a means by which drugs with high toxicity, or poor solubility, or both, may be engineered to provide a vehicle that will provide a controlled release of the drug to maintain a long term drug concentration at therapeutic, but not toxic, plasma levels.

The macromolecules according to the present invention may advantageously contain one or more functional moieties which can selectively interact, such as by binding or other association, with other molecules ("interacting"). The presence of such a functional moiety may therefore allow the macromolecule to be targeted or concentrated to a particular cell type or tissue type or to a protein (e.g. a receptor or enzyme), polysaccharide or DNA or RNA target, either in vivo or in vitro, or captured by another molecule to facilitate attachment of the macromolecule to a surface. Particular examples include lectins and antibodies and other ligands (including small molecules) for cell surface receptors. The interaction may occur through any type of bonding or association including covalent, ionic and hydrogen bonding, Van der Waals forces.

In one embodiment, the interacting agent is a peptide or polypeptide antibody. Advantageously, through its selective binding with its substrate, the antibody preferentially directs or concentrates the macromolecule to an appropriate in vivo or in vitro target, such as a cell surface receptor or polysaccharide, by binding to said target. Such a binding antibody is further referred to herein as "targeting agent".

In another embodiment, the interacting functional moiety is a non-peptide small molecule. Advantageously, the small molecule preferentially directs or concentrates the macromolecule to an appropriate in vivo or in vitro target, such as a receptor, or other small molecule, by interacting with said target. Such a small molecule is further referred to herein as a "capture agent".

The present invention is particularly appropriate for targeting of pharmaceutically active agents wherein the pharmaceutically active agent is a small drug molecule. Accordingly, in one embodiment, an interacting moiety may be attached to the core through the first amino nitrogen atom and the second functional moiety is a small molecule drug presented on the surface of the macromolecule. Optionally, the second functional moiety may be a combination of small molecule drug and a moiety that modified the pharmacokinetics of the small molecule drug and/or macromolecule, such as PEG, PEOX or poly-glutamic acid, either as discrete functional moieties, or a combined single type of functional moiety.

A number of different cell surface receptors are useful as targets for the binding and, preferably, enhanced uptake of macromolecules. In particular, receptors and their related ligands that are useful in the present invention include, but are not limited to, the folate receptor, adrenergic receptor, growth hormone receptor, luteinizing hormone receptor, estrogen receptor, epidermal growth factor receptor, fibroblast growth factor receptor (e.g. FGFR2), IL-2 receptor, CFTR and vascular epithelial growth factor (VEGF) receptor.

Folate is a vitamin that is essential for the biosynthesis of nucleotide bases and is therefore required in high amounts in proliferating cells. In cancer cells, this increased requirement for folic acid is frequently reflected in an overexpression of the folate receptor which is responsible for the transport of folate across the cell membrane. In contrast, the uptake of folate into normal cells is facilitated by the reduced folate carrier, rather than the folate receptor. The folate receptor is upregulated in many human cancers, including malignancies of the ovary, brain, kidney, breast, myeloid cells and the lung and the density of folate receptors on the cell surface appears to increase as the cancer develops.

The relative specificity of the folate receptor to tumour cells, and in particular to advanced stage tumour cells, mean that the folate receptor ligand, folate, may be a useful candidate for targeting chemotherapeutic drugs to tumours. The specificity of the folate receptor interaction with a folate receptor ligand-chemotherapeutic drug conjugate is further enhanced by the difference in the cell surface expression pattern of the folate receptor between certain non-transformed and malignantly transformed epithelial cells. In non-transformed cells, the folate receptor is preferentially expressed on the apical membrane surface of the cells, which faces the body cavity and is inaccessible to reagents present in the blood. However, upon transformation, the cell loses its polarity and the receptor can become accessible to drugs in the circulatory system that are targeted to the folate receptor.

Accordingly, folate or a folate derivative may be a useful binding (capture) moiety of the macromolecule of the present invention.

In some embodiments of the invention, the interacting moiety is a peptide or polypeptide in the form of an antibody (targeting agent), and is synthesised to have multiple adjacent histidine residues (poly-histidine motif) at either the N or C terminus, a cysteine tag, or a combination thereof, to facilitate the reaction with the deprotected dendrimer.

Targeting peptides and antibodies may be expressed fused to an N or C terminal, preferably N terminal, poly-histidine motif. The terminal poly-histidine motif may be utilised to conjugate the targeting peptide to the dendrimer of the contrast agent of the invention through a Nickel complex, wherein the Nickel ions are present as surface groups on the dendrimer or on the ends of linkers extending from the dendrimer, in complex with nitrilotriacetic acid moieties. Alternatively, the poly-histidine motif may be utilised for one-step purification using Nickel affinity resins and optionally removed from the purified molecule by the inclusion of an enterokinase or endopeptidase cleavage recognition site. Such purification methods will be known to the skilled person.

More preferably the targeting polypeptide or antibody may be expressed fused to a N or C terminal, preferably N terminal, cysteine tail. Cysteine contains a highly nucleophilic thiol group which may be utilised in the presence of thiol-specific reactive groups, such as chloro, bromo or iodoacetamide groups or the maleimide moiety to form a thioether linkage; or in disulfide exchange reactions with reactive disulfide moieties such as the 2-pyridinedithio moiety to form disulfide bonds; in either case leading to the ligation of the targeting polypeptide or antibody to the dendrimer. These thiol reactive groups would be provided in the dendrimer material through reaction of appropriate derivatising agents such as activated haloacetic acids or maleimide derivatives of glycine or 3-aminopropionic acid, or activated 3-(2-pyridinedithio)propionic acid, with one or more selectively deprotected surface amines of the macromolecule.

The targeting polypeptide or antibody may also be expressed with a combination of cysteine and histidine tails. The cysteine and histidine tail may either be expressed, each at the opposite end to the other, (e.g. N terminal cysteine tail and a C terminal histidine tail), or both at the N or C terminal.

The macromolecule may further be utilised in various applications to modify the surface of a device where the ability of the modified device to capture or bind a particular molecule, cell or tissue type, or a protein, DNA or RNA target, or to modify the non-specific biological interactions thereof, is advantageous. The presentation of an appropriate interacting agent may provide a more efficient, reproducible means of attaching the macromolecule to the surface of a component of a diagnostic or medical device, in use. In turn, the component of the device will have more reproducible properties because of the defined and controlled nature of macromolecule.

The interacting agent may be one of: a reactive chemical moiety, a chelate for a transition metal or a ligand partner of a high affinity ligand-receptor pair, exemplified by biotin-streptavidin or digoxin-"Anti-digoxin Antibody" (Mudgett-Hunter M, Margolies M N, Ju A, Haber E. *J Immunol.* 1982; 129:1165-1172).

Exemplary dendrimers and macromolecules contemplated herein may be conveniently represented according to the following formula:

[First Functional Moiety]Core[Building Unit]$_m$[Second Functional Moiety]$_p$[Third Functional Moiety]$_q$ wherein:
the core, building units and functional moieties are as described herein;

m represents the sum of the building units (including the subsurface and surface layers) of the macromolecule. By way of example, where each layer comprises building units having 2 amino groups, m is an integer between 2 and 32, for example 2, 4, 8, 16 or 32;

p represents the number of second functional moieties attached to amino nitrogen atoms at the surface (outermost) layer of building units. By way of example, where each layer comprises building units having 2 amino groups, p may be an integer from 1 to 64 (for example 2, 4, 8, 16, 32 or 64); and q represents the number of third functional moieties attached to amino nitrogen atoms at the surface (outermost) layer of building units. By way of example, where each layer comprises building units having 2 amino groups, q may be an integer from 0 to 63 such that p and q is no greater than 64.

Particular combinations of functional moieties contemplated by the invention are presented in the Table below:

| $1^{st}$ Functional Moiety | $2^{nd}$ Functional Moiety | $3^{rd}$ Functional Moiety |
|---|---|---|
| Interacting agent | Pharmaceutically active agent | — |
| Interacting agent | Pharmacokinetic modifying agent | — |
| Interacting agent | Pharmacokinetic modifying agent | Pharmaceutically active agent |
| Pharmaceutically active agent (e.g. protein) | Pharmaceutically active agent (e.g. drug) | — |
| Pharmaceutically active agent | Pharmacokinetic modifying agent | — |
| Pharmaceutically active agent (e.g. protein) | Pharmacokinetic modifying agent | Pharmaceutically active agent (e.g. drug) |
| Pharmacokinetic modifying agent | Pharmaceutically active agent | — |
| Pharmacokinetic modifying agent | Interacting agent | — |
| Pharmacokinetic modifying agent | Interacting agent | Pharmaceutically active agent |

As described above, the functional moieties may be attached to the macromolecule at a selected site of attachment either directly or via a cleavable or non-cleavable linker.

The term "linker" refers herein to any chemical entity which serves to link the functional moieties to the surface or core amino atom. Exemplary linkers contemplated by the present invention include polymers such as polyethylene glycol (PEG), polypropylene glycol, polyaryls, peptides, alkyl and alkenyl chains, and saccharides (mono, oligo and poly).

In particular embodiments, the linker comprises a PEG chain, such as from 1-100 ethyleneoxy repeat units, for example from 2-20 or 20-40 repeat units.

Long chain PEG-based groups may be utilised as linker moieties. For example, PEG-peptides may be used in a similar way to conventional peptides, except the PEG moiety provides additional in vivo stability and mass for the carrier. Typically, it is used to conjugate drug to antibody carriers and has the advantage of increasing the distance between antibody and drug while exposing the site of enzymatic cleavage, decrease immunogenicity of the conjugate, increase blood circulation times and increasing the solubility of the complex. Following internalisation of the conjugate and enzymatic release of the active drug (which is not necessarily released as free drug) antiproliferative effects have been observed for Adriamycin and a Duocarmycin derivative.

Where linker moieties are used to connect functional moieties to the core or surface amine of the macromolecules, the reaction between the linker and the functional moiety may be carried out either before, or after, the linker moiety is reacted with the appropriate amine of the dendrimer.

Thus, a linker may be used in a number of ways to attach a first functional moiety to the core. In a first method, the linker may be attached to the core and the first functional moiety is attached to the linker. Alternatively, the linker may be first attached to the functional moiety and then attached to the core. In a third method, both the core and the functional moiety can be attached to a linker or linker component and the two linker moieties subsequently reacted together to provide the linker moiety between the core and the first functional moiety.

Similarly, a linker may be used in various ways to attach a second (or third or fourth) functional moiety to the surface of the dendrimer. The linker may be attached to the surface amino nitrogen atom of the dendrimer and the second (or third or fourth) functional moiety then attached to the linker. Alternatively, the linker may be first attached to the functional moiety, and then attached to the surface amino nitrogen atom. As above, a linker moiety or component thereof can be attached to both the surface amino nitrogen atom and the second (or third or fourth) functional moiety, and the two linkers or components subsequently reacted to provide a linker moiety between the surface and functional moiety.

In addition, linker moieties may be incorporated into the synthesis of the macromolecule according to the present invention, for example between building units. As described above, the linker may be attached to either the surface amino nitrogen atoms, the building unit forming the next layer or both, to ultimately provide a linker between building units.

A reaction which is used to introduce one or more linker moieties onto a dendrimer or dendritic motif (either at the surface or core) is conducted to ensure the complete reaction of all deprotected surface amines of a macromolecule with the linker moieties. Typically this is done by using an excess of the chosen linker moiety.

The linker may be reacted with the deprotected dendritic motif or macromolecule prior to reaction of the linker with the functional moiety. In a further embodiment, the linker attached to the macromolecule may in turn bear a protecting group that requires deprotection to enable reaction with the functional moiety.

Preferably, the amine protecting groups are selected from the group including Boc, CBz, 4-nitrobenzyloxycarbamate (4-$NO_2$—CBz) Fmoc, Dde, $CF_3CO_2$, 2-halo-CBz, Alloc, $Me_3SiEtSO_2$, Troc, o-$NO_2PhSO_2$ and 2,4-dinitrobenzenesulfonyl groups, and preferably from Boc, CBz, 4-nitrobenzyloxycarbamate (4-$NO_2$—CBz), Fmoc 2-halo-CBz, Aloc and $Me_3SiEtSO_2$.

The linker may be cleavable or non cleavable, depending on the requirements of the functional moiety(s) attached. Cleavable linkers may be designed to be enzymatically cleaved, and may for example, be used in macromolecules targeted to tissues expressing those enzymes. Alternatively, an acid labile linker may be preferred such that the compound attached to it is released under acid conditions, such as in hypoxic tissue.

The linker moiety may include repeating units selected to stiffen the backbone thereof, or may be partially cross-linked to stiffen the backbone.

The linker is made cleavable or non-cleavable by the presence of an appropriate stable or labile group in the linker. Examples of suitable cleavable and non-cleavable groups in a linker include:

| Linker type | Summary |
| --- | --- |
| Amide | Generally used as stable linkers. |
| Hydrazone | Acid labile linkers that are mostly stable at physiological pH have been shown to inhibit the growth of some tumour cells after hydrolysis of the bond to release an anti-tumour drug. |
| Oxime | Acid labile linkers that are mostly stable at physiological pH have been shown to inhibit the growth of some tumour cells after hydrolysis of the bond to release an anti-tumour drug. |
| Imine | Acid labile linkers that are mostly stable at physiological pH have been shown to inhibit the growth of some tumour cells after hydrolysis of the bond to release an anti-tumour drug. |
| Ester | The cleavability of esters are strongly related to their structure and number or cleavable sites, where monoesters are more stable that diesters. In general, esters are less stable than amide bonds and more stable than disulfide bonds. Cleavage of orthoesters is dependent on acidic pH. |
| Peptide | A large number of peptide bonds have been investigated as generally non specific enzyme cleavable linkers. Their stability depends largely on the molecules they are attached to and the sequence. |
| disulfide | One of the most unstable linkers available and shows poor stability in circulation. Generally used to facilitate rapid metabolism of toxic •species/carriers in target organs. |
| thymidine | While this has not previously been used as a metabolisable linker, thymidine phosphorylase is over expressed in many solid tumours and catalyses the phosphoralytic cleavage of thymidine to thymine and deoxyridose-1-phosphate. | i) Amide Linkers

The nature of an amide bond is important in determining whether the free drug will be released from a conjugate. For instance, conjugation of a drug (e.g. doxorubicin) to a carrier via an amide bond produces a conjugate that is hydrolytically stable and which does not exert any anticancer effects in vitro. A drug bound directly to a carrier via an amide bond will also not be readily cleaved as a free drug, but rather as a drug-amino acid if the carrier is itself degradable. The release of free drug from carriers bound via a direct amide linker will only be achievable in rare circumstances where the drug is itself a peptide-like molecule and the bond between drug and carrier is enzymatically cleavable.

ii) Hydrazone, Oxime and Imine Linkers

Hydrazone, oxime and imine bonds do not require the presence of enzymes to allow cleavage of the drug from the carrier. They are able to be cleaved hydrolytically at the C=N bond in low pH environments such as in the tumour extravascular space or within lysosomes. Commonly used hydrazone, oxime and imine linkers arise from the reaction of a hydrazine, alkoxyamine or amine moieties, respectively, of a linker with a carbonyl (ketone or aldehyde) of a pharmaceutically active moiety. The link may also be modified to slow the rate of hydrolysis by modifying the number of alkyl groups surrounding the C=N bond moiety, or by substitution with electron withdrawing (to increase acid lability) or electron donating (to decrease acid lability) moieties.

iii) Ester Linkers

Both acid labile and metabolisable ester linkers can be made. Orthoesters have been used to conjugate PEG to lipids which bind anionic membrane carriers. The stability of the conjugate in acidic conditions (pH 4-6) depends on the structure of the ester or orthoester linker. In general, α-methoxy-ω-{N-(2-octadecyloxy-[1,3]dioxolan-4-yl)methylamido}-polyethyleneglycol$_{110}$ shows good stability at both pH 4 and 5, α-methoxy-ω-{N-(2-cholesteryloxy-[1,3]dioxolan-4-yl) methylamido}-polyethyleneglycol$_{110}$ is very stable at pH 5 but moderately less stable at pH 4, α-methoxy-ω-{N-(2-methyl-s-octadecyloxy-[1,3]dioxan-5-yl)-amido}-polyethyleneglycol$_{110}$ and α-methoxy-ω-{N-2-(3-hydroxypropyl-cholesterylcarbamate)-2-methyl-[1,3]dioxan-5-yl-amido}-polyethyleneglycol$_{110}$ are not stable. In terms of simple ester conjugation to small molecules, diester functionalities provide more sites for metabolic cleavage compared with monoesters which are more stable than disulfides but less stable than amide bonds.

iv) Peptide Linkers

Peptide linkers are by far the most versatile of all cleavable linkers in that many different combinations of amino acids can be used to control the rate of cleavage and the cleavage enzyme. However, these linkers have two problems associated with their use as conjugates for drug and carrier, 1) they are generally cleavable by non specific peptidases throughout the body and may therefore result in non-specific drug toxicity at non-tumour distribution sites and 2) cleavage may occur at a site within the linker that results in an amino acid remaining bound to the drug molecule. This may hinder the chemotherapeutic effect of the drug molecule. Alternatively, the bound amino acid may not alter the pharmacological effects of the drug but may affect its pharmacokinetics. However, these cleavage effects may be controlled by choosing an appropriate amino acid in the peptide linker that is bound directly to the drug molecule, e.g. proline.

Generally, cathepsin B cleavable linkers have been designed to be cleaved following endocytosis of the drug conjugate via the lysosome system, as cathepsin is located in lysosomes and not free in the cytosol. Endocytosis is generally initiated following binding of the carrier (which is usually an antibody directed against a cancer specific cell surface receptor or ligand for a cancer specific cell surface receptor) to the cell membrane.

Non-specific proteases (i.e. proteases that are not specific for a particular peptide sequence) may cleave a drug from a PEGylated macromolecule after it has undergone sufficient extravasation and accumulation in tumour tissue.

The following guidelines about the rate of peptide cleavage apply, where a>b indicates that the rate of cleavage of a is greater than the rate of cleavage for b. For peptide sequences used as linkers between an active pharmaceutical and the dendrimer terminal nitrogens: terminal Cys>no terminal Cys Gly>terminal Gly=terminal, Gly Phe Gly>terminal GlyGlyGly and terminal GlyGlyGlyPhe=terminal GlyProGly.

Note: CysGly bonds are reduced by GSH. GlyGlyGly bonds are generally very stable relative to other peptide bonds. The cleavage of dipeptides is generally specific to particular proteases and may be controlled based on the expression of various proteases contained within tumour cells.

v) Disulfide Linkers

Disulfide linkers are the most unstable linkers currently used and undergo rapid reductive cleavage in vitro. Their in vivo stability is generally higher, however, than their in vitro stability. They may be formed via disulfide linkages between sulphur containing amino acids or at non peptide based disulfide bonds. They also show greater reactivity with other nucleophilic thiols in the body and hence show rapid plasma clearance.

General Summary of Linker Cleavability

In circulation, the order of linker cleavabilities is as follows:
Disulfide>long chained peptides>esters>hydrazones tetrapeptides (GlyGlyGlyPhe—SEQ ID NO. 1)=tripeptides (GlyPheGly>GlyGlyGly=GlyProGly).apprxeq. or >dipeptides (AlaVal, AlaPro, GlyPro, PheLeu, Val-Cys) >glutaraldehyde=amide.

The stability of various linkers is based on the groups to which they are conjugated (i.e. accessibility of the enzymes to the linker), the behaviour of the conjugate at the site of required activity (i.e. cellular uptake or extracellular accumulation) and the nature of the conjugate (i.e. ester vs. amide). The in vivo behaviour of the disulfide conjugates with the current system is expected to be relatively unpredictable. While long chained peptides are more easily assessed by proteases for rapid cleavage, they may be cleaved too rapidly and at non specific sites, resulting in release of a pharmaceutical active-peptide/amino acid species which may not be biologically active.

Cleavage of a C=N based linker (hydrazone, oxime or imine), ester or peptide conjugates will occur at least over several days which allows the conjugates to accumulate in tumour tissue. Each has its advantages, but ester or hydrazone linkers may be preferred. An ester bond linking a pharmaceutical active to the macromolecule provides a bond that is rapidly cleaved, and though this may not be specific to the target site, cleavage results in the release of free a pharmaceutical active. Hydrazone bonds produce conjugates are more stable in the general circulation than esters and are cleaved with greater specificity at the tumour site via hydrolysis at the C=N bond. However, the pharmaceutical active molecule may need to be modified to allow hydrazone formation either by incorporation of a carbonyl or hydrazine moiety.

In some embodiments, the linker moiety may include two reactive groups, F' and Y', which are connected by one or more carbons or heteroatoms, preferably by a hydrocarbon backbone. The reactive group F' may be activated to react with reactive amine moieties like those on the core, or the surface or subsurface layer of the dendritic motif. Typically the reactive group F' is a carboxylate group or residue thereof. The other functional moiety, Y', is either an amine comprising a protecting group, or it is selected such that it has a specific reactivity that is complementary to a reactive group of a desired functional moiety that is to be attached to the core, or the surface layer or subsurface layer of a dendritic motif. Typical examples of Y' include amine, hydroxyl, thiol, alkenyl or alkynyl, nitrile, halide, carboxylate or azido groups.

In addition to the linkers described above, photocleavable linkers may be used with the present invention. For example, heterobifunctional, photocleavable linkers may be used. Heterobifunctional, photocleavable linkers may be either water or organic soluble. They contain an activated ester that may react with amines or alcohols and an epoxide that may react with a thiol group. Between the ester and epoxide groups is a 3,4-dimethoxy-6-nitrophenyl photoisomerisation group, which, when exposed to near-ultraviolet light (365 nm), releases the amine or alcohol in intact form. Thus, the pharmaceutically active component, when linked to the macromolecule using such linkers, may be released in biologically active or activatable form through exposure of the target area to near-ultraviolet light.

In further embodiments, preparation of the macromolecule may further include the step of modifying the amine group and/or linker and/or functional moiety to facilitate ligation of the functional moiety to the amine, either directly or via the cleavable or non-cleavable linker.

Thus, the amine group at the surface or core of the macromolecule can be modified by a modifier group to facilitate attachment to the linker or functional moiety. Alternatively, or in addition, the linker may be modified to facilitate attachment to the surface or core amine group.

The terminus of the linker for attachment to the functional moiety may be modified by a modifier group to facilitate attachment to the functional moiety. Alternatively, or in addition, the functional group may be modified by a modifier group to facilitate attachment to the linker or directly to the surface or core amine group.

In a particular embodiment, the first amino nitrogen atom of the core and/or a linker used to attach the first functional moiety and/or the first functional moiety is further modified to facilitate attachment of the first functional moiety to the core.

The amino (surface or core) moiety and/or linker and/or functional moiety may be modified to allow for the ligation either of the functional moiety, to the amino atom, via the linker by derivatisation with a group that includes a chemical moiety selected from: a haloacetamide, a maleimide or other thiol reactive moiety, a reactable thiol or exchangeable disulfide moiety, an aliphatic or aromatic aldehyde, a ketone, an alkoxyamine, a hydrazine, an azide, an alkyne, an oligohistidine array and any peptide array, a nitilotriacetic acid group, any carboxylate or reactive residue thereof (such as activated esters); any chemical moiety capable of reacting with an organic halide such as an organostannyl group, an acrylate, a boronic acid (or ester) and organic alkynes via metal catalysed coupling reactions, namely Stille, Heck, Suzuki and Sonogashira respectively, any moiety capable of enzymatic ligation (e.g. through the use of a transglutaminase), any moiety capable of native chemical ligation. Methods for derivatisation to incorporate the modifier are known in the art.

More preferably, the chemical modifier may be selected from the following
(i) Maleimide

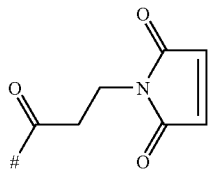

(ii) Haloacetamide (X=Cl, Br, I)

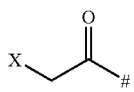

(iii) Hydrazide

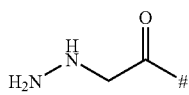

(iv) Alkoxyamine

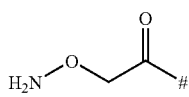

(v) 3-(2-Pyridyldithiothio)propionate

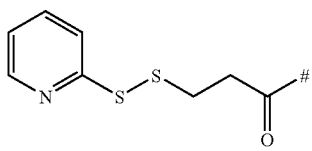

In certain embodiments, the surface or core amine may be modified to allow for the ligation of the functional moiety by derivatisation with a group that includes a chemical moiety selected from: haloacetamide, maleimide or other thiol reactive moiety, a reactable thiol or exchangeable disulfide moiety, aldehyde, ketone, an alkoxyamine moiety, hydrazine, azide, alkyne, oligohistidine array, nitrilotriacetic acid motif.

In a preferred method, the protecting group of the selected amine, such as the core amine, is removed, and the amine is reacted with a haloacetic acid derivative, or a maleimide derivative such as 3-maleimidopropionic acid or 4-maleimidobutyric acid under conditions where the amide bond is formed. General methods for the coupling of thiol containing peptides and proteins to such thiol active groups are described in Hermanson, G. T. Bioconjugate Techniques (Academic Press 1996) and the references cited therein.

General methods for the covalent coupling of macromolecules to molecules such as peptides and antibodies are within the level of skill in the art. Such methods are described in Hermanson, G. T. Bioconjugate Techniques (Academic Press 1996) and the references cited therein, Blatter et al, *Biochem.*, 24: 1517 (1985) and Jue et al, *Biochem.*, 17:5399 (1978). Methods for the ligation of peptides or proteins containing adjacent histidine residues with macromolecules or solid supports containing the nitrilotriacetic acid motif through complexation with nickel are described in Hochuli et al *J. Chromatogr.* 1987 411 177, Sigal et al *Anal. Chem.* 1996 68 490 and Gershon et al *J. Immunol. Meth.* 1995 183 65. The references cited above are incorporated herein by reference in their entirety.

The macromolecules of the invention may be prepared by a divergent or convergent dendrimer synthesis. Methods for divergent and convergent syntheses are known in the art. In one embodiment, the macromolecule is constructed via a divergent synthesis, wherein the last (surface) layer of building units added may have optionally protected amino groups and/or bear amino groups which have the functional moieties already attached or are modified with a modifier and/or bear a linker moiety for subsequent attachment of a functional moiety.

Alternatively, in a convergent synthesis, dendritic motifs, or wedge, comprising more than a single building unit, can be attached to the core or surface amino groups of a dendrimer. Again, the surface amino groups of a dendritic motif may be optionally protected and/or may already have one or more functional groups attached, and/or are modified with a modifier and/or bear a liker moiety for the functional moiety.

In another aspect the invention also contemplates compositions comprising a macromolecule as described herein together with a pharmaceutically acceptable excipient, carrier or adjuvant thereof.

The invention further provides for the use of macromolecules as described herein in therapy.

Subjects to be treated include mammalian subjects: humans, primates, livestock animals (including cows, horses, sheep, pigs and goats), companion animals (including dogs, cats, rabbits, guinea pigs), and captive wild animals. Laboratory animals such as rabbits, mice, rats, guinea pigs and hamsters are also contemplated as they may provide a convenient test system. Non-mammalian species such as birds, amphibians and fish may also be contemplated in certain embodiments of the invention.

In certain embodiments, the macromolecules according to the invention, when administered according to the desired dosing regimen, at least partially attain a desired therapeutic or prophylactic effect, including one or more of: alleviating the symptoms of, preventing or delaying the onset of, inhibiting the progression of, or halting or reversing altogether the onset or progression of the particular disorder or condition being treated.

The active ingredient may be administered in a single dose or a series of doses. While it is possible for the active ingredient to be administered alone, it is preferable to present it as a composition, preferably as a pharmaceutical composition, with one or more pharmaceutically acceptable adjuvants.

The formulation of such compositions is well known to those skilled in the art, see for example, *Remington's Pharmaceutical Sciences*, 18th Edition, Mack Publishing, 1990. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier must be pharmaceutically acceptable in the sense of being compatible with the other ingredients of the composition and not injurious to the subject. Compositions include those suitable for oral, rectal, nasal, topical (including dermal, buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent), preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Devices for transdermal delivery, such as patches, may also be used to administer the compounds of the invention.

Compositions for rectal administration may be presented as a suppository with a suitable base comprising, for example, cocoa butter, glycerin, gelatin or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Pharmaceutical compositions of this invention can be administered to mammals including humans in a manner similar to other therapeutic agents in treatment-effective amounts. A treatment effective amount is intended to include an amount which, when administered according to the desired dosing regimen, at least partially attains the desired therapeutic or prophylactic effect, as above. The dosage to be administered, and the mode of administration, will depend on a variety of factors including age, weight, sex, condition of the patient and genetic factors, and will ultimately be decided by medical personnel subsequent to experimental determinations of varying dosage followed by imaging as described herein. In general, dosage required for diagnostic sensitivity or therapeutic efficacy will range from about 0.001 to 50,000 µg/kg, preferably between 0.01 to 25.0 µg/kg of host body mass. The optimal dose will be determined empirically following the disclosure herein.

It will be understood that the functional moieties, particularly pharmaceutically active agents, may be present as pharmaceutically acceptable salts or prodrugs. The term "prodrug" is used in its broadest sense and encompasses those derivatives that are converted in vivo, either enzymatically or hydrolytically, to the compounds of the invention. Such derivatives would readily occur to those skilled in the art, and include, for example, compounds where a free thiol or hydroxy group is converted into an ester, such as an acetate, or thioester or where a free amino group is converted into an amide. Procedures for acylating the compounds of the invention, for example to prepare ester and amide prodrugs, are well known in the art and may include treatment of the compound with an appropriate carboxylic acid, anhydride or chloride in the presence of a suitable catalyst or base. Esters of carboxylic acid (carboxy) groups are also contemplated. Suitable esters $C_{1-6}$ alkyl esters; $C_{1-6}$ alkoxymethyl esters, for example methoxymethyl or ethoxymethyl; $C_{1-6}$alkanoyloxymethyl esters, for example, pivaloyloxymethyl; phthalidyl esters; $C_{3-8}$cycloalkoxycarbonyl$C_{1-6}$alkyl esters, for example, 1-cyclohexylcarbonyloxyethyl; 1,3-dioxolen-2-onylmethyl esters, for example, 5-methyl-1,3-dioxolen-2-onylmethyl; and $C_{1-6}$alkoxycarbonyloxyethyl esters, for example, 1-methoxycarbonyloxyethyl. Prodrugs of amino functional groups include amides (see, for example, *Adv. BioSci.*, 1979, 20, 369, Kyncl, J. et al), enamines (see, for example, *J. Pharm. Sci.*, 1971, 60, 1810, Caldwell, H. et al), Schiff bases (see, for example, U.S. Pat. No 2,923,661 and *Antimicrob. Agents Chemother.*, 1981, 19, 1004, Smyth, R. et al), oxazolidines (see, for example, *J. Pharm. Sci*, 1983, 72, 1294, Johansen, M. et al), Mannich bases (see, for example, *J. Pharm. Sci*. 1980, 69, 44, Bundgaard, H. et al and *J. Am. Chem. Soc.*, 1959, 81, 1198, Gottstein, W. et al), hydroxymethyl derivatives (see, for example, *J. Pharm. Sci*, 1981, 70, 855, Bansal, P. et al) and N-(acyloxy)alkyl derivatives and carbamates (see, for example, *J. Med. Chem.*, 1980, 23, 469, Bodor, N. et al, *J. Med. Chem.*, 1984, 27, 1037, Firestone, R. et al, *J. Med. Chem.*, 1967, 10, 960, Kreiger, M. et al, U.S. Pat. No 5,684,018 and *J. Med. Chem.*, 1988, 31, 318-322, Alexander, J. et al). Other conventional procedures for the selection and preparation of suitable prodrugs are known in the art and are described, for example, in WO 00/23419; *Design of Prodrugs*, H. Bundgaard, Ed., Elsevier Science Publishers, 1985; *Methods in Enzymology*, 42: 309-396, K. Widder, Ed, Academic Press, 1985; *A Textbook of Drug Design and Development*, Krogsgaard-Larsen and H. Bundgaard, Eds, Chapter 5, p 113-191 (1991); *Advanced Drug Delivery Reviews*, 8; 1-38 (1992); *Journal of Pharmaceutical Sciences*, 77; 285 (1988), H. Bundgaard, et al; *Chem Pharm Bull*, 32692 (1984), N. Kakeya et al and *The Organic Chemistry of Drug Desig and Drug Action*, Chapter 8, pp 352-401, Academic press, Inc., 1992.

Suitable pharmaceutically acceptable salts include, but are not limited to salts of pharmaceutically acceptable inorganic acids such as hydrochloric, sulphuric, phosphoric nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic, fendizoic, 4-4'-methylenebis-3-hydroxy-2-naphthoic acid, o-(p-hydroxybenzoyl)benzoic, 4'-4"-dihydroxytriphenylmethane-2-carboxylic acid and valeric acids. Base salts include, but are not limited to, those formed with pharmaceutically acceptable cations, such as sodium, potassium, lithium, calcium, magnesium, ammonium and alkylammonium. Basic nitrogen-containing groups may be quaternised with such agents as lower alkyl halide, such as methyl, ethyl, propyl, and butyl chlorides, bromides and iodides or dialkyl sulfates such as dimethyl and diethyl sulfate.

It will be understood that the invention disclosed and defined in this specification extends to all alternative combinations of two or more of the individual features mentioned or evident from the text or drawings. All of these different combinations constitute various alternative aspects of the invention.

The present invention will now be more fully described with reference to the accompanying examples. It should be understood, however, that the description following is illustrative only and should not be taken in any way as a restriction on the generality of the invention described above.

EXAMPLES

The invention will now be described with reference to the following non-limiting illustrative examples and figures.

A system of nomenclature has been developed for the purposes of identifying the individual compounds described in this patent. This nomenclature is used to simplify the description of the compounds and is used in place of what would be a complex IUPAC name, the use of which may be prone to error and difficult to interpret.

The macromolecule nomenclature makes use of the following abbreviations:

| Abbreviation | Name | Structure[1] |
| --- | --- | --- |
| NEOEOEN | 2-[2-(2-aminoethoxy)ethoxy]-ethylamine | |
| [CBz] NEOEOEN | Benzyloxycarbonylamino-3,6-oxa-8-aminooctane | |
| [Boc] NEOEOEN | t-butoxycarbonylamino-3,6-oxa-8-aminooctane | |

| Abbreviation | Name | Structure[1] |
|---|---|---|
| Su(NPN)₂ | | 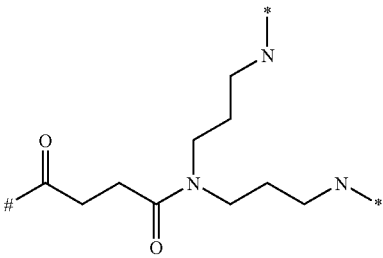 |
| Lys | Lysine | 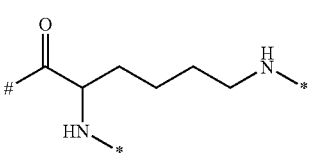 |
| DBL-OPNP | p-nitrophenyl active ester of di-Boc Lysine | 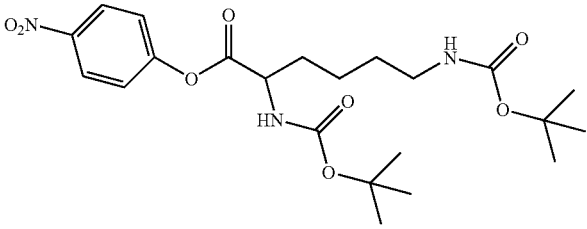 [SMILES: CC(C)(C)OC(=O)NCCCCC(NC(=O)OC(C)(C)C)C(=O)Oc1ccc([N+](=O)[O-])cc1] |
| NH₂•TFA | Represents the surface amine groups of the deprotected molecule as the TFA salt | |
| Boc | t-butyloxycarbonyl | 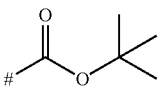 |
| CBz | Benzyloxycarbonyl | 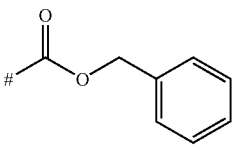 |
| p-NO₂—CBz | p-nitro-benzyloxycarbonyl | 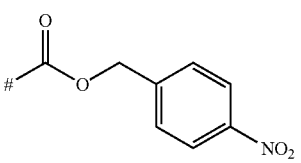 |
| COCH₂O-3,6-Naph(SO₃Na)₂ | 1-carboxy-3,6-naphthyldisulfonic acid di-sodium salt | 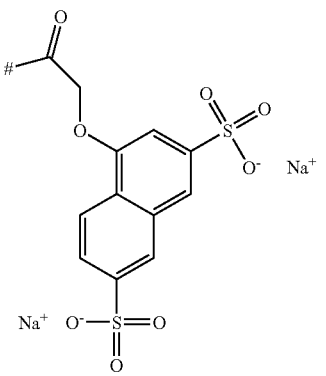 |

| Abbreviation | Name | Structure[1] |
|---|---|---|
| CO-4-Ph(SO3Na) | 1-carboxy-4-phenylsulfonic acid di-sodium salt | (structure: benzoyl group with para-sulfonate sodium salt) |
| (NPN)₂ [CBz]₂ | | (structure: bis-CBz protected dipropylenetriamine) |
| (NPN)₂ [Boc]₂ | | (structure: bis-Boc protected dipropylenetriamine) |
| HO—Su(NPN)₂ [CBz]₂ | | (structure: bis-CBz protected dipropylenetriamine with succinic acid on central N) |
| HO—Su(NPN)₂ [Boc]₂ | | (structure: bis-Boc protected dipropylenetriamine with succinic acid on central N) |
| PNPO-Su(NPN)₂ [CBz]₂ | | (structure: bis-CBz protected dipropylenetriamine with succinate p-nitrophenyl ester on central N) |

| Abbreviation | Name | Structure[1] |
|---|---|---|
| PNPO—Su(NPN)₂ [Boc]₂ | | 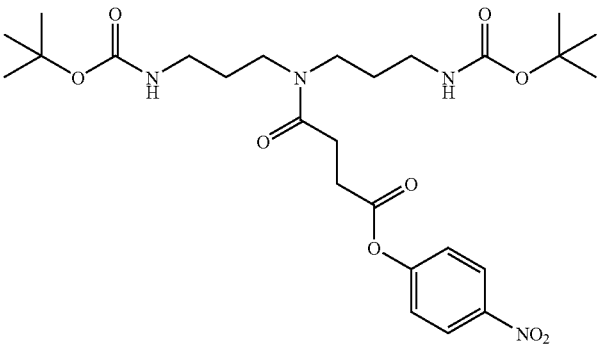 [SMILES: CC(C)(C)OC(=O)NCCCN(CCCNC(=O)OC(C)(C)C)C(=O)CCC(=O)Oc1ccc([N+](=O)[O-])cc1] |
| MeOGly•HCl | | 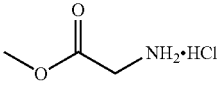 |
| PNPO-α-Boc-ε-CBz-Lys | | 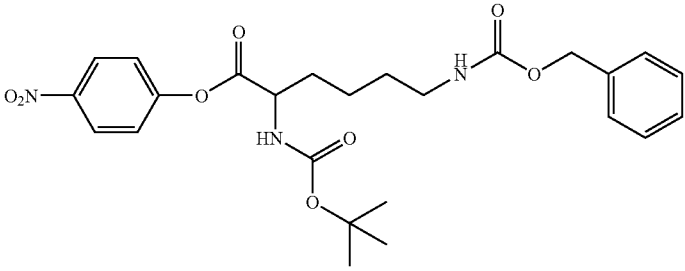 [SMILES: CC(C)(C)OC(=O)NC(CCCCNC(=O)OCc1ccccc1)C(=O)Oc1ccc([N+](=O)[O-])cc1] |
| biotin-NHS ester | | 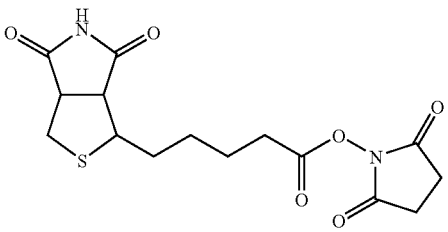 [SMILES: O=C(CCCCC1SCC2C(=O)NC(=O)C12)ON1C(=O)CCC1=O] |

Further abbreviations are as follows:

| Abbreviation | Full Name |
|---|---|
| PyBop | Benzotriazole-1-yl-oxy-tris-pyrrolidino-phosphonium hexafluorophosphate |
| DIPEA | N,N-Diisopropylethylamine |
| TEA | Triethylamine |
| DCC | 1,3-Dicyclohexylcarbodiimide |
| HOBt | 1-Hydroxybenzotriazole hydrate |
| DMAP | 4-(Dimethylamino)pyridine |
| NHS | N-hydroxysuccinimide |
| TFA | Trifluoroacetic acid |
| DCM | Dichloromethane |
| EtOAc | Ethyl acetate |
| MeOH | Methanol |
| MeCN | Acetonitrile |
| DMF | Dimethylformamide |
| DMSO | Dimethylsulfoxide |
| PBS | Phosphate buffered saline |
| TLC | Thin Layer Chromatography |
| HPLC | High Performance Liquid Chromatography |
| MS | Mass Spectrometry |
| MTX | Methotrexate |
| THF | tetrahydrofuran |

HPLC and MS equipment details:

HPLC—Waters 2795 with 2996 Diode Array Detector (DAD)

MS—Waters ZQ4000 with ESI probe, inlet flow split to give around 50 μL/min to the MS.

Mass Spectra data was acquired in positive or negative electrospray ionisation mode as indicated. The raw data was deconvoluted using a Maximum Entropy algorithm (MaxEnt) as implemented in MassLynx software v4.0, supplied by Waters Corporation. The data reported in the experimental details corresponds to the observed value after deconvolution to a theoretical zero charge state. All PEG reagents were obtained from commercial sources and used as received.

Example 1

β-Lactoglobulin-MAL-$(CH_2)_2$CONH-$PEG_{1100}$-CO-NEOEOEN [Su(NPN)$_2$] [Lys]$_{16}$ [PEG$_{570}$]$_{32}$ i. Benzyloxycarbonylamino-3,6-oxa-8-aminooctane: [CBz] NEOEOEN

To a solution of 2,2'-(ethylenedioxy)diethylamine (4.45 g, 30 mmol) and TEA (0.7 mL, 50 mmol) in MeCN (50 mL), was added dropwise over 20 min a solution of N-(benzyloxy-carbonyloxy)succinimide (1.2 g, 5.0 mmol) in MeCN (10 mL). Once the addition was complete the solution was stirred at room temperature overnight. MeCN was removed in vacuo and the resulting colourless residue redissolved in water (50 mL). The aqueous solution was washed with DCM (3×25 mL) and the combined organic extracts reduced in vacuo. The residue was dissolved in 2M HCl (25 mL) and washed with diethyl ether (3×25 mL). The aqueous layer was then neutralized to pH 7 with NaOH and evaporated to dryness in vacuo. The resulting residue was added to EtOAc (25 mL), filtered and dried over $Na_2SO_4$. Removal of solvent in vacuo provided a colourless oil (840 mg, 2.9 mmol, 60%). ESI MS (+ve) 283 [M+H]$^+$; calc. m/z for $C_{14}H_{22}N_2O_4$ [M+H]$^+$: 283.34.

ii. tert-Butyl 2-({2-[(tert-butoxycarbonyl)amino]propyl}amino)propylcarbamate A solution of dipropylenetriamine (171 g, 1.32 mol) in THF (200 mL) was added dropwise over 1 h to a solution of tert-butyl-1H-imidazole-1-carboxylate (444 g, 2.64 mol) in THF (1.2 L) at room temperature. The resulting solution was refluxed for 4 h and then stirred at room temperature overnight. The THF was removed in vacuo and the residue dissolved in DCM (2 L). The DCM solution was first washed with NaOH (2M, 2×1 L) and then citric acid 10% w/v (2×1 L). The aqueous citric acid solution was basified with NaOH (4 M, until pH 14), extracted with DCM (3×600 mL) and the combined DCM extracts concentrated in vacuo to afford a clear oil, which solidified on cooling to yield a white solid (346 g, 80%).

iii. HO-Su(NPN)$_2$ [Boc]$_2$

A 3 L vessel fitted with an overhead stirrer was charged with tert-Butyl 2-({2-[(tert-butoxycarbonyl)amino]propyl}amino)propylcarbamate (208.5 g, 0.63 mol) and toluene (900 mL). Succinic anhydride (63 g, 0.63 mol) was added in one portion and the resulting solution heated at 60° C. overnight. The mixture was cooled to room temperature, diethyl ether was added (1×200 mL) and the solid filtered. The solid was washed with diethyl ether (2×200 mL) and dried to yield a white solid (230 g, 91%).

iv. [CBz] NEOEOEN [Su(NPN)$_2$] [Boc]$_2$

To a solution of [CBz] NEOEOEN (Example 1i) (440 mg, 1.6 mmol) in DMF (4 mL), was added TEA (0.22 mL, 1.6 mmol) and PNPO-Su(NPN)$_2$-Boc$_2$ (950 mg, 1.8 mmol). The solution was stirred at room temperature overnight. Solvent was removed in vacuo and the residue dissolved in EtOAc (250 mL). This solution was washed with brine (125 mL), 1M $Na_2CO_3$ (3×50 mL), water (125 mL), 1M KHSO$_4$ and a second wash of brine (125 mL) before drying over $Na_2SO_4$. The solution was concentrated in vacuo and purified by silica gel chromatography (MeOH/DCM gradient) to provide a clear viscous oil (165 mg, 0.23 mmol, 15%). ESI MS (+ve) 496 [M+H]$^+$; calc. ink for $C_{24}H_{41}N_5O_6$ [M+H]$^+$: 496.61.

v. [CBz] NEOEOEN [Su(NPN)$_2$] [NH$_2$.TFA]$_2$

[CBz] NEOEOEN [Su(NPN)$_2$] [Boc]$_2$ (13.89 g, 20.0 mmol) was dissolved in acetic acid (50 mL) and the stirred solution cooled in an ice bath. Ice cooled TFA (50 mL, 0.73 mol) was added at a rate that maintained the temperature of the solution at or below 5° C. The ice bath was removed and the solution stirred at room temperature for 5 h. It was then cooled and ice-cooled water (100 mL) was added at a rate that kept the mixture below 5° C. The volatiles were evaporated in vacuo and water (100 mL) was added to the oily residue. The solution was then concentrated in vacuo and the process was repeated with more water (2×100 mL). The oil was dissolved in water (50 mL), the solution filtered and freeze dried to give [CBz] NEOEOEN [Su(NPN)$_2$] [NH$_2$.TFA]$_2$ (17.1 g) as a colourless glassy solid. $^1$H-NMR (300 MHz, CD$_3$OD) δ (ppm) 1.90 (apparent quintet, J=6.6 Hz, 2H); 1.99 (m, 2H); 2.57 (m, 2H); 2.65 (m, 2H); 2.89 (t, J=6.6 Hz, 2H); 3.00 (t, J=7.5 Hz, 2H); 3.30-3.38 (complex, 6H); 3.42-3.58 (complex, 6H); 3.61 (s, 4H); 5.08 (s, 2H); 7.25-7.40 (complex, 5H); HPLC (Hydrophilic/TFA) Rt=8.0 min; ESI MS (+ve) 496.2 [M+H]$^+$; calc. m/z for $C_{24}H_{42}N_5O_6^+$ [M+H]$^+$: 496.3.

vi. [CBz] NEOEOEN [Su(NPN)$_2$] [Lys]$_2$ [Boc]$_4$

A solution of DBL-OPNP (12.8 g, 17.7 mmol) in DMF (80 mL) was added to a solution of [CBz] NEOEOEN [Su(NPN)$_2$] [NH$_2$.TFA]$_2$ (19.5 g, 35.4 mmol) and TEA (17.9 g, 0.177 mol) in DMF (80 mL) at room temperature. After stirring for 16 h, a solution of glycine (1.50 g, 29.0 mmol) in water (50 mL) was added and stirring continued for 16 h. Volatiles were removed in vacuo, the residue dissolved in EtOAc (200 mL) and the solution washed sequentially with 5% w/v $Na_2CO_3$ (10×50 mL), brine (50 mL), 1M HCl (2×50 mL) and again with brine (50 mL). The EtOAc solution was dried ($Na_2SO_4$), filtered and the solvent removed in vacuo to give the product as a colourless oil (20.74 g). $^1$H-NMR (300 MHz, CD$_3$OD) δ (ppm) 1.15-1.95 (complex, 16H); 1.43 (s, 18H); 1.44 (s, 18H); 2.51 (m, 2H); 2.64 (m, 2H); 3.02 (t, J 6.6 Hz, 4H); 3.17 (m, 2H); 3.25-3.45 (complex, 8H); 3.48-3.58 (complex, 4H); 3.61 (s, 4H); 5.08 (s, 2H); 7.25-7.40 (complex, 5H). HPLC (Hydrophobic/TFA) Rt=8.6 min; ESI MS (+ve) 1153.0 [M+H]$^+$; calc. m/z for $C_{56}H_{98}N_9O_{16}^+$ [M+H]$^+$: 1152.7.

vii. [CBz] NEOEOEN [Su(NPN)$_2$] [Lys]$_2$ [NH$_2$.TFA]$_4$

[CBz] NEOEOEN [Su(NPN)$_2$] [Lys]$_2$ [Boc]$_4$ (20.74 g, 18.0 mmol) was dissolved in acetic acid (50 mL) and the stirred solution cooled in an ice bath. Ice cooled TFA (50 mL, 0.73 mol) was added at a rate that maintained the temperature of the solution at or below 5° C. The ice bath was removed and the solution stirred at room temperature for 5 h. The solution was then cooled to 5° C. and added to ice-cold water (100 mL) at a rate that kept the mixture below 5° C. Volatiles were evaporated in vacuo and water (100 mL) was added to the residual oil. The resultant solution was then concentrated in vacuo and the process was repeated with more water (2×100 mL). The oil was dissolved in water (50 mL), the solution filtered and freeze dried to give [CBz] NEOEOEN [Su(NPN)$_2$] [Lys]$_2$ [NH$_2$.TFA]$_4$ (25.1 g) as a pale yellow glassy solid. $^1$H-NMR (300 MHz, D$_2$O) δ (ppm) 1.44 (m, 4H); 1.70 (m, 6H); 1.86 (m, 6H); 2.50 (m, 2H); 2.64 (m, 2H); 2.99 (t, J=7.2 Hz, 2H); 3.12-3.47 (complex, 12H); 3.52-3.63 (complex, 12H); 3.95 (m, 2H); 5.12 (s, 2H); 7.32-7.50 (complex, 5H); HPLC (Hydrophilic/TFA) Rt=10.4 min; ESI MS (+ve) 752.4 [M+H]$^+$; calc. m/z for $C_{36}H_{66}N_9O_8^+$ [M+H]$^+$: 752.5.

viii. [CBz] NEOEOEN [Su(NPN)$_2$] [Lys]$_4$ [Boc]$_8$

A solution of DBL-OPNP (16.8 g, 13.9 mmol) in DMF (100 mL) was added to a solution of [CBz] NEOEOEN [Su(NPN)$_2$] [Lys]$_2$ [NH$_2$.TFA]$_4$ (33.98 g, 61.3 mmol) and TEA (13.5 g, 0.134 mol) in DMF (100 mL) at room temperature. After stirring for 11 h, a 1M aqueous solution of glycine (10 mL) was added; the same quantity of glycine solution was added again after 1 h and again 1.5 h later. Stirring was continued for a further 2 h and volatiles were then evaporated in vacuo. The residue was dissolved in EtOAc (200 mL) and the solution washed sequentially with 0.5 M HCl (2×50 mL), 10% w/v Na$_2$CO$_3$ (6×50 mL) and brine (50 mL). The EtOAc solution was dried (Na$_2$SO$_4$), filtered and the solvent removed in vacuo to give the desired product as a colourless oil (26.26 g, 91%). $^1$H-NMR (300 MHz, d$_6$-DMSO) δ (ppm) 1.00-1.75 (complex, 112H); 2.32 (m, 2H); 2.47 (m, 2H); 2.75-3.50 (complex, 32H); 3.75-3.90 (complex, 4H); 4.10-4.25 (complex, 2H); 5.01 (s, 2H); 6.38 (br, m, 1H); 6.60-6.95 (complex, 8H); 7.25 (m, 1H); 7.28-7.39 (complex, 5H); 7.60-8.05 (complex, 7H). HPLC (Hydrophobic/TFA) Rt=15.2 min; ESI MS (+ve) 1033.8 [M+2H]$^{2+}$/2; calc. m/z for $C_{100}H_{179}N_{17}O_{28}^{2+}$ [M+2H]$^{2+}$/2: 1033.7.

ix. [CBz] NEOEOEN [Su(NPN)$_2$] [Lys]$_4$ [NH$_2$.TFA]$_8$

[CBz] NEOEOEN [Su(NPN)$_2$] [Lys]$_4$ [Boc]$_8$ (24.52 g, 11.9 mmol) was dissolved in acetic acid (108 mL) and the stirred solution cooled in an ice bath until the acetic acid began to freeze. TFA (108 mL, 1.40 mol) was then added at a rate that maintained the temperature of the solution at or below 10° C. The ice bath was then removed and the solution stirred at room temperature for 15 h. The acetic acid and TFA were evaporated in vacuo and water (100 mL) was added to the residual oil. The solution was then concentrated in vacuo and the process was repeated with more water (3×100 mL). The resultant oil was dissolved in water (100 mL), the solution filtered and then freeze dried to give [CBz] NEOEOEN [Su(NPN)$_2$] [Lys]$_4$ [NH$_2$.TFA]$_8$ (29.2 g) as a colourless glassy solid. $^1$H-NMR (300 MHz, D$_2$O) δ (ppm) 1.25-2.05 (complex, 40H); 2.53 (m, 2H); 2.65 (m, 2H); 2.95-3.10 (complex, 8H); 3.10-3.45 (complex, 16H); 3.55-3.75 (complex, 8H); 3.95 (t, J=6.6 Hz, 2H); 4.06 (t, J 6.6 Hz, 2H); 4.20-4.30 (complex, 2H); 5.15 (s, 2H); 7.35-7.55 (complex, 5H); HPLC (Hydrophilic/Formate) Rt=8.4 min; ESI MS (+ve) 1265.1 [M+H]$^+$, 633.0 [M+2H]$^{2+}$/2; calc. m/z for $C_{60}H_{114}N_{17}O_{12}^+$ [M+H]$^+$: 1264.9, calc. m/z for $C_{60}H_{115}N_{17}O_{12}^{2+}$ [M+2H]$^{2+}$: 633.0.

x. [CBz] NEOEOEN [Su(NPN)$_2$] [Lys]$_8$ [Boc]$_{16}$

A solution of DBL-OPNP (48.2 g, 87.2 mmol) in DMF (120 mL) was added to a solution of [CBz] NEOEOEN [Su(NPN)$_2$] [Lys]$_4$ [NH$_2$.TFA]$_8$ (25.83 g, 11.87 mmol) and TEA (23.1 g, 0.228 mol) in DMF (150 mL) at room temperature. After stirring for 19 h, a solution of glycine (3.27 g, 43.6 mmol) in water (80 mL) was added. Stirring continued for 2 h and then the volatiles were evaporated in vacuo. The residue was dissolved in EtOAc (200 mL) and the solution washed sequentially with 5% w/v Na$_2$CO$_3$ (1×100 mL; 4×50 mL), 1M HCl (2×50 mL) and again with brine (50 mL). The EtOAc solution was dried (Na$_2$SO$_4$), hot filtered and the solvent removed in vacuo to give the desired product as a yellow glassy solid (27.12 g, 59%). Some of the product precipitated in the fluted filter paper; dissolution of this material in methanol, filtration and removal of methanol in vacuo gave additional product (9.02 g, 20%) as a yellow foam. Analysis of both portions of the product gave identical sets of $^1$H-NMR and ESI MS data. $^1$H-NMR (300 MHz, CD$_3$OD) δ (ppm) 1.00-1.75 (complex, 232H); 2.51 (m, 2H); 2.65 (m, 2H); 2.75-3.50 (complex, 40H); 3.50-3.65 (complex, 8H); 3.90-4.50 (complex, 14H); 5.08 (s, 2H); 7.25-7.40 (complex, 5H). HPLC (Hydrophobic/TFA) Rt=19.7 min; ESI MS (+ve) 1947.3 [M+2H]$^{2+}$/2, 1298.3 [M+3H]$^{3+}$/3; calc. m/z for $C_{188}H_{339}N_{33}O_{52}^{2+}$ [M+2H]$^{2+}$/2: 1946.8, calc. m/z for $C_{188}H_{340}N_{33}O_{52}^{3+}$ [M+3H]$^{3+}$/3: 1298.2.

xi. [CBz] NEOEOEN [Su(NPN)$_2$] [Lys]$_8$ [NH$_2$.TFA]$_{16}$

[CBz] NEOEOEN [Su(NPN)$_2$] [Lys]$_8$ [Boc]$_{16}$ (25.75 g, 6.62 mmol) was dissolved in acetic acid (122 mL) and the stirred solution cooled in an ice bath until the acetic acid began to freeze. The ice bath was removed and TFA was carefully added until the acetic acid just melted. The stirred solution was once again placed in the ice bath and the remainder of the TFA (total amount of TFA used was 108 mL, 1.40 mol) was then added at a rate that maintained the temperature of the solution at or below 10° C. The ice bath was removed and the solution stirred at room temperature for 17 h. The solution was cooled on ice and then added to ice cold water (400 mL) while making sure that the temperature of the resultant solution remained below 10° C. The volatile components were evaporated in vacuo and water (250 mL) was added to the oily residue. The solution was then concentrated in vacuo and the process was repeated with more water (2×250 mL). The final oil was dissolved in water (200 mL), the solution filtered and freeze dried to give [CBz] NEOEOEN [Su(NPN)$_2$] [Lys]$_8$ [NH$_2$.TFA]$_{16}$ (27.6 g) as a colourless glassy solid. $^1$H-NMR (300 MHz, D$_2$O) δ (ppm) 1.25-1.65 (complex, 40H); 1.65-2.05 (complex, 48H); 2.50 (m, 2H); 2.62 (m, 2H); 2.95-3.05 (complex, 16H); 3.05-3.45 (complex, 24H); 3.55-3.70 (complex, 8H); 3.94 (t, J 6.6 Hz, 4H); 4.05 (t, J 6.6 Hz, 4H); 4.15-4.30 (complex, 4H); 4.30-4.40 (complex, 2H); 5.13 (s, 2H); 7.35-7.50 (complex, 5H); HPLC (Hydrophilic/TFA) Rt=8.9 min; ESI MS (+ve) 763.9 [M+3H]$^{3+}$/3, 573.4 [M+4H]$^{4+}$/4; calc. m/z for $C_{108}H_{212}N_{33}O_{20}^{3+}$ [M+3H]$^{3+}$: 764.2, calc. m/z for $C_{108}H_{213}N_{33}O_{20}^{4+}$ [M+4H]$^{4+}$: 573.4.

xii. [CBz] NEOEOEN [Su(NPN)$_2$] [Lys]$_{16}$ [Boc]$_{32}$

DBL-OPNP (27.66 g, 59.2 mmol) was added in ca. 2-3 g portions to a solution of [CBz] NEOEOEN [Su(NPN)$_2$] [Lys]$_8$ [NH$_2$.TFA]$_{16}$ (13.83 g, 3.36 mmol) and TEA (13.1 g, 0.129 mol) in DMF (150 mL) at room temperature. After stirring for 17 h, a solution of glycine (2.22 g, 29.6 mmol) in water (50 mL) was added. Stirring was continued for 3 h and the solution was then added to rapidly stirred water (400 mL). The supernatant liquid was decanted from the resultant precipitated gum. The gummy material was dissolved in DMF (100 mL) and the solution added slowly to a well stirred mixture of flaked ice (500 g) and water (500 mL). The precipitated white solid was collected by filtration, resuspended in 5% w/v Na$_2$CO$_3$, sonicated and filtered again. The solid was washed thoroughly with water (4×100 mL) and dried to give the desired product (22.10 g, 87%) as a beige powder. $^1$H-NMR (300 MHz, CD$_3$OD) δ (ppm) 1.10-1.95 (complex, 472H); 2.52 (m, 2H); 2.65 (m, 2H); 2.95-3.10 (complex, 30H); 3.10-3.30 (complex, 30H); 3.30-3.45 (complex, 12H); 3.45-3.65 (complex, 8H); 3.80-4.15 (complex, 16H); 4.20-4.45 (complex, 14H); 5.09 (s, 2H); 7.25-7.40 (complex, 5H). Due to insolubility in the HPLC mobile phase, HPLC and ESI MS data for this product could not be obtained. Instead, the BOC groups were removed and these data were obtained from the derived poly trifluoroacetate salt.

xiii. [NH$_2$] EOEOEN [Su(NPN)$_2$] [Lys]$_{16}$ [Boc]$_{32}$

Ammonium formate (6 mg, 95 mol) and 10% w/w palladium on activated carbon (28 mg) were added to a solution of [CBz] NEOEOEN [Su(NPN)$_2$] [Lys]$_{16}$ [Boc]$_{32}$ (348 mg, 46.13 mol) in DMF (4.5 mL) and water (0.5 mL). The mixture was stirred under nitrogen for 16 h and then passed through a 0.54 μm filter. The solution was concentrated in vacuo then dissolved in methanol and concentrated in vacuo again to give [NH$_2$] EOEOEN [Su(NPN)$_2$] [Lys]$_{16}$ [Boc]$_{32}$ as a glassy solid (433 mg). $^1$H-NMR (300 MHz, CD$_3$OD) δ (ppm) 1.10-1.90 (complex, 474H); 2.52 (m, 4H); 2.67 (m, 4H); 2.95-3.45 (complex, 80H); 3.55 (m, 8H); 3.63 (s, 8H); 3.85-4.50 (complex, 28H). HPLC (sample not soluble in LC compatible solvents). Absence of CBz signals in $^1$H-NMR confirmed formation of product.

xiv. [p-NO$_2$-CBz] NEOEOEN [Su(NPN)$_2$] [Lys]$_{16}$ [Boc]$_{32}$

To a solution of [NH$_2$] EOEOEN [Su(NPN)$_2$] [Lys]$_{16}$ [Boc]$_{32}$ (287 mg, 0.038 mmol) in DMF (3 mL) was added DIPEA (20 uL, 0.116 mmol) followed by 4-nitrobenzyl chloroformate (12 mg) with stirring. The solution was stirred at room temperature, under nitrogen for 16 h. The volatiles were removed in vacuo to give the desired product (294 mg). TLC (10% MeOH/DCM) confirmed reaction was complete. $^1$H-NMR (300 MHz, CD$_3$OD) δ (ppm) 1.10-1.90 (complex, 474H); 2.52 (m, 4H); 2.67 (m, 4H); 2.95-3.45 (complex, 80H); 3.55 (m, 8H); 3.63 (s, 8H); 3.85-4.50 (complex, 28H); 7.55 (d, 2H); 8.25 (d, 2H). HPLC (sample not soluble in LC compatible solvents).

xv. [p-NO$_2$-CBz] NEOEOEN [Su(NPN)$_2$] [Lys]$_{16}$ [NH$_2$.TFA]$_{32}$

To a stirred solution of [p-NO$_2$-CBz] NEOEOEN [Su(NPN)$_2$] [Lys]$_{16}$ [Boc]$_{32}$ (294 mg, 0.038 mmol) in DCM (4 mL) was added TFA (1 mL) at room temperature. The solution was stirred at room temperature for 16 h. The volatiles were removed in vacuo and to the residue dissolved in 1:1 MeCN/H$_2$O (5 mL). The solvents were removed in vacuo. This process was repeated twice. The residue was triturated with diethyl ether (20 mL) and the solvent removed by decanting. The residue was dried in vacuo to give the product as a white foam (354 mg). HPLC (Hydrophilic/TFA) Rt=5.59 min; ESI MS (+ve) 4386 [M+H$^+$]; calc. m/z for C$_{204}$H$_{399}$N$_{66}$O$_{38}^+$[M]$^+$: 4384.77.

xvi. [p-NO$_2$-CBz] NEOEOEN [Su(NPN)$_2$] [Lys]$_{16}$ [PEG$_{570}$]$_{32}$

To a stirred solution of m-dPEG$_{570}$-NHS (1.24 g, 1.805 mmol) in DMF (0.5 mL) was added a solution of [p-NO$_2$-CBz] EOEOEN [Su(NPN)$_2$] [Lys]$_{16}$ [NH$_2$.TFA]$_{32}$ (410.4 mg, 0.052 mmol) and TEA (572 μL, 4.103 mmol) in DMF (0.5 mL) dropwise. The solution was stirred at room temperature, under nitrogen for 16 h. Volatiles were removed in vacuo and the residue was taken up into 50 mL water and purification was performed by tangential flow filtration on a Centramate (10 KDa membrane, 100 mL sample reservoir). The retentate was reduced to dryness to yield the desired product as an oily residue (906 mg, 78%). HPLC (Hydrophilic/TFA) Rt=10.76 min. $^1$H-NMR (300 MHz, CD$_3$OD) δ (ppm) 1.10-1.90 (complex, Lys(3×CH$_2$), 184H); 2.20-2.70 (complex, Lys (N—CH$_2$), 64H); 3.0-3.20 (complex, 58H); 3.35 (s, PEG-OMe, 96H); 3.40-3.90 (complex, PEG-CH$_2$, 1536H); 4.10-4.40 (broad s, 36H); 7.60 (d, J=8.38 Hz, ArH, 2H); 8.20 (d, J=8.33 Hz, ArH, 2H).

xvii. [NH$_2$] EOEOEN [Su(NPN)$_2$] [Lys]$_{16}$ [PEG$_{570}$]$_{32}$

This reaction was performed in the same way as Example 1xiii; using [p-NO$_2$-CBz] EOEOEN [Su(NPN)$_2$] [Lys]$_{16}$ [PEG$_{570}$]$_{32}$ (347 mg, 0.0153 mmol) with ammonium formate (68 mg, 1.08 mmol), 10% w/w palladium on activated carbon (320 mg) in DMF (6.4 mL) and water (0.6 mL). After workup this yielded the product as a glassy solid (310 mg, 90%). $^1$H-NMR (300 MHz, CD$_3$OD) δ (ppm) 1.10-1.90 (complex, Lys(3×CH$_2$), 184H); 2.20-2.70 (complex, Lys(N—CH$_2$), 64H); 3.0-3.20 (complex, 58H); 3.35 (s, PEG-OMe, 96H); 3.40-3.90 (complex, PEG-CH$_2$, 153611); 4.10-4.40 (broad s, 36H). HPLC (Hydrophilic/TFA) Rt=10.69 min; ESI MS (+ve) 22,472 [M+4H$^+$]; calc. m/z for C$_{1028}$H$_{1995}$N$_{65}$O$_{450}^+$ [M]$^+$: 22,468.01.

xviii. MAL-(CH$_2$)$_2$CONH-PEG$_{1100}$-CO-NEOEOEN [Su(NPN)$_2$] [Lys]$_{16}$ [PEG$_{570}$]$_{32}$ To a stirred solution of MAL-PEG$_{1100}$-NHS (1.25 mg, 0.895 μmol) in DCM (0.5 mL) was added a solution of [NH$_2$] EOEOEN [Su(NPN)$_2$] [Lys]$_{16}$ [PEG$_{570}$]$_{32}$ (20.1 mg, 0.895 μmol) and TEA (5 μL) in DCM (0.5 mL), dropwise. The solution was stirred at room temperature under nitrogen for 16 h. Volatiles were removed under reduced pressure and the product was used without further purification (21 mg). $^1$H-NMR (300 MHz, CD$_3$OD) δ (ppm) 1.10-1.90 (complex, Lys(3×CH$_2$), 184H); 2.20-2.70 (complex, Lys(N—CH$_2$), 64H); 3.0-3.20 (complex, 58H); 3.35 (s, PEG-OMe, 96H); 3.40-3.90 (complex, PEG-CH$_2$, 1628H); 4.10-4.40 (broad s, 36H); 6.82 (br s, MAL, 2H). HPLC (Hydrophilic/TFA) Rt=10.72 min.

xix. β-Laetoglobulin-MAL-(CH$_2$)$_2$CONH-PEG$_{1100}$-CO-NEOEOEN [Su(NPN)$_2$] [Lys]$_{16}$ [PEG$_{570}$]$_{32}$ A solution of MAL-(CH$_2$)$_2$CONH-PEG$_{1100}$-CO-NEOEOEN [Su(NPN)$_2$] [Lys]$_{16}$ [PEG$_{570}$]$_{32}$ (13.0 mg, 10 equiv.) in PBS buffer (pH 7.64, 250 mL) was added to bovine β-lactoglobulin B (1 mg, pH 7.64, 250 mL) in PBS buffer. The mixture was then shaken for 16 h (600 rpm, 26° C.) and analyzed by SDS-PAGE (12% Tris-Glycine Gel, 200 mV, 60 min), staining with coomassie blue and BaI$_2$. The desired dendrimer-protein construct was visualised by SDS-PAGE staining with coomassie blue, and appeared at the appropriate MW relative to the protein MW markers.

Example 2

β-Lactoglobulin-NHCO-PEG$_{570}$-NHCO(CH$_2$)$_2$-CO-NEOEOEN [Su(NPN)$_2$] [Lys]$_{16}$ [PEG$_{570}$]$_{32}$ i HO$_2$C—(CH$_2$)$_2$CO-NEOEOEN [Su(NPN)$_2$] [Lys]$_{16}$ [PEG$_{570}$]$_{32}$

To a stirred solution of succinic anhydride (5 mg, 0.047 mmol) in DMF (0.5 mL) was added a solution of [NH$_2$]

EOEOEN [Su(NPN)$_2$] [Lys]$_{16}$ [PEG$_{570}$]$_{32}$ (Example 1xvii) (53 mg, 2.36 μmol) and TEA (14 in DMF (0.5 mL), the solution was stirred at room temperature for 16 h. Volatiles were removed in vacuo and the residue taken up into water, purification was performed by tangential flow filtration on a Centramate (10 KDa membrane). The retentate was reduced to dryness to yield the desired product as an oily residue (69 mg). HPLC (Hydrophilic/TFA) Rt=10.83 min. $^1$H-NMR (300 MHz, CD$_3$OD) δ (ppm) 1.10-1.90 (complex, Lys(3× CH$_2$), 184H); 2.20-2.70 (complex, Lys(N—CH$_2$)+succinyl (CH$_2$)$_2$, 68H); 3.0-3.20 (complex, 58H); 3.35 (s, PEG-OMe, 96H); 3.40-3.90 (complex, PEG-CH$_2$, 1536H); 4.10-4.40 (broad s, 36H).

ii t-BuO$_2$C-PEG$_{570}$-NHCO(CH$_2$)$_2$-CO-NEOEOEN [Su(NPN)$_2$] [Lys]$_{16}$ [PEG$_{570}$]$_{32}$

To a stirred solution of HO$_2$C—(CH$_2$)$_2$CO-NEOEOEN [Su(NPN)$_2$] [Lys]$_{16}$ [PEG$_{570}$]$_{32}$ (30.6 mg, 1.36 μmol), H$_2$N-PEG$_{570}$-CO$_2$t-Bu (22 mg, 0.033 mmol) and TEA (8 μL) in DCM (0.5 mL) at 0° C., was added a solution of DCC (6.2 mg, 0.03 mmol) and HOBt (4.6 mg, 0.034 mmol) in DMF (0.5 mL). The solution was stirred at 0° C. for 10 mins, then allowed to reach room temperature and stirred for a further 16 h under nitrogen. Volatiles were removed in vacuo and the residue taken up into water, purification was performed by tangential flow filtration on a Centramate (10 KDa membrane). The retentate was reduced to dryness to yield the desired product as an oily residue (29.5 mg). $^1$H-NMR (300 MHz, CD$_3$OD) δ (ppm) 1.10-1.90 (complex, Lys(3×CH$_2$)+tBu, 193H); 2.20-2.70 (complex, Lys(N—CH$_2$)+succinyl (CH$_2$)$_2$, 68H); 3.0-3.20 (complex, 58H); 3.35 (s, PEG-OMe, 96H); 3.40-3.90 (complex, PEG-CH$_2$, 1582H); 4.10-4.40 (broad s, 36H).

iii HO$_2$C-PEG$_{570}$-NHCO(CH$_2$)$_2$-CO-NEOEOEN [Su(NPN)$_2$] [Lys]$_{16}$ [PEG$_{570}$]$_{32}$ To a stirred solution of t-BuO$_2$C-PEG$_{570}$-NHCO(CH$_2$)$_2$-CO-NEOEOEN [Su(NPN)$_2$] [Lys]$_{16}$ [PEG$_{570}$]$_{32}$ (29.5 mg, 1.27 μmol) in DCM (2 mL) at room temperature, was added TFA (0.5 mL); this solution was stirred at room temperature for 2 h. The reaction mixture was reduced to dryness and the residue taken up into 5 mL 1:1 MeCN/H$_2$O, the solvents were then removed in vacuo. This dissolution in 1:1 MeCN/H$_2$O, followed by complete removal of the solvents, was repeated twice more (33.2 mg). $^1$H-NMR (300 MHz, CD$_3$OD) δ (ppm) 1.10-1.90 (complex, Lys(3×CH$_2$), 184H); 2.20-2.70 (complex, Lys(N—CH$_2$)+succinyl (CH$_2$)$_2$, 68H); 3.0-3.20 (complex, 58H); 3.35 (s, PEG-OMe, 96H); 3.40-3.90 (complex, PEG-CH$_2$, 1582H); 4.10-4.40 (broad s, 36H).

iv NHS-CO-PEG$_{570}$-NHCO(CH$_2$)$_2$-CO-NEOEOEN [Su(NPN)$_2$] [Lys]$_{16}$ [PEG$_{570}$]$_{32}$

To a stirred solution of HO$_2$C-PEG$_{570}$-NHCO(CH$_2$)$_2$-CO-NEOEOEN [Su(NPN)$_2$] [Lys]$_{16}$ [PEG$_{570}$]$_{32}$ (33.2 mg, 1.43 μmol) and DIPEA (11 μL, 0.063 mmol) in DCM (2 mL) was added DCC (12.2 mg, 0.059 mmol) as a solid, the solution was stirred at room temperature for 10 mins. NHS (5.2 mg, 0.045 mmol) in DCM (0.5 mL) was added and the solution stirred at room temperature under nitrogen for 16 h. The volatiles were removed in vacuo, and DCM (2 mL) was added to the residue, the suspension was filtered through a 4.5 μm filter, the solvent was removed in vacuo (31.7 mg). This material was used without further purification.

v. β-Lactoglobulin-NHCO-PEG$_{570}$-NHCO(CH$_2$)$_2$-CO-NEOEOEN [Su(NPN)$_2$] [Lys]$_{16}$ [PEG$_{570}$]$_{32}$ NHS-CO-PEG$_{570}$-NHCO(CH$_2$)$_2$-CO-NEOEOEN [Su(NPN)$_2$] [Lys]$_{16}$ [PEG$_{570}$]$_{32}$ (10 eq. relative to protein) in PBS buffer (pH 7.64, 250 mL) was reacted with bovine β-lactoglobulin B (pH 7.64). The mixture was shaken for 16 h (600 rpm, 26° C.) and analyzed by SDS-PAGE (12% Tris-Glycine Gel, 200 mV, 60 min), staining with coomassie blue and BaI$_2$. The desired dendrimer-protein construct was visualised by SDS-PAGE staining with coomassie blue, and appeared at the appropriate MW relative to the protein MW markers.

Example 3

HSA-MAL-(CH$_2$)$_2$CONH-PEG$_{1100}$-CO-NEOEOEN [Su(NPN)$_2$] [Lys]$_{16}$ [PEG$_{570}$]$_{32}$

MAL-(CH$_2$)$_2$CONH-PEG$_{1100}$-CO-NEOEOEN [Su(NPN)$_2$] [Lys]$_{16}$ [PEG$_{570}$]$_{32}$ (Example 1 xviii) (10 eq. relative to protein) in PBS buffer (pH 7.64, 250 mL) was reacted with human serum albumin (pH 7.64). The mixture was shaken for 16 h (600 rpm, 26° C.) and analyzed by SDS-PAGE (12% Tris-Glycine Gel, 200 mV, 60 min), staining with coomassie blue and BaI$_2$. The desired dendrimer-protein construct was visualised by SDS-PAGE staining with coomassie blue, and appeared at the appropriate MW relative to the protein MW markers.

Example 4

NDP-α-MSH-CH$_2$CO NEOEOEN [Su(NPN)$_2$] [GlyLys]$_2$ [ε-CBz]$_2$ [Lys]$_2$ [PEG$_{570}$]$_4$ i. HO-Su(NPN)$_2$ [CBz]$_2$

A mixture of (NPN)$_2$ [CBz]2 (20.0 g, 0.05 mol) and succinic anhydride (6.0 g, 0.06 mol, 1.2 equivalents) in toluene (180 mL) was heated at 65° C. for 16 h. The reaction was cooled to room temperature and the white solid filtered and washed with methyl-t-butyl ether (3×100 mL) to yield the product in good yield 23.54 g (94%).

ii. PNPO-Su(NPN)$_2$ [CBz]$_2$

To a stirred solution of 4-nitrophenol (1.91 g, 13.7 mmol) and HO-Su(NPN)$_2$ [CBz]$_2$ (13.7 mmol) in EtOAc (150 mL) was added a solution of DCC (2.97 g, 14.4 mmol) in EtOAc (50 mL) at room temperature. The mixture stirred at room temperature overnight, filtered and washed with K$_2$CO$_3$ (1.0 M), brine 1:1 (3×300 mL), dried (MgSO$_4$), filtered and concentrated, providing 7.80 g of PNPO-Su(NPN)$_2$ [CBz]$_2$.

iii. [Boc] NEOEOEN [Su(NPN)$_2$] [CBz]$_2$

To a solution of [Boc] NEOEOEN (3 g, 12 mmol) in 1:1 DMF/DMSO (60 mL) was added TEA (3.4 mL, 240 mmol) and a solution of PNPO-Su(NPN)$_2$ [CBz]$_2$ (7.5 g, 12 mmol) in DMSO (30 mL). The solution was stirred at room temperature for 15 h. The solution was concentrated in vacuo and redissolved in water (300 mL). The aqueous solution was washed with EtOAc (3×300 mL) and the combined organic washings were dried over Na$_2$SO$_4$. Solvents were removed in vacuo and the crude oil purified by Silica Gel chromatography (3% MeOH/DCM) to provide [Boc] NEOEOEN [Su(NPN)$_2$] [CBz]$_2$ as a colourless viscous oil (8.2 g, 93%).

HPLC (Hydrophilic/TFA) Rt=9.20 min; ESI MS (+ve) 730.3 [M+1H]; calc. m/z for $C_{37}H_{55}N_5O_{10}$): 729.9.

iv. [Boc] NEOEOEN [Su(NPN)$_2$] [NH$_2$]$_2$

To a solution of [Boc] NEOEOEN [Su(NPN)$_2$] [CBz]$_2$ (500 mg, 0.68 mmol) in trifluoroethanol (13 mL) was added 10% w/w palladium on carbon (723 mg, 34 mmol). The suspension was stirred under an atmosphere of hydrogen at atmospheric pressure for 15 h. The suspension was then filtered though a 0.2 μm filter and the filtrate concentrated in vacuo to provide [Boc] NEOEOEN [Su(NPN)$_2$] [NH$_2$]$_2$ as a clear oil (250 mg, 80%). HPLC (Hydrophilic/TFA) Rt=4.50 min. ESI MS (+ve) 462.5 [M+H$^+$]; calc. m/z for $C_{21}H_{43}N_5O_6$: 461.6.

v. MeO-GlyLys [ε-CBz] [α-Boc]

To a stirred suspension of MeOGly.HCl (12.56 g, 0.11 mol) and DMF (200 mL) was slowly added TEA (42 mL, 0.30 mol) at room temperature. The active ester, PNPO-α-Boc-ε-CBz-Lys (50.15 g, 0.10 mol) was added to the suspension in 2-3 g portions. The bright yellow mixture was stirred at room temperature for 18 h. The volatiles were removed in vacuo and the resulting residue partitioned between EtOAc (200 mL), 10% Na$_2$CO$_3$ (100 mL) and water (175 mL). The organic layer was washed sequentially with 5% Na$_2$CO$_3$ (4×200 mL), 0.25 M HCl (3×50 mL) and brine (1×50 mL), dried (MgSO$_4$), filtered and concentrated to give the product as a colourless oil (44.39 g, 98%). HPLC (Hydrophobic/Formate) Rt=5.22 min. ESI MS (+ve) 452.02 [M+H]$^+$; calc. m/z for $C_{22}H_{33}N_3O_7$: 451.52.

vi. MeO-GlyLys [ε-CBz] [α-NH$_2$.TFA]

To a stirred, chilled solution of MeO-GlyLys [ε-CBz] [α-Boc] (43.4 g, 96.03 mmol) in acetic acid (150 mL) was added neat TFA in portions (total 170 mL). The reaction was stirred at room temperature for 5 h. Volatiles were removed under reduced pressure; residual TFA and acetic acid were removed by azeotroping with methanol (5×200 mL). The product was obtained as a pale yellow oil (46.04 g). HPLC (Hydrophilic/Formate) 12.33 min; ESI MS (+ve) 352 [M+H]$^+$; calc. m/z for $C_{17}H_{25}N_3O_5$: 351.40.

vii. MeO-GlyLys [ε-CBz] [α-Lys] [Boc]$_2$

To a stirred solution of MeO-GlyLys [ε-CBz] [α-NH$_2$.TFA] (96 mmol) in DMF (200 mL) was added TEA (33.5 mL, 0.24 mol) followed by DBL-OPNP (49.4 g, 0.106 mol). The solution was stirred at room temperature for 17 h. A solution of glycine (3.98 g, 53 mmol) in water (50 mL) was added to the crude reaction mixture and stirring was continued for 18 h further. Water (200 mL) was added and the yellow precipitate was collected by filtration, then resuspended in 5% Na$_2$CO$_3$ (200 mL); and stirred for 1.5 h. The crude product was collected by filtration and resuspended in water (3×200 mL); the solids were collected by filtration and air dried to yield the product as a fine yellow powder (61.07 g, 94%). HPLC (Hydrophobic/Formate) Rt=7.90 min; ESI MS (+ve) 680.15 [M+H]+; calc. m/z for $C_{33}H_{53}N_5O_{10}$: 679.82.

viii. MeO-GlyLys [ε-CBz] [α-Lys] [NH$_2$.TFA]$_2$

To a stirred suspension of MeO-GlyLys [ε-CBz] [α-Lys] [Boc]$_2$ (4 g, 7.36 mmol) in acetic acid (15 mL) at 0° C. was added TFA (15 mL), dropwise. The mixture was allowed to warm to room temperature and was stirred at room temperature overnight. The solvents were removed and the residue dissolved in water (100 mL) and filtered. The filtrate was lyophilized to give a colourless oil (4.4 g). HPLC/(Hydrophilic/TFA) Rt=5.03 min; ESI MS (+ve)=480 [M+H$^+$]; calc. m/z for $C_{23}H_{37}N_5O_6$: 479.5.

ix. MeO-GlyLys [ε-CBz] [α-Lys] [PEG$_{570}$]$_2$

To a stirred suspension of MeO-GlyLys [ε-CBz] [α-Lys] [NH$_2$.TFA]$_2$ (735 mg, 1.04 mmol) in DMF (anhydrous, 20 mL) was added TEA (1.5 mL, 5 equivalents per amine) followed by a solution of m-dPEG$_{570}$-NHS (1.5 g, 1.05 equivalents per amine) in DMF (10 mL). The mixture was stirred at room temperature overnight. The solvents were removed and the residue purified on a column of silica gel (0.063-0.04 mm, eluents 7%~30% MeOH/DCM) to give the desired product as a colourless oil (1.0 g). HPLC (Hydrophilic/TFA) Rt=7.87 min; ESI MS (+ve) 828 [M+2×NH$_4$]$^{2+}$, 811 [M+2H]$^{2+}$, 541 [M+3H]$^{3+}$; calc. m/z for $C_{75}H_{137}N_5O_{32}$: 1620.9.

x. HO-GlyLys [ε-CBz] [α-Lys] [PEG$_{570}$]$_2$

To a stirred suspension of MeO-GlyLys [ε-CBz] [α-Lys] [PEG$_{570}$]$_2$ (1.0 g, 0.62 mmol) in THF (20 mL) was added 1M LiOH (2 mL). The mixture was stirred at room temperature for 3 h; followed by acidification with 1 M HCl to pH 6. The solvents were removed and the residue dissolved in water and lyophilized to give the product as a colourless solid. HPLC (Hydrophilic/TFA) Rt=7.61 min; ESI MS (+ve) 821 [M+(2×NH$_4$)]$^{2+}$, 804 [M+2H]$^{2+}$, 536 [M+3H]$^{3+}$; calc. m/z for $C_{74}H_{135}N_5O_{32}$: 1606.

xi. [Boc] NEOEOEN [Su(NPN)$_2$] [GlyLys]$_2$ [ε-CBz]$_2$ [Lys]$_2$ [PEG$_{570}$]$_4$

To a stirred solution of [Boc] NEOEOEN [Su(NPN)$_2$] [NH$_2$]$_2$ (Example 4iv) (100 mg, 0.22 mmol) and HO-GlyLys [ε-CBz] [α-Lys] [PEG$_{570}$]$_2$ (700 mg, 0.44 mmol) in DMF (anhydrous, 9 mL) at 0° C., was added PyBop (250 mg) and DIPEA (160 μL). The mixture stirred at room temperature overnight. Volatiles were removed in vacuo to give a residue which was chromatographed on a silica gel column (0.063-0.04 mm, eluants 10%-30% MeOH/DCM) to give 600 mg the product as a colourless oil. HPLC (Hydrophilic/TFA) Rt=9.18 min; ESI MS (+ve) 886 [M-Boc+4H]$^{4+}$, 729 [M+5H]$^{5+}$, 709 [M-Boc+5H]$^{5+}$; data deconvoluted using transform calculation to give 3638.9[M+H]$^+$; calc. m/z for $C_{169}H_{309}N_{15}O_{68}$: 3639.3.

xii. [TFA.NH$_2$] EOEOEN [Su(NPN)$_2$] [GlyLys]$_2$ [ε-CBz]$_2$ [Lys]$_2$ [PEG$_{570}$]$_4$

[Boc] NEOEOEN [Su(NPN)$_2$] [GlyLys]$_2$ [ε-CBz]$_2$ [Lys]$_2$ [PEG$_{570}$]$_4$ could be suspended in 20% TFA/DCM and stirred at room temperature for 1 h. Removal of the volatiles should provide the product.

xiii. [ClCH$_2$CO] NEOEOEN [Su(NPN)$_2$] [GlyLys]$_2$ [ε-CBz]$_2$ [Lys]$_2$ [PEG$_{570}$]$_4$ To a solution of [TFA.NH$_2$] EOEOEN [Su(NPN)$_2$] [GlyLys]$_2$ [ε-CBz]$_2$ [Lys]$_2$ [PEG$_{570}$]$_4$ in buffer (100 mL 0.1 M Na$_2$HPO$_4$; 100 mL 0.1 M HCl, pH ~8.5) could be added chloroacetyl chloride. With stirring for 2 h, the product

[ClCH$_2$CO] NEOEOEN [Su(NPN)$_2$] [GlyLys]$_2$ [ε-CBz]$_2$ [Lys]$_2$ [PEG$_{570}$]$_4$ should be detectable by HPLC/MS.

xiv. NDP-α-MSH-CH$_2$CO NEOEOEN [Su(NPN)$_2$] [GlyLys]$_2$ [ε-CBz]$_2$ [Lys]$_2$ [PEG$_{570}$]$_4$ To an excess of mercapto-NDP-α-MSH (mercapto-Ser-Tyr-Ser-Nle-His-DPhe-Arg-Trp-Gly-Lys-Pro-Val-NH$_2$) could be added a freshly prepared solution of [ClCH$_2$CO] NEOEOEN [Su(NPN)$_2$] [GlyLys]$_2$ [ε-CBz]$_2$ [Lys]$_2$ [PEG$_{570}$]$_4$ in a buffer of 0.1 M sodium hydrogen orthophosphate/0.1 M HCl (pH 8.5). After stirring at room temperature for 16 h, the conjugated product should be detectable in the reaction mixture by HPLC-MS.

Example 5

[Biotin] NEOEOEN [(Su(NPN)$_2$] [Lys]$_{16}$ [COCH$_2$O-3,6-Naph (SO$_3$Na)$_2$]$_{32}$ i. [Biotin] NEOEOEN [(Su(NPN)$_2$] [Lys]$_{16}$ [Boc]$_{32}$

PyBOP (20 mg, 0.04 mmol) was added to a stirred solution of [NH$_2$] EOEOEN [(Su(NPN)$_2$] [Lys]$_{16}$ [Boc]$_{32}$ (Example 1xiii) (109 mg, 0.015 mmol) in DMF/DMSO (1:1) (3 mL). A solution of biotin-NHS ester (13 mg, 0.38 mmol) and DIPEA (40 µL, 0.23 mmol) in DMF/DMSO (1:1) (2 mL) was added gradually. The mixture was stirred at room temperature for 16 h. The reaction mixture was poured into MeCN (300 mL) and a precipitate formed. The precipitate was collected by filtration and dried in vacuo to give [Biotin] NEOEOEN [(Su(NPN)$_2$] [Lys]$_{16}$ [Boc]$_{32}$ as a white solid (119 mg, 106%). HPLC (Hydrophobic/TFA) Rt=10.9 min; ESI MS (+ve) m/z=1910.02 (M–4H)$^{4+}$; 1528.33 (M–5H)$^{5+}$. Data deconvoluted using maximum entropy calculation to give MW=7638 [M$^+$]; calc. m/z for C$_{366}$H$_{665}$N$_{67}$O$_{100}$S(H form) [M$^+$]: 7636.76.

ii. [Biotin] NEOEOEN [(Su(NPN)$_2$] [Lys]$_{16}$ [NH$_2$.TFA]$_{32}$

A solution of TFA and DCM (1:1) (2 mL) was added dropwise to a stirred suspension of [Biotin] NEOEOEN [(Su(NPN)$_2$] [Lys]$_{16}$ [Boc]$_{32}$ (56 mg, 0.007 mmol) in DCM (3 mL). The mixture was stirred at room temperature for 14 h. The solvent was removed under reduced pressure and the residue triturated with diethyl ether (3×10 mL). The product was dried in vacuo to give [Biotin] NEOEOEN [(Su(NPN)$_2$] [Lys]$_{16}$ [NH$_2$.TFA]$_{32}$ as a white solid. HPLC (Hydrophilic/TFA) Rt=4.35 min; ESI MS (+ve) m/z=1478.96 (M–3H)$^{3+}$; 1109.38 (M–4H)$^{4+}$; 887.70 (M–5H)$^{5+}$; 739.84 (M–6H)$^{6+}$. Data deconvoluted using maximum entropy calculation to give MW=4433 [M$^+$], (H form); calc. m/z for C$_{206}$H$_{409}$N$_{67}$O$_{36}$S (H form) [M$^+$]: 4433.01.

iii. [Biotin] NEOEOEN [(Su(NPN)$_2$] [Lys]$_{16}$ [COCH$_2$O-3,6-Naph(SO$_3$Na)$_2$]$_{32}$ PyBOP (0.26 g, 0.50 mmol) was added to a stirred solution of [Biotin] NEOEOEN [(Su(NPN)$_2$] [Lys]$_{16}$ [NH$_2$.TFA]$_{32}$ (56 mg, 0.007 mmol) in DMF/DMSO (1:1) (6 mL). A solution of HOCOCH$_2$O-3,6-Naph(SO$_3$Na)$_2$ (0.21 g, 0.53 mmol) and DIPEA (0.4 mL, 2.30 mmol) in DMF/DMSO (1:1) (5 mL) was added gradually. The mixture was stirred at room temperature for 16 h. The reaction mixture was poured into water (0.2 L) and filtered. Purification was performed by tangential flow filtration on a Centramate (2K membrane, 0.5 L sample reservoir). After an initial wash with Milli-Q water (5 L) the retentate was washed with two aliquots of 1M Na$_2$SO$_4$ (100 mL) separated by a Milli-Q water wash (1 L), then filtration was continued until filtrate pH was neutral (approx. 5 L). The retentate was concentrated in vacuo, and freeze dried to give [Biotin] NEOEOEN [(Su(NPN)$_2$] [Lys]$_{16}$ [COCH$_2$O-3,6-Naph(SO$_3$Na)$_2$]$_{32}$ as a white solid (80 mg, 68%). HPLC/MS (Ion Pairing) Rt=8.74 min; ESI MS (–ve) m/z=1544.32 (M–10H)$^{10-}$; 1403.91 (M–11H)$^{11-}$; 1286.51 (M–12H)$^{12-}$; 1187.62 (M–13H)$^{13-}$; 1102.86 (M–14H)$^{14-}$; 1029.21 (M–15H)$^{15-}$; 964.96 (M–16H)$^{16-}$; 907.83 (M–17H)$^{17-}$; 857.56 (M–18H)$^{18-}$; 812.29 (M–19H)$^{19-}$; 771.62 (M–20H)$^{20-}$; 734.82 (M–21H)$^{21-}$; 701.41 (M–22H)$^{22-}$; 670.74 (M–23H)$^{23-}$; 642.88 (M–24H)$^{24-}$; 617.15 (M–25H)$^{25-}$; 593.49 (M–26H)$^{26-}$; 571.50 (M–27H)$^{27-}$. Data deconvoluted using maximum entropy calculation to give MW=15453 [M$^-$] (H form); calc. m/z for C$_{590}$H$_{665}$N$_{67}$O$_{292}$S$_{65}$ (H form) [M$^-$]: 15451.

Example 6

[Biotin] NEOEOEN [(Su(NPN)$_2$] [Lys]$_{16}$ [CO-3.5-Ph (SO$_3$Na)$_2$]$_{32}$ PyBOP (0.23 g, 0.44 mmol) was added to a stirred solution of [biotin] [NEOEOEN(Su(NPN)$_2$] [Lys]$_{16}$ [NH$_2$.TFA]$_{32}$ (Example 5ii) (48 mg, 0.006 mmol) in DMF/DMSO (1:1) (6 mL). A solution of 4-sulfobenzoic acid (0.12 g, 0.60 mmol) and DIPEA (0.3 mL, 1.72 mmol) in DMF/DMSO (1:1) (5 mL) was added gradually. The mixture was stirred at room temperature for 16 h. The reaction mixture was poured into water (0.2 L) and filtered. Purification was performed by tangential flow filtration on a Centramate (1K membrane, 0.5 L sample reservoir). After an initial wash with Milli-Q water (5 L) the retentate was washed with two aliquots of 1M Na$_2$CO$_3$ (100 mL) separated by a Milli-Q water wash (1 L), then filtration was continued until filtrate pH was neutral (approx. 5 L). The retentate was concentrated in vacuo, and freeze dried to give [biotin] NEOEOEN [(Su(NPN)$_2$] [Lys]$_{16}$ [Ph-3,5-(SO$_3$Na)$_2$]$_{32}$ as a white solid (103 mg, 123%). HPLC/MS (Ion Pairing) Rt=8.60 min; ESI MS (–ve) m/z=919.70 (M–14H)$^{14-}$; 858.30 (M–15H)$^{15-}$; 804.56 (M–16H)$^{16-}$; 757.08 (M–17H)$^{17-}$; 715.01 (M–18H)$^{18-}$; 677.48 (M–19H)$^{19-}$; 643.61 (M–20H)$^{20-}$. Data deconvoluted using maximum entropy calculation to give MW=12889 [M$^-$] (H form); calc. m/z for (C$_{430}$H$_{537}$N$_{67}$O$_{260}$S$_{65}$) (H form) [M$^-$]: 12888.

Example 7

[Biotin] NEOEOEN [(Su(NPN)$_2$] [Lys]$_8$ [COCH$_2$O-3,6-Naph(SO$_3$Na)$_2$]$_{16}$ i. [Biotin] NEOEOEN [(Su(NPN)$_2$] [Boc]$_{16}$

PyBOP (20 mg, 0.04 mmol) was added to a stirred solution of [NH$_2$] EOEOEN [(Su(NPN)$_2$] [Lys]$_8$ [Boc]$_{16}$ (Example 7i) (55 mg, 0.015 mmol) in DMF (1:1) (3 mL). A solution of biotin-NHS ester (13 mg, 0.38 mmol) and DIPEA (20 µL, 0.12 mmol) in DMF (1 mL) was added gradually. The mixture was stirred at room temperature for 16 h. The reaction mixture was poured into MeCN (0.2 L) and a precipitate formed. The precipitate was collected by filtration and dried in vacuo to give [Biotin] NEOEOEN [(Su(NPN)$_2$] [Lys]$_8$ [Boc]$_{16}$ as a white solid (34 mg, 58%). HPLC (Hydrophobic/TFA) Rt=8.27 min; ESI MS (+ve) m/z=1328.87 [(M–3H)$^{3+}$]; 996.98 [(M–4H)$^{4+}$]. Data deconvoluted using transform calculation to give MW=3984 [M⁺]; calc. m/z for C$_{190}$H$_{345}$N$_{35}$O$_{52}$S (H form) [M⁺]: 3984.10.

ii. [Biotin] NEOEOEN [(Su(NPN)$_2$] [Lys]$_8$ [NH$_2$.TFA]$_{16}$

A solution of TFA and DCM (1:1) (2 mL) was added dropwise to a stirred suspension of [Biotin] NEOEOEN [(Su(NPN)$_2$] [Lys]$_8$ [Boc]$_{16}$ (34 mg, 0.009 mmol) in DCM (3 mL). The mixture was stirred at room temperature for 14 h. The solvent was removed under reduced pressure and the residue triturated with diethyl ether (3×10 mL). The product was dried in vacuo to give [Biotin] NEOEOEN [(Su(NPN)$_2$] [Lys]$_8$ [NH$_2$.TFA]$_{16}$ as a white solid. HPLC (Hydrophilic/TFA) Rt=4.27 min; ESI MS (+ve) m/z=1191.87 [(M−2H)$^{2+}$]; 795.03 [(M−3H)$^{3+}$]; 596.44 [(M−4H)$^{4+}$]; 477.23 [(M−5H)$^{5+}$]. Data deconvoluted using maximum entropy calculation to give MW=2382 [M⁺] (H form); calc. m/z for C$_{110}$H$_{217}$N$_{35}$O$_{20}$S (H form) [M⁺]: 2382.22.

iii. [Biotin] NEOEOEN [(Su(NPN)$_2$] [Lys]$_8$ [COCH$_2$O-3,6-Naph (SO$_3$Na)$_2$]$_{16}$ PyBOP (0.16 g, 0.31 mmol) was added to a stirred solution of [Biotin] NEOEOEN [(Su(NPN)$_2$] [Lys]$_8$ [NH$_2$.TFA]$_{16}$ (20 mg, 0.009 mmol) in DMF/DMSO (1:1) (4 mL). A solution of HOCOCH$_2$O-3,6-Naph(SO$_3$Na)$_2$ (0.12 g, 0.28 mmol) and DIPEA (0.2 mL, 1.15 mmol) in DMF/DMSO (1:1) (2 mL) was added gradually. The mixture was stirred at room temperature for 16 h. The reaction mixture was poured into water (0.25 L) and filtered. Purification was performed by tangential flow filtration on a Centramate (2K membrane, 0.5 L sample reservoir). After an initial wash with Milli-Q water (5 L) the retentate was washed with two aliquots of 1M Na$_2$CO$_3$ (100 mL) separated by a Milli-Q water wash (1 L), then filtration was continued until filtrate pH was neutral (approx. 5 L). The retentate was concentrated in vacuo, and freeze dried to give [Biotin] NEOEOEN [(Su(NPN)$_2$] [Lys]$_8$ [COCH$_2$O-3,6-Naph (SO$_3$Na)$_2$]$_{16}$ as a white solid (69 mg, 94%). HPLC/MS (Ion Pairing) Rt=10.8 min; ESI MS (−ve) m/z=1314.25 (M−6H)$^{6-}$; 1126.54 (M−7H)$^{7-}$; 985.30 (M−8H)$^{8-}$; 875.91 (M−9H)$^{9-}$; 787.96 (M−10H)$^{10-}$; 716.35 (M−11H)$^{11-}$; 656.60 (M−12H)$^{12-}$; 605.97 (M−13H)$^{13-}$; 562.90 (M−14H)$^{14-}$; 525.03 (M−15H)$^{15-}$. Data deconvoluted using maximum entropy calculation to give MW=7891 [M⁻] (H form); calc. m/z for C$_{302}$H$_{345}$N$_{35}$O$_{148}$S$_{33}$ (H form) [M⁻]: 7891.39. CE (pH 9); Rt=8.00 min: 75.5% purity.

Example 8

[p-NO$_2$-CBz] NEOEOEN [Su(NPN)$_2$] [Lys]$_2$ [Su(NPN)$_2$(PEG$_{1100}$)(MTX-α-OtBu)]$_4$

To a stirred mixture of Su(NPN)$_2$(PEG$_{1100}$)(MTX-α-OtBu) (75 mg, 41.2 μmol) and [p-NO$_2$-CBz] NEOEOEN [Su(NPN)$_2$] [Lys]$_2$ [NH$_2$.TFA]$_4$ (8.4 mg, 8.2 μmol) in DMF (3.0 mL) at 0° C. was added PyBop (23 mg, 44 μmol) and DIPEA (29 μL, 0.16 mmol). The mixture was kept at 0° C. for 30 min, then allowed to warm to room temperature overnight. The solvent was removed and the crude purified by PREP HPLC (Waters XTerra Prep RP$_{18}$ 10 μm, 19×250 mm, 5-45% ACN/H$_2$O, 15-55 min then hold, 0.1% TFA, Rt=58 min) providing 40 mg (74%) of the desired product as a viscous yellow oil. $^1$H-NMR (300 MHz, CD$_3$OD) δ (ppm) 1.48 (s, OtBu, 36H), 1.54-1.95 (complex, Lys(3×CH$_2$)+NPN(2×CH$_2$), 32H); 2.05-2.32 (complex, Glu(CH$_2$), 8H); 2.34-2.78 (complex, succinyl (CH$_2$)$_2$+PEG-CH$_2$+Glu(CH$_2$), 36H); 3.06-3.48 (complex, NPN(4×CH$_2$)+PEG-Me+N-Me+Lys (N—CH$_2$), 68H); 3.50-4.06 (complex, PEG-OCH$_2$, 388H); 4.20-4.28 (complex, Lys(α-CH), 2H), 4.40-4.48 (complex, Glu(α-CH), 4H); 4.94 (s, N—CH$_2$, 8H); 5.20 (s, CBz-CH$_2$, 2H); 6.87 (d, 8.7 Hz, MTX, 8H); 7.58 (d, 8.4 Hz, p-NO$_2$-CBz, 2H); 7.78 (d, 8.7 Hz, MTX, 8H); 8.20 (d, 8.4 Hz, p-NO$_2$-CBz, 2H); 8.68 (s, MTX, 4H). HPLC (Hydrophilic/TFA) Rt=9.58 min; ESI MS (+ve) 8,019 [M+H⁺]; calc. m/z for C$_{372}$H$_{645}$N$_{54}$O$_{134}$ [M+H⁺]8,018.38.

Example 9

[CBz] NEOEOEN [Su(NPN)$_2$] [Lys]$_4$ [Su(NPN)$_2$(PEG$_{570}$)(MTX-α-OtBu)]$_8$

To a stirred mixture of Su(NPN)$_2$(PEG$_{570}$)(MTX-α-OtBu) (36 mg, 27.8 μmol) and [CBz] NEOEOEN [Su(NPN)$_2$] [Lys]$_4$ [NH$_2$.TFA]$_8$ (6.0 mg, 2.8 μmol) in DMF (2.0 mL) at 0° C. was added PyBop (16 mg, 30.6 μmol) and DIPEA (16 μL, 89 μmol). The mixture was kept at 0° C. for 30 min, then allowed to warm to room temperature overnight. The solvent was removed and the crude purified by PREP HPLC (Waters XTerra Prep RP$_{18}$ 10 μm, 19×250 mm, 5-45% MeCN/H$_2$O, 15-55 min then hold, 0.1% TFA, Rt=58 min) providing 17 mg (53%) of the desired product as a viscous yellow oil. $^1$H-NMR (300 MHz, CD$_3$OD) δ (ppm) 1.16-1.56 (complex, Lys(3×CH$_2$)+NPN(2×CH$_2$)+OtBu, 150H); 2.02-2.27 (complex, Glu (CH$_2$), 16H); 2.30-2.75 (complex, succinyl (CH$_2$)$_2$+PEG-CH$_2$+Glu(CH$_2$), 68H); 3.00-3.42 (complex, NPN(4∴CH$_2$)+PEG-Me+N-Me+Lys(N—CH$_2$), 134H); 3.43-3.88 (complex, PEG-OCH$_2$, 380H); 4.04-4.32 (complex, Lys(α-CH), 7H), 4.34-4.50 (complex, Glu(α-CH), 8H); 4.91 (s, N—CH$_2$, 16H); 5.03 (s, CBz-CH$_2$, 2H); 6.83 (d, 8.7 Hz, MTX, 16H); 7.28 (br s, CBz, 5H); 7.75 (d, 8.7 Hz, MTX, 16H); 8:64 (s, MTX, 8H). HPLC (Hydrophilic/TFA) Rt=9.41 min; ESI MS (+ve) 11,477.42 [M+H⁺]; calc. m/z for C$_{540}$H$_{890}$N$_{105}$O$_{164}$ [M+H⁺] 11,477.44.

Alternative/Key Intermediates

Example 10

[CBz] NEOEOEN [Su(NPN)$_2$] [Lys]$_{16}$ [NH$_2$.TFA]$_{32}$

[CBz] NEOEOEN [Su(NPN)$_2$] [Lys]$_{16}$ [Boc]$_{32}$ (Example 1xii) (389 mg, 51.6 μmol) was dissolved in acetic acid (1.9 mL) and the stirred solution cooled in an ice bath until the acetic acid began to freeze. The ice bath was removed and TFA was carefully added until the acetic acid just melted. The stirred solution was once again placed in the ice bath and the remainder of the TFA (total amount of TFA used was 1.9 mL, 24.8 mmol) was added. The ice bath was removed and the solution stirred at room temperature for 21 h. The TFA and acetic acid were evaporated in vacuo and water (5 mL) was added to the oily residue. The solution was then concentrated in vacuo and the process was repeated with more water (2×5 mL). The final oil was dissolved in water (5 mL), the solution filtered and freeze dried to give [CBz] NEOEOEN [Su(NPN)$_2$] [Lys]$_{16}$ [NH$_2$.TFA]$_{32}$ (397 mg, 96%) as an amorphous white solid. $^1$H-NMR (300 MHz, D$_2$O) δ (ppm) 1.20-1.65 (complex, 92H); 1.65-1.85 (complex, 62H); 1.85-2.05 (complex, 30H); 2.51 (m, 2H); 2.61 (m, 2H); 2.95-3.10 (complex, 34H); 3.10-3.45 (complex, 38H); 3.55-3.70 (complex, 8H); 3.94 (t, J=6.6 Hz, 8H); 4.05 (t, J=6.6 Hz, 8H); 4.15-4.28 (complex, 8H); 4.28-4.39 (complex, 6H); 5.00 (s, 2H); 7.32-7.49 (complex, 5H); HPLC (Hydrophilic/TFA) Rt=8.8 min; EST MS (+ve) 1447.8 [M+3H]$^{3+}$/3, 1086.1 [M+H]$^{4+}$/4, 868.9 [M+5H]$^{5+}$/5, 724.3 [M+6H]$^{6+}$/6; calc. m/z for $C_{204}H_{404}N_{65}O_{36}{}^{3+}$ [M+3H]$^{3+}$: 1447.1, calc. m/z for $C_{204}H_{405}N_{65}O_{36}{}^{4+}$ [M+4H]$^{4+}$: 1085.6, calc. m/z for $C_{204}H_{406}N_{65}O_{36}{}^{5+}$[M+5H]$^{5+}$: 868.6, calc. m/z for $C_{204}H_{407}N_{65}O_{36}{}^{6+}$ [M+6H]$^{6+}$: 724.0.

Example 11

[CBz] NEOEOEN [Su(NPN)$_2$]$_2$ [Boc]$_4$

To a solution of [CBz] NEOEOEN [Su(NPN)$_2$] [Boc]$_2$ (11.8 g, 17 mmol) in acetic acid (25 mL), was added TFA (25 mL). The solution was stirred for 10 h then quenched with water (100 mL). Solvent was removed in vacuo and the resulting oily residue dissolved in water (50 mL) and filtered through a 4.5 µm filter before freeze drying. The freeze dried material was dissolved in DMF (100 mL) and to this solution was added TEA (19 mL) and a solution of PNPO-Su (NPN)$_2$-Boc$_2$ (20.7 g, 21 mmol) in DMF (100 mL). The solution was left to stir at room temperature overnight. To the solution was then added a solution of glycine (2 g) in water (120 mL). The combined solution was stirred at room temperature for 16 h. Solvent was removed in vacuo and the resulting yellow precipitate redissolved in EtOAc (200 mL). This solution was then washed with water (50 mL), 0.5M HCl (50 mL) and 1M Na$_2$CO$_3$ (4×50 mL). The organic layer was then dried over Na$_2$SO$_4$ and the solvent removed in vacuo. The resulting yellow oil was then purified by silica gel chromatography to provide a clear viscous oil (18.5 g, 14 mmol, 82%). ESI MS (+ve) 562 [(M+2H$^+$−2Boc)/2]; calc m/z for $C_{64}H_{111}N_{11}O_{18}$ [M+H]: 1323.63.

Example 12

[CBz] NEOEOEN [Su(NPN)$_2$]$_4$ [Boc]$_8$

To a solution of [CBz] NEOEOEN [Su(NPN)$_2$]$_2$ [Boc]$_4$ (12.8 g, 9.7 mmol) in acetic acid (50 mL), was added TFA (50 mL). This solution was stirred overnight at room temperature after which solvent was removed in vacuo to provide a clear viscous oil. The oil was dissolved in DMF (75 mL) and to this solution was added a slurry of TEA (28 mL) and PNPO-Su (NPN)$_2$-[Boc]$_2$ (25.7 g, 47 mmol).The reaction mixture was stirred overnight at room temperature. To the reaction mixture was added a solution of glycine (2 g) in water (60 mL). The combined solution was left to stir for a 16 h. Solvent was removed in vacuo and the resulting yellow precipitate redissolved in EtOAc (400 mL). This solution was then washed with water (50 mL), 0.5M HCl (2×50 mL) and 1M Na$_2$CO$_3$ (5×50 mL). The organic layer was then dried over Na$_2$SO$_4$ and the solvent removed in vacuo to provide a yellow foam (24 g, 9.3 mmol, 96%). A portion of this material (22.5 g) was then purified by silica gel chromatography (MeOH/DCM gradient) to provide a white foam (15 g, 5.8 mmol, 66%). ESI MS (+ve) 1289 [(M+2H$^+$)/2]; 760 [(M+3H$^+$−3Boc)/3]; calc. m/z for $C_{124}H_{219}N_{23}O_{34}$ [M+H]: 2577.3.

Example 13

[CBz] NEOEOEN [Su(NPN)$_2$]$_8$ [Boc]$_{16}$

To a solution of 1:1 acetic acid/TFA (100 mL), was added [CBz] NEOEOEN [Su(NPN)$_2$]$_4$[Boc]$_8$ (12 g, 4.7 mmol). The reaction mixture was stirred at room temperature for 20 h. Solvent was removed in vacuo and the clear residue redissolved in DMF (150 mL).To this solution was added a slurry of TEA (42 mL) and PNPO-Su(NPN)$_2$-Boc$_2$ (24.9 g, 45 mmol) in DMF (75 mL). The reaction mixture was left to stir at room temperature overnight. Solvent was removed in vacuo and the resulting yellow precipitate redissolved in EtOAc (2 L). This solution was then washed with brine (2×50 mL), 1M Na$_2$CO$_3$ (2×1 mL). Solvent was removed in vacuo to provide a yellow oil. ESI MS (+ve) 1695 [(M+$^3$H$^+$)/3]; 1272 [(M+4H$^+$)/4]; 1018 [(M+5H$^+$)/5]; calc. m/z for $C_{244}H_{435}N_{47}O_{66}$ [M+H]: 5084.3.

The invention claimed is:

1. A macromolecule comprising:
   (1) a dendrimer comprising:
      (i) a triamino, tetraamino or pentaamino core moiety having a first nitrogen atom for attachment to a first functional moiety and at least two further nitrogen atoms for attachment to lysine or lysine analogue building units;
      (ii) one or more layers of lysine or lysine analogue building units, wherein each building unit in a first of the layers is attached to the core moiety by an amide bond, through the at least two further nitrogen atoms of the core moiety, and any building units in subsequent layers are attached to a previous layer through an amide bond, wherein an outermost layer of the one or more lysine or lysine analogue building units has at least one surface amine for attachment to the one or more second functional moieties;
   (2) a first functional moiety attached to the core moiety through the first nitrogen atom; and
   (3) one or more second functional moieties attached to the surface amines of the outermost layer of lysine or lysine analogue building units;
wherein the second functional moiety is a pharmacokinetic modifying agent selected from the group consisting of polyfluorocarbons, fatty acids, lipids, oligo- and poly-saccharides deoxycholic acids, polyethylene glycol (PEG), polypropyleneglycol (PPG), alkyl capped forms of PEG and PPG, and polyethyloxazoline motif, and the first functional moiety is not lysine or lysine analogue, and is an agent selected from the group consisting of pharmaceutically active agents and interacting agents.

2. A macromolecule according to claim 1 wherein the building units are selected from the group consisting of:

Lysine 1 having the structure:

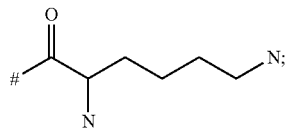

Glycyl-Lysine 2 having the structure:

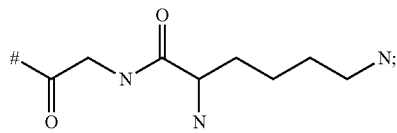

Analogue 3, having the structure below, where a is an integer 1 or 2; and b and c are independently integers 1, 2, 3 or 4:

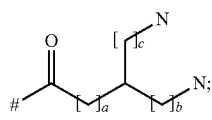

Analogue 4, having the structure below, where a is an integer 0, 1 or 2; and b and c are independently integers 2, 3, 4, 5 or 6:

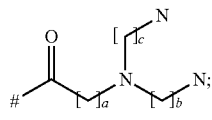

Analogue 5, having the structure below, where a is an integer 0, 1, 2, 3, 4 or 5; and b and c are independently integers 1, 2, 3, 4 or 5:

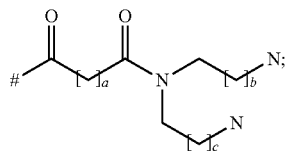

Analogue 6, having the structure below, where a is an integer 0, 1, 2, 3, 4 or 5; and b and c are independently integers 0, 1, 2, 3, 4 or 5:

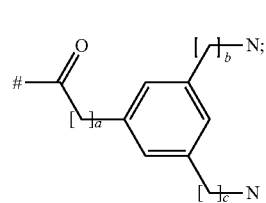

Analogue 7, having the structure below, where a is an integer 0, 1, 2, 3, 4 or 5; and b and c are independently integers 1, 2, 3, 4 or 5:

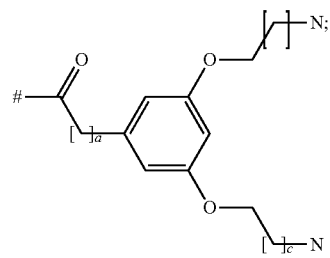

Analogue 8, having the structure below, where a is an integer 0, 1, 2, 3, 4 or 5; and b, c and d are independently integers 1, 2, 3, 4 or 5:

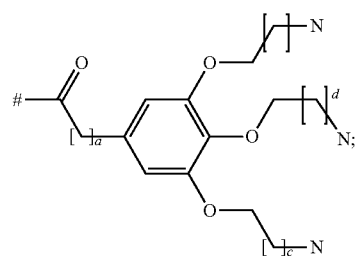

and

Analogue 9, having the structure below, where a is an integer 0, 1, 2, 3, 4 or 5; and b and c are independently integers 1, 2, 3, 4 or 5:

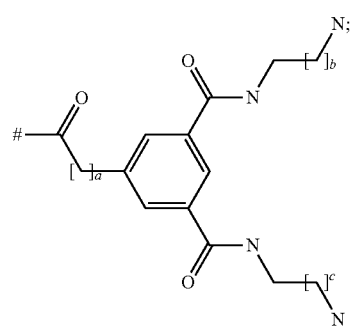

wherein each # denotes the carbonyl residue of the apex carboxyl group which forms an amide bond with a nitrogen atom of the core or a nitrogen atom of a previous generation of building units;

and wherein any methylene group of the building units may be replaced by a methyleneoxy ($CH_2$—O) or ethyleneoxy (CH$_2$—CH$_2$—O) group, provided that this does not result in the formation of a carbonate (—O—C(O)—O—) or carbamate (—O—C(O)—N—) moiety within the building unit.

3. A macromolecule according to claim 2 wherein the building units are selected from the group consisting of Lysine 1, Glycyl-Lysine 2 and Lysine analogue 5:

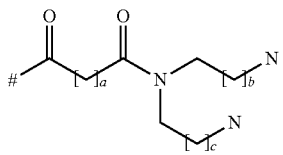

where a is an integer 0, 1 or 2 and wherein any methylene group of 1, 2 or 5 may be replaced by a methyleneoxy or ethyleneoxy group provided that this does not result in the formation of a carbonate or carbamate moiety within the building unit.

4. A macromolecule according to claim 1 wherein the core is a tri-amino compound selected from the group consisting of:

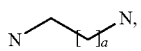

where a is an integer of 1 to 9,

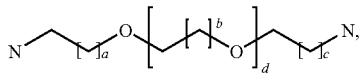

where a, b and c, are independently integers 1, 2, 3, 4 or 5, and d is an integer from 0-100,

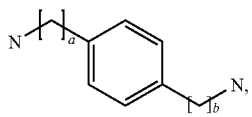

where a and b, are independently integers 0, 1, 2, 3, 4 or 5; and

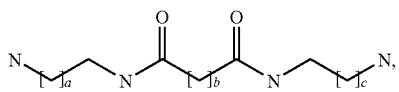

where a and c, are independently integers 1, 2, 3, 4, 5 or 6 and where b is an integer from 0, 1, 2, 3, 4, 5 or 6; and

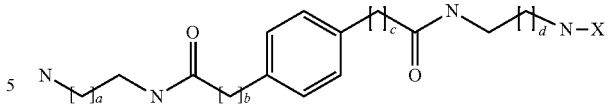

where a and d, are independently integers 1, 2, 3, 4, 5 or 6 and where b and c, are independently integers 0, 1, 2, 3, 4, 5 or 6, wherein X is a lysine or lysine analogue attached via its carboxyl group.

5. A macromolecule according to claim 4 wherein the core is selected from the group consisting of:

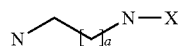

where a is an integer of 1, 2, 3, 4 or 5;

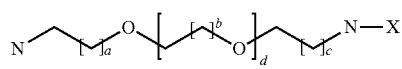

where a, b and c, are independently integers of 2 or 3 and d is an integer from 1-30; and

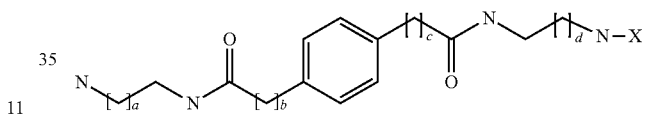

where a and d, are independently integers of 1 or 2 and where b and c, are independently integers from 0, 1 or 2.

6. A macromolecule according to claim 4 wherein the core is the following compound:

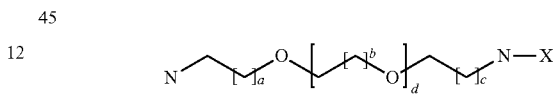

wherein a, b, c and d are each 1 wherein X is analogue 4

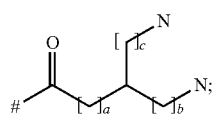

wherein each of a, b and c are 2.

7. A macromolecule according to claim 1 wherein the core is a tri-amino or tetra-amino compound selected from the group consisting of:

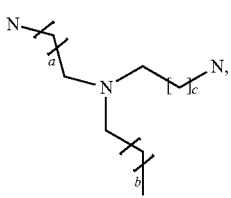

where a, b and c, are independently integers 1, 2, 3, 4, 5 or 6;

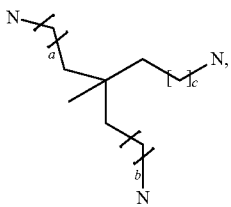

where a, b and c, are independently integers 0, 1, 2, 3, 4, 5 or 6;

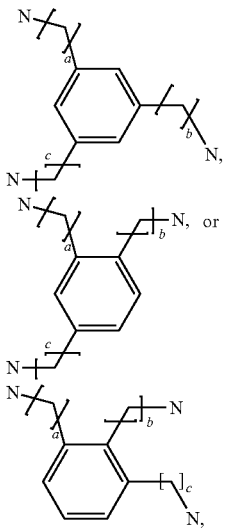

where a, b and c, are independently integers 0, 1, 2, 3, 4, 5 or 6;

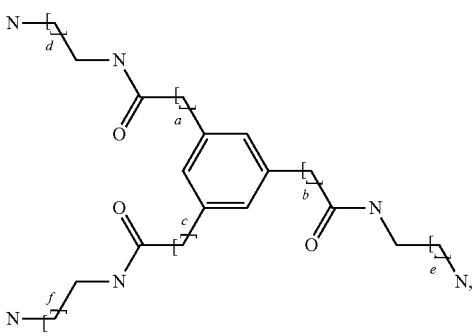

where a, b and c, are independently integers 0, 1, 2, 3, 4, 5 or 6; and d, e and f, are independently integers 1, 2, 3, 4, 5 or 6;

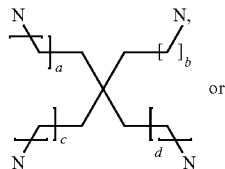

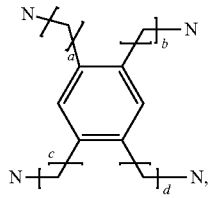

where a, b, c and d, are independently integers 0, 1, 2, 3, 4, 5 or 6;

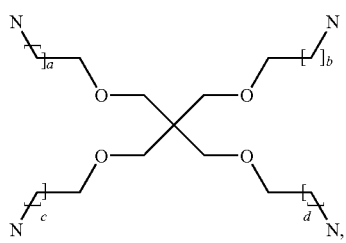

where a, b, c and d, are independently integers 1, 2, 3, 4, 5 or 6; and

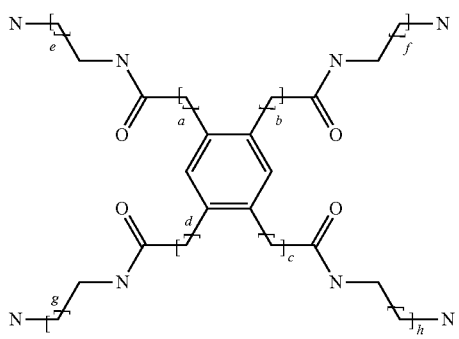

where a, b, c and d, are independently integers 0, 1, 2, 3, 4, 5 or 6; and e, f, g and h, are independently integers 1, 2, 3, 4, 5 or 6.

8. A macromolecule according to claim 7 wherein a tri-amino or tetra-amino compound is selected from the group consisting of:

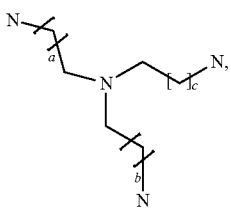

where a, b and c, which may be the same or different, are integers of 1 to 2; and

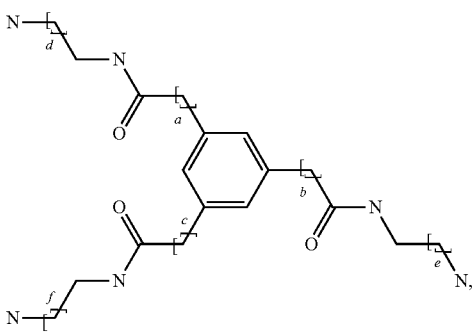

where a, b and c, are independently integers 0, 1 or 2; and d, e and f, are independently integers 1 or 2, or wherein a tetra-amine compound is selected from the group consisting of

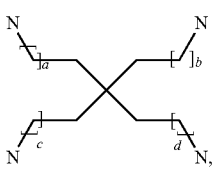

where a, b, c and d, are independently integers 0 or 1;

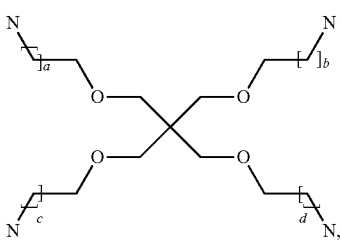

where a, b, c and d, are independently integers 1 or 2; and

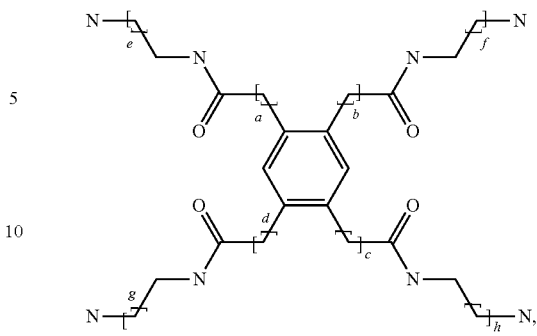

where a, b, c and d, are independently integers 0, 1 or 2; and e, f, g and h, are independently integers 1 or 2.

9. A macromolecule according to claim 1 wherein the dendrimer comprises 1, 2, 3, 4 or 5 layers of building units.

10. A macromolecule according to claim 9 wherein the dendrimer comprises 2, 3 or 4 layers of building units.

11. A macromolecule according to claim 1 further comprising at least one third functional moiety on attached to the surface amines of the outermost lysine or lysine analogue building units.

12. A macromolecule according to claim 1 wherein each surface amino nitrogen atom is attached to a functional moiety.

13. A macromolecule according to claim 1 wherein the pharmaceutically active agent is a peptide.

14. A macromolecule according to claim 1, further comprising a third functional moiety, which comprises a pharmacokinetic modifying agent.

15. A macromolecule according to claim 14 wherein the pharmacokinetic modifying agent is a polyethylene glycol.

16. A macromolecule according to claim 1 wherein the first functional moiety is an interacting agent.

17. A macromolecule according to claim 1 having a combination of functional moieties as defined below:

| 1st Functional Moiety | 2nd Functional Moiety | 3rd Functional Moiety |
| --- | --- | --- |
| Interacting agent | Pharmacokinetic modifying agent | — |
| Interacting agent | Pharmacokinetic modifying agent | Pharmaceutically active agent |
| Pharmaceutically active agent | Pharmacokinetic modifying agent | — |
| Pharmaceutically active agent | Pharmacokinetic modifying agent | Pharmaceutically active agent |

18. A macromolecule according to claim 1 wherein one or more functional moieties are attached to the core or surface nitrogen atoms via a linker.

19. A macromolecule according to claim 18 wherein the linker is a polyethylene glycol linker having from 1 to 100 repeat units.

20. A macromolecule according to claim 1 wherein a core nitrogen atom or surface nitrogen atom, and/or a functional moiety is modified by a modifier group to facilitate attachment.

21. A macromolecule according to claim 20 wherein the modifier group is selected from the group consisting of a haloacetamide, a maleimide or other thiol reactive moiety, a reactable thiol or exchangeable disulfide moiety, an aliphatic or aromatic aldehyde, a ketone, an alkoxyamine, a hydrazine, an azide, an alkyne, a hydrazide, an oligohistidine array or any peptide array, a nitrilotriacetic acid group, a carboxylate or reactive residue thereof, a chemical moiety capable of reacting with an organic halide, an organic alkyne via a metal catalysed coupling reaction and a moiety capable of enzymatic ligation.

22. A macromolecule according to claim 21 wherein the modifier group is selected from the group consisting of maleimide, haloacetamide, hydrazide, alkoxyamine, 3-(2-pyridyldithio)propionate, an azide, an alkyne, a hydrazine, an aliphatic or aromatic aldehyde, a ketone and a peptide array.

23. A composition comprising a macromolecule according to claim 1 and at least one pharmaceutically acceptable excipient, carrier or adjuvant therefor.

24. A macromolecule according to claim 18 wherein the linker is modified by a modifier group to facilitate attachment.

25. A macromolecule according to claim 5 wherein the core is a compound having the following structure:

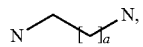

where a is an integer of 1 or 2, and X is a lysine or lysine analogue attached via its carboxyl group.

26. A macromolecule according to claim 4 wherein the core is:

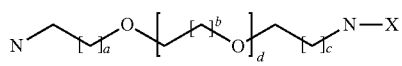

where a, b and c are independently 1 or 2 and d is 2, 4, 8, 12, 24 or 48, and X is a lysine or lysine analogue attached via its carboxyl group.

27. A macromolecule according to claim 1 wherein the core is a tetra-amino or penta-amino compound selected from the group consisting of:

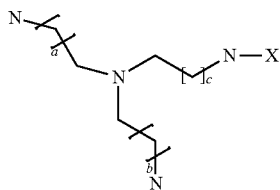

where a, b and c, are independently integers 1, 2, 3, 4, 5 or 6;

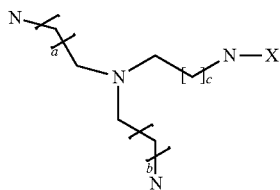

where a, b and c, are independently integers 0, 1, 2, 3, 4, 5 or 6;

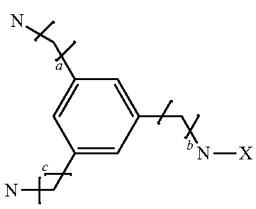

where a, b and c, are independently integers 0, 1, 2, 3, 4, 5 or 6;

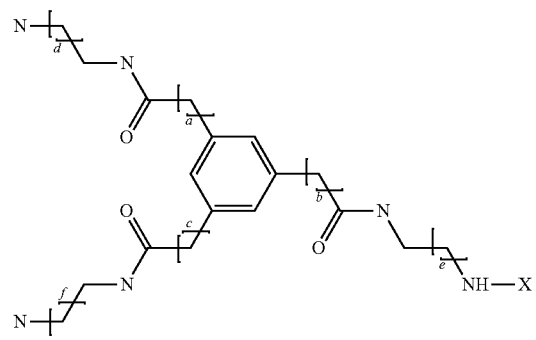

where a, b and c, are independently integers 0, 1, 2, 3, 4, 5 or 6; and d, e and f, are independently integers 1, 2, 3, 4, 5 or 6;

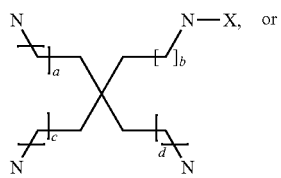

where a, b, c and d, are independently integers 0, 1, 2, 3, 4, 5 or 6;

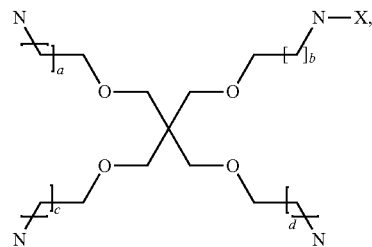

where a, b, c and d, are independently integers 1, 2, 3, 4, 5 or 6; and where X is a lysine or lysine analogue attached via its carboxyl group.

28. The macromolecule of claim 1 further comprising one or more further layers of lysine or lysine analogue building units attached to the first layer of lysine or lysine analogues through further amide bonds.

29. The macromolecule of claim 1, wherein the pharmaceutically active agent is selected from the group consisting of acetonemia preparations, anabolic agents, anaesthetics, analgesics, anti-acid agents, anti-arthritic agents, antibodies, anti-convulsants, anti-fungals, anti-histamines, anti-infectives, anti-inflammatories, anti-metabolites, anti-microbials, anti-mitotics, anti-parasitic agents, anti-protozoals, anti-ulcer agents, behaviour modification drugs, biologicals, blood and blood substitutes, bronchodilators, cancer therapy and related expectorants, cardiovascular pharmaceuticals, central nervous system pharmaceuticals, diuretics, contraceptives, growth hormones, diabetes therapies, hematinics fertility pharmaceuticals, hormone replacement therapies, growth promoters, immune suppressives, hemostatics, hormones and analogs, immunostimulants, minerals, muscle relaxants, nutraceuticals and nutritionals, ophthalmic pharmaceuticals, obesity therapeutics, pain therapeutics, osteoporosis drugs, proteins, peptides, polypeptides, retinoids, respiratory pharmaceuticals, sedatives, tranquilizers, transplantation products, urinary acidifiers, steroids, vaccines, and adjuvants.

30. A method of treating a subject comprising the step of administering a macromolecule according to claim 1 to said subject.

\* \* \* \* \*

UNITED STATES PATENT AND TRADEMARK OFFICE
CERTIFICATE OF CORRECTION

PATENT NO. : 8,420,067 B2
APPLICATION NO. : 12/377253
DATED : April 16, 2013
INVENTOR(S) : Krippner et al.

It is certified that error appears in the above-identified patent and that said Letters Patent is hereby corrected as shown below:

Page 1 (item 73, Assignee) at line 1, Change "Prahan," to --Prahran,--.

In column 1 at line 33, Change "that that" to --that--.

In column 5 at line 2, Change "that that" to --that--.

In column 7 at line 20, Change "or," to --or--.

In column 14 at line 39, Change "2." to --2;--.

In columns 25-26 at line 17 (approx.), Change "that" to --than--.

In columns 25-26 at line 26 (approx.), Change "•species" to --species--.

In columns 25-26 at line 29 (approx.), Change "phosphoralytic" to --phosphorolytic--.

In column 28 at line 57, Change "nitilotriacetic" to --nitrilotriacetic--.

In column 42 at line 2, Change "ink" to --m/z--.

In column 45 at line 23, Change "2811)." to --28H).--.

In column 46 at line 44, Change "Laetoglobulin" to --Lactoglobulin--.

In column 48 at line 38, Change "[CBz]2" to --[CBz]$_2$--.

In column 49 at line 11, Change "though" to --through--.

In column 50 at line 5, Change "[M+H$^+$];" to --[M+H]$^+$;--.

In column 54 at line 8, Change "[M+H$^+$];" to --[M+H]$^+$;--.

In column 54 at line 36, Change "[M+H$^+$];" to --[M+H]$^+$;--.

In column 54 at line 37, Change "[M+H$^+$]" to --[M+H]$^+$--.

In column 56 at line 60, In Claim 1, change "moieties;" to --moieties,--.

In column 57 at line 1, In Claim 1, change "fluorocarbons," to --fluorohydrocarbons,--.

Signed and Sealed this
Third Day of November, 2015

Michelle K. Lee
*Director of the United States Patent and Trademark Office*

CERTIFICATE OF CORRECTION (continued)
U.S. Pat. No. 8,420,067 B2

In column 58 at lines 15-25, In Claim 2, change

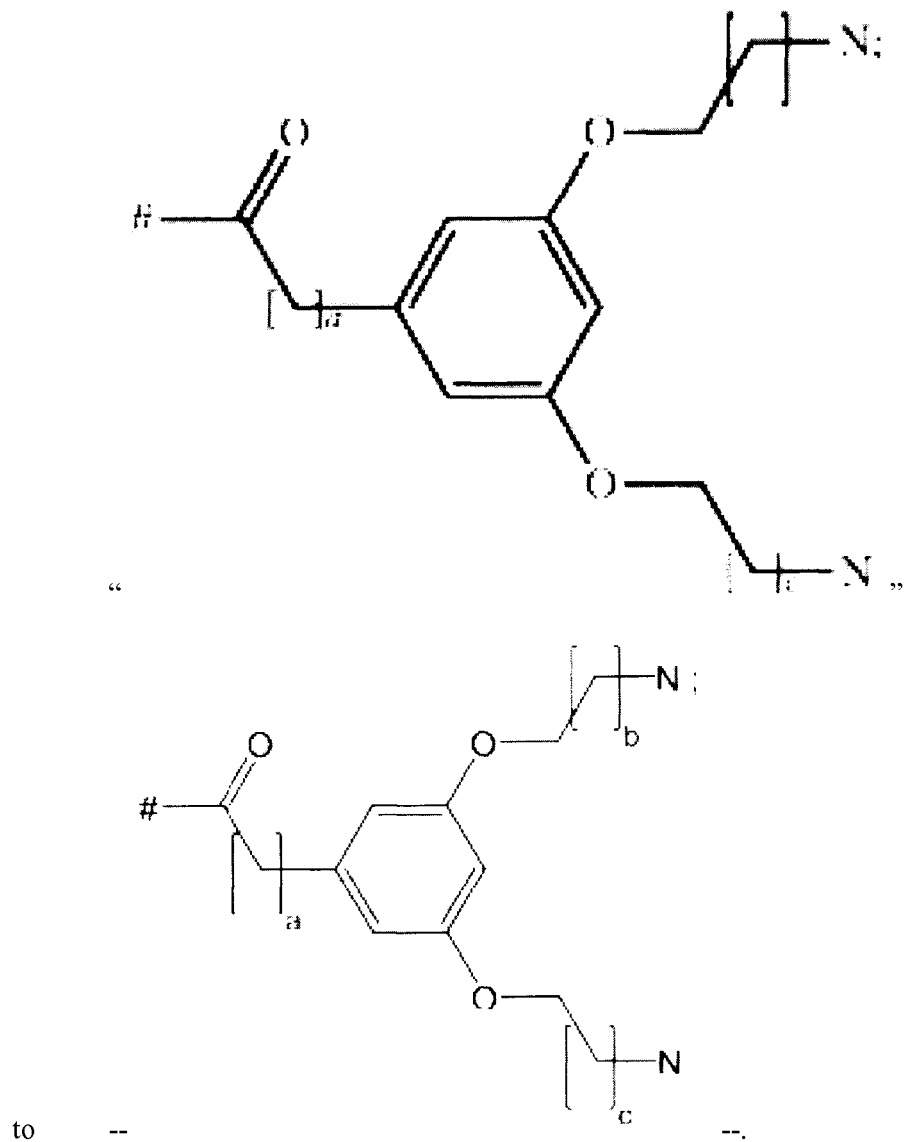

to --   --.

In column 58 at lines 30-40, In Claim 2, change
"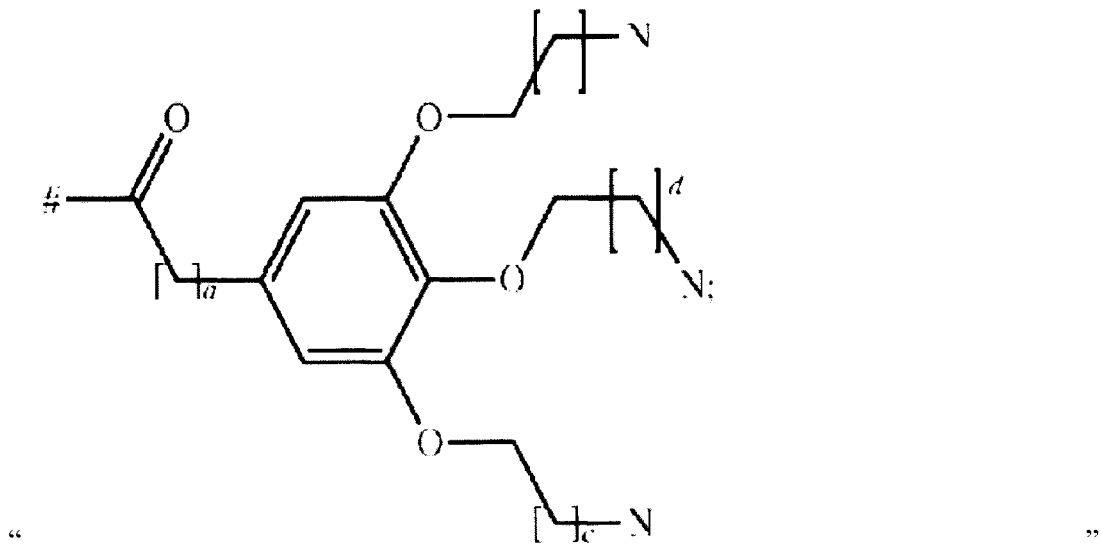"
to -- 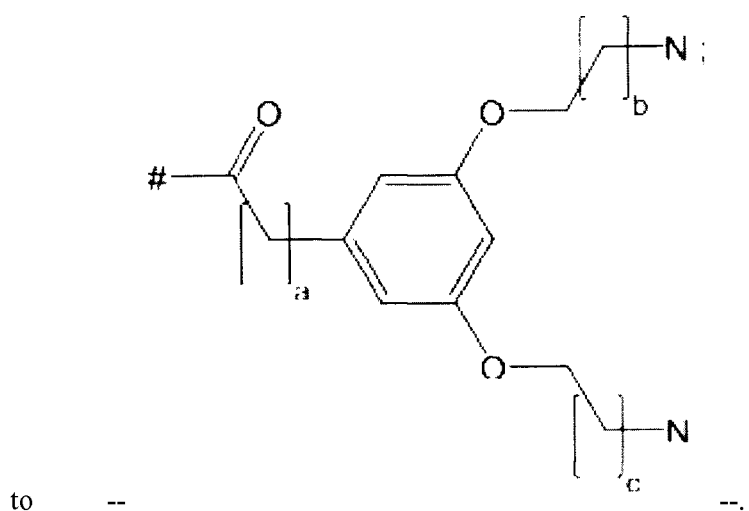 --.
In column 59 at line 26, In Claim 4, change "compound" to --compound,--.
In column 59 at lines 30-32, In Claim 4, change
"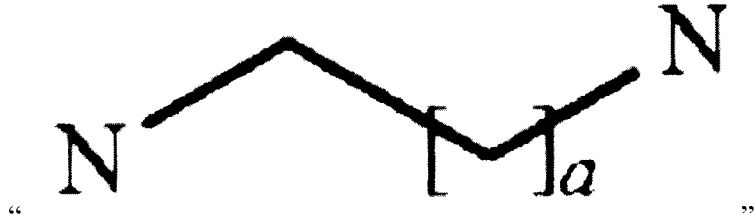"

CERTIFICATE OF CORRECTION (continued)
U.S. Pat. No. 8,420,067 B2

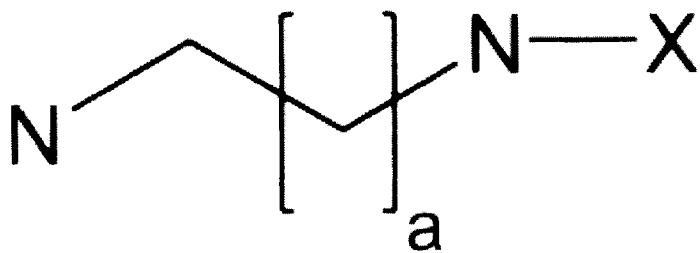

to -- -- .

In column 59 at lines 37-40, In Claim 4, change

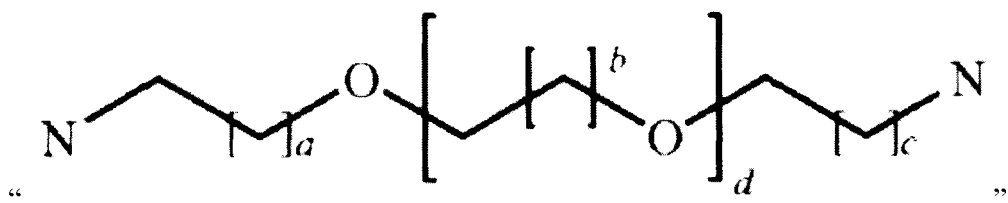

" "

to -- -- .

In column 59 at lines 47-50, In Claim 4, change

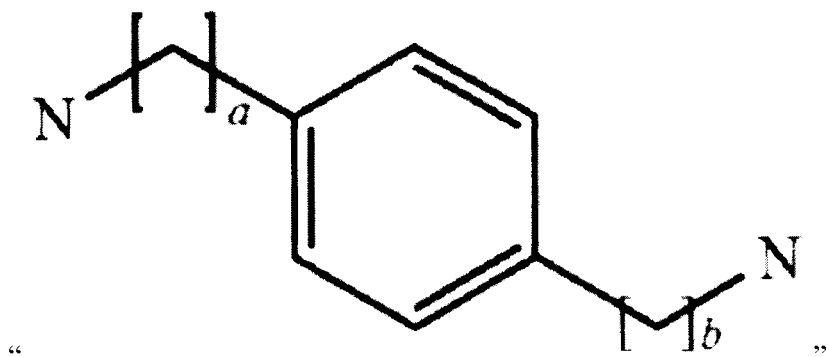

" "

to -- -- .

In column 59 at lines 59-62, In Claim 4, change
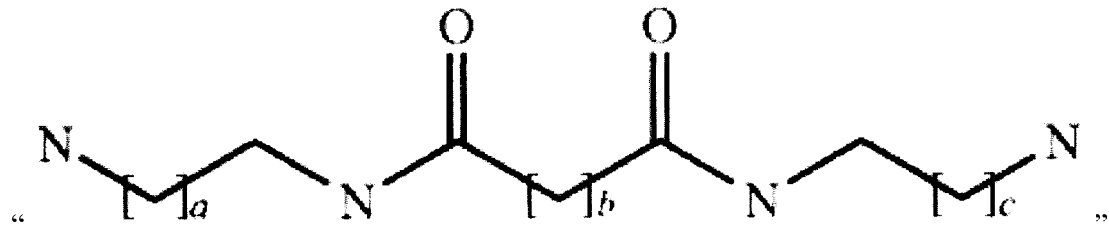
to
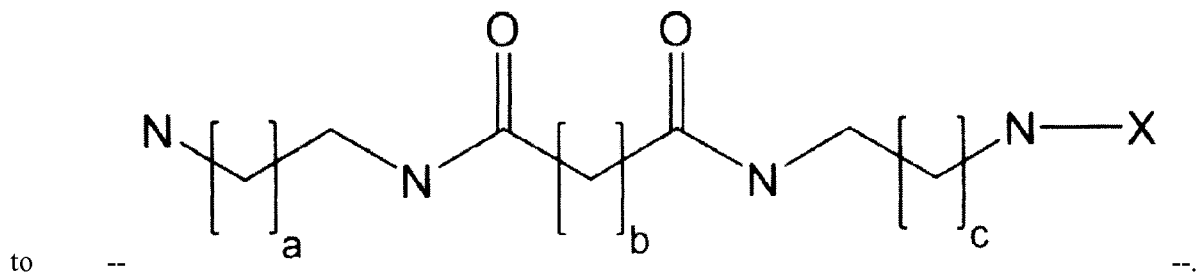
--.
In column 60 at lines 1-6, In Claim 4, change
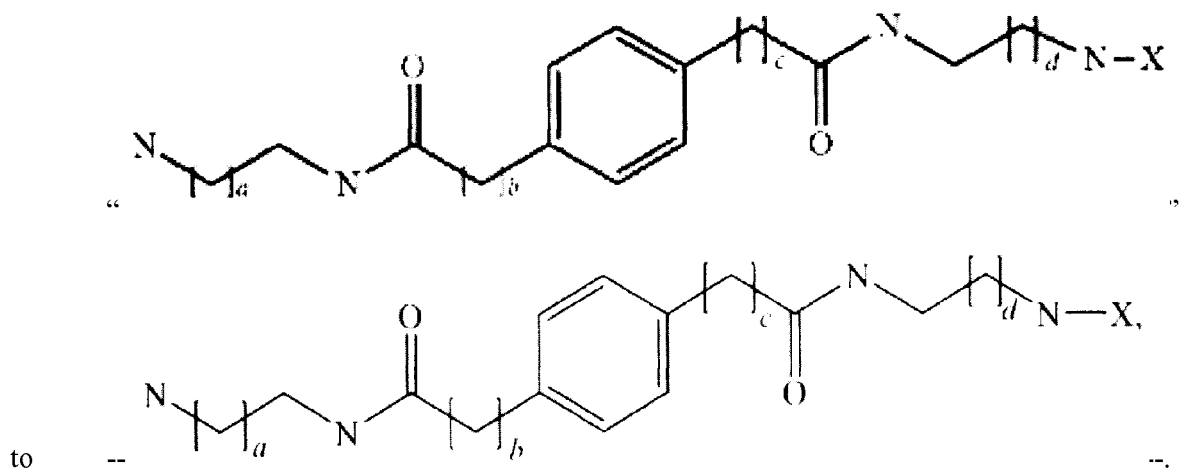
In column 60 at lines 24-28, In Claim 5, change
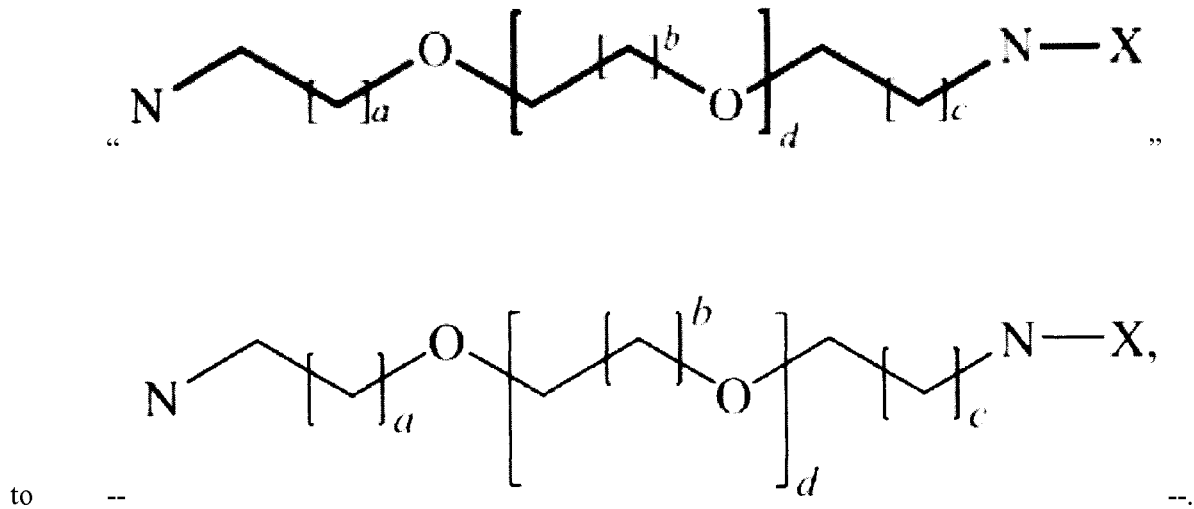
to --.

In column 60 at lines 32-38, In Claim 5, change
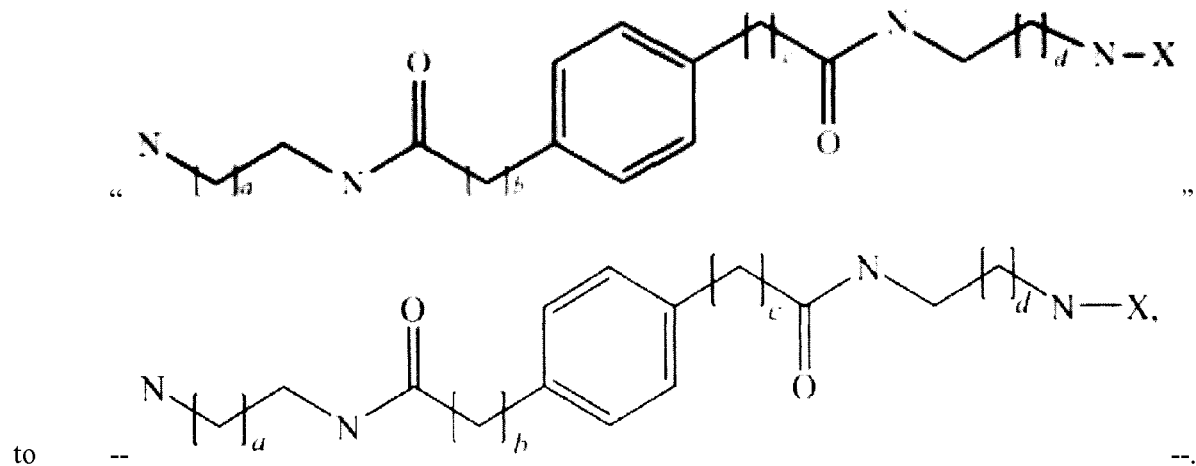
In column 60 at lines 55-60, In Claim 6, change
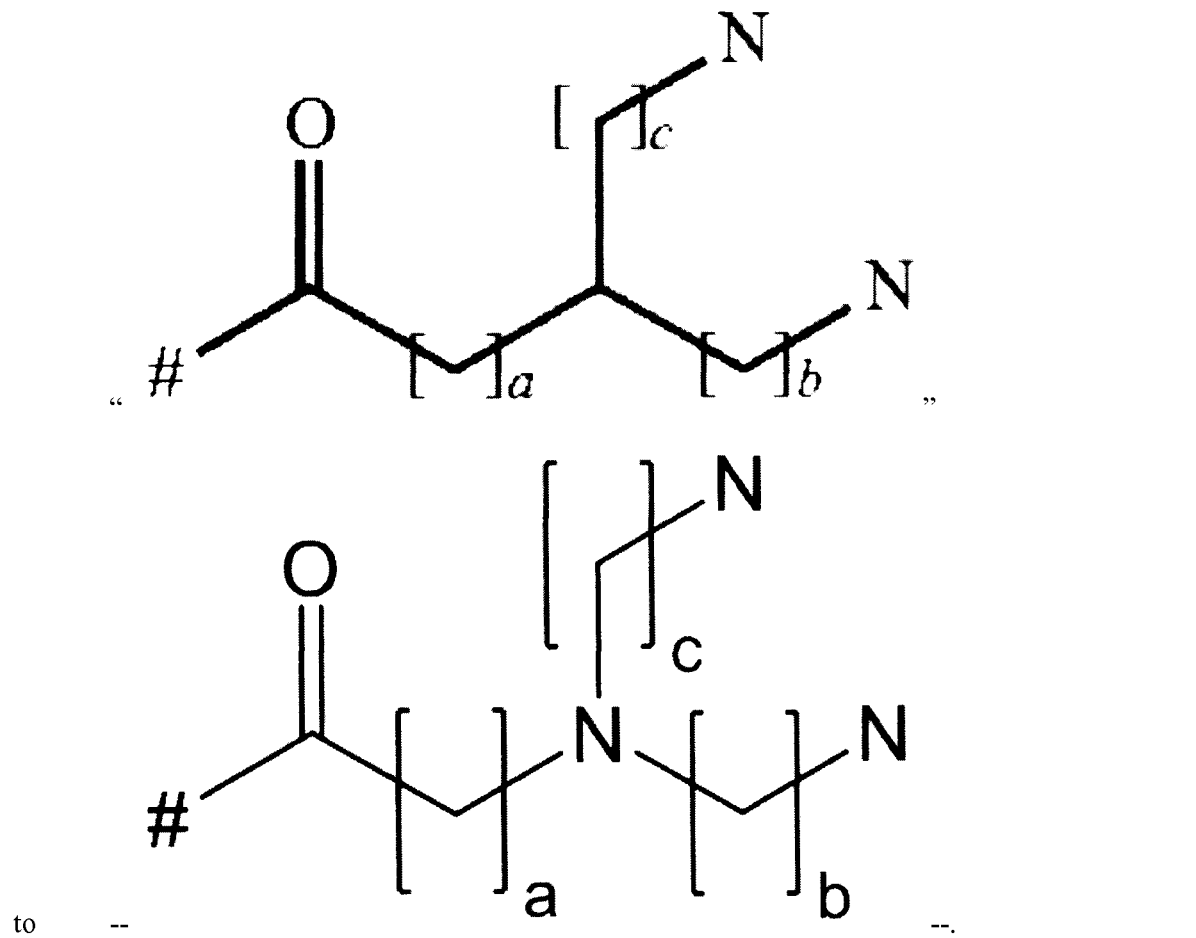

CERTIFICATE OF CORRECTION (continued)
U.S. Pat. No. 8,420,067 B2

In column 62 at lines 5-20, In Claim 7, change

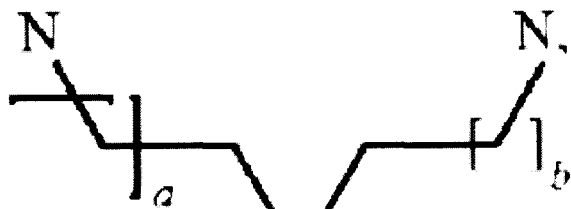　21 or

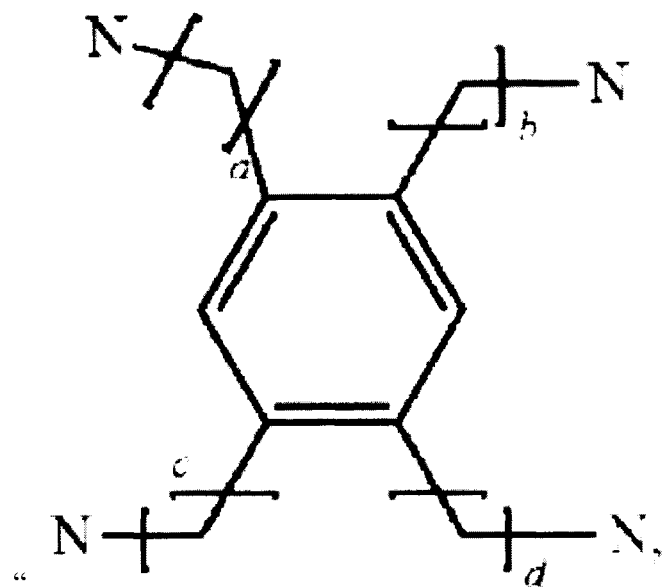　22

" "

CERTIFICATE OF CORRECTION (continued)
U.S. Pat. No. 8,420,067 B2

In column 62 at lines 5-20, In Claim 7, (cont'd)

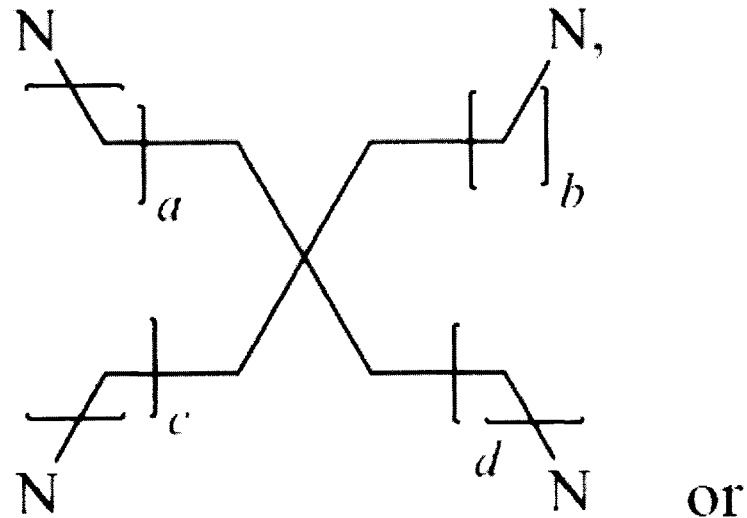

to -- 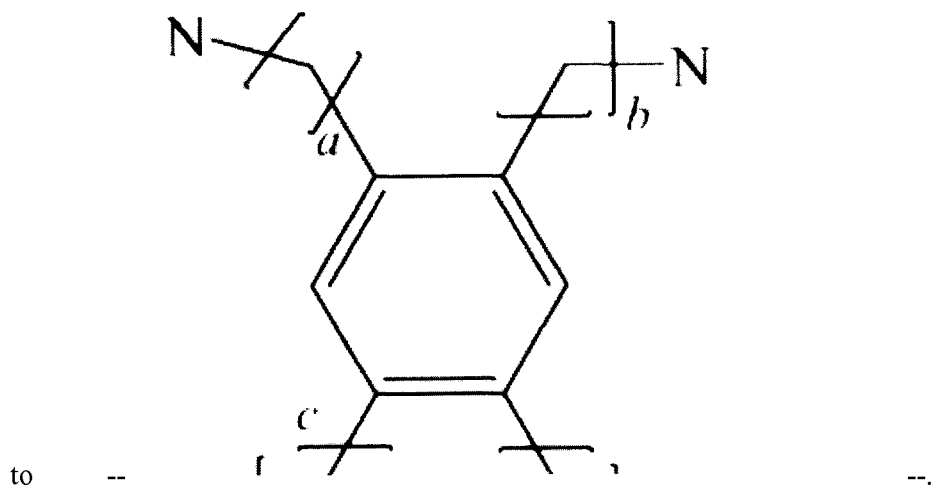 --.

In column 62 at lines 27-38, In Claim 7, change

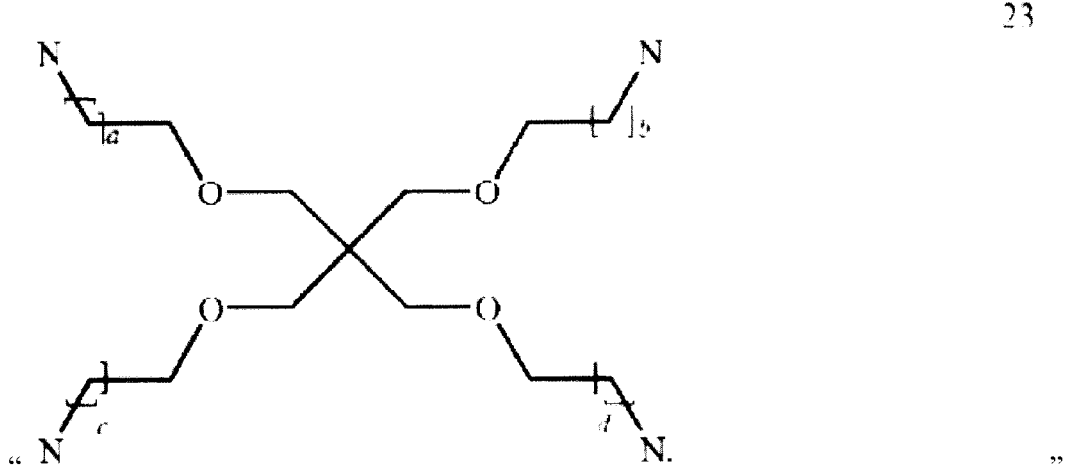

In column 62 at lines 27-38, In Claim 7, (cont'd)
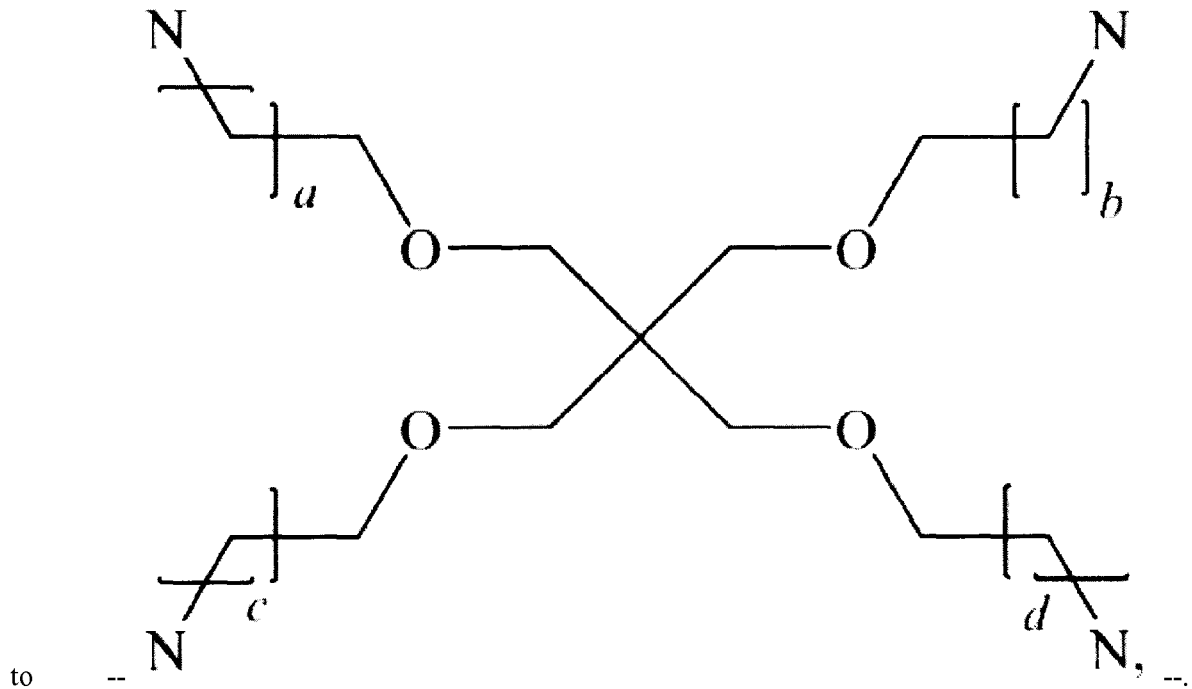
to
In column 63 at line 12, In Claim 8, change "to" to --or--.
In column 64 at line 23, In Claim 11, change "moiety on" to --moiety--.
In column 64 at line 33, In Claim 14, change "a third" to --third--.
In column 65 at lines 21-25, In Claim 25, change
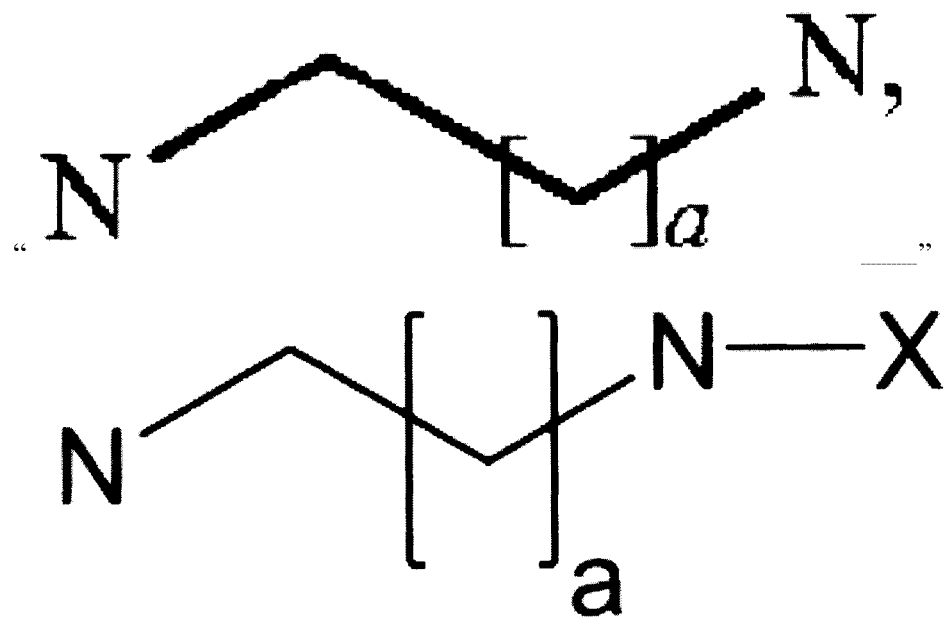
to

CERTIFICATE OF CORRECTION (continued)
U.S. Pat. No. 8,420,067 B2

In column 65 at lines 55-65, In Claim 27, change

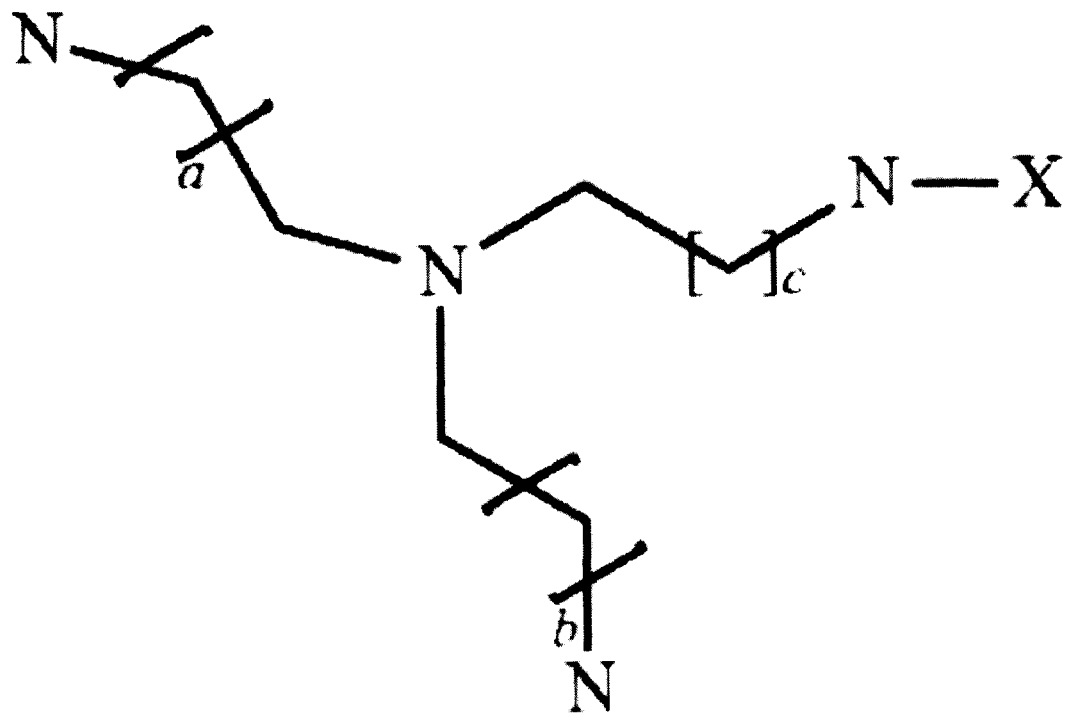

" "

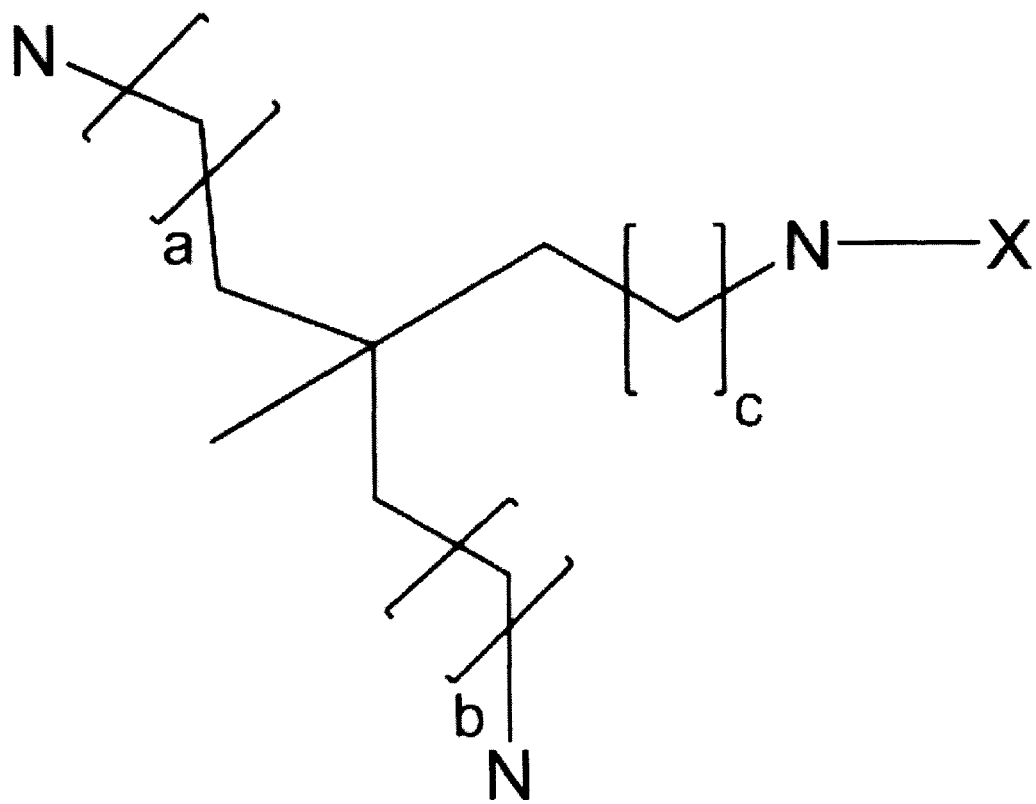

to -- --.